(12) United States Patent
Kircher, Jr. et al.

(10) Patent No.: US 12,237,064 B2
(45) Date of Patent: Feb. 25, 2025

(54) SYSTEM, METHOD AND ARTICLE FOR CONTROLLING THE DISPENSING OF INSULIN

(71) Applicant: Dexcom, Inc., San Diego, CA (US)

(72) Inventors: Robert C. Kircher, Jr., Seattle, WA (US); Richard S. Mauseth, Woodinville, WA (US); Jason N. Bishop, Bellevue, WA (US); Donald P. Matheson, Redmond, WA (US); Suray Bhatia, Seattle, WA (US); Jeff A. Bilmes, Seattle, WA (US)

(73) Assignee: Dexcom, Inc., San Diego, CA (US)

( * ) Notice: Subject to any disclaimer, the term of this patent is extended or adjusted under 35 U.S.C. 154(b) by 238 days.

(21) Appl. No.: 17/824,042

(22) Filed: May 25, 2022

(65) Prior Publication Data

US 2022/0375566 A1 Nov. 24, 2022

Related U.S. Application Data

(63) Continuation of application No. 16/857,030, filed on Apr. 23, 2020, now Pat. No. 11,373,748, which is a
(Continued)

(51) Int. Cl.
*G16H 20/17* (2018.01)
*A61B 5/145* (2006.01)
(Continued)

(52) U.S. Cl.
CPC ......... *G16H 20/17* (2018.01); *A61B 5/14532* (2013.01); *A61M 5/1723* (2013.01);
(Continued)

(58) Field of Classification Search
None
See application file for complete search history.

(56) References Cited

U.S. PATENT DOCUMENTS 5,971,922 A 10/1999 Arita et al.
6,572,542 B1 6/2003 Houben et al.
(Continued)

OTHER PUBLICATIONS

Binder J., et al., "Adaptive Probabilistic Networks with Hidden Variables," Machine Learning, vol. 29, No. (2-3), 1997, pp. 213-244.
(Continued)

*Primary Examiner* — Rodney E Fuller
(74) *Attorney, Agent, or Firm* — Kaplan Breyer Schwarz LLP

(57) ABSTRACT

An integrated circuit includes circuitry to control a process. The process includes adjusting fuzzy-logic control parameters based on received and retrieved blood glucose-related data, predicting blood glucose levels based on the received blood-glucose-related data, and generating control signals to control dispensing of insulin based on the received blood glucose-related data and the fuzzy-logic control parameters. The process may include predicting blood glucose levels based on the retrieved blood glucose-related data. The process may include transitioning between a post-meal correction protocol and a fasting protocol. The process may include transitioning from a post-meal correction protocol to a fasting protocol when a fasting criteria is satisfied.

40 Claims, 26 Drawing Sheets

Related U.S. Application Data continuation of application No. 16/118,555, filed on Aug. 31, 2018, now Pat. No. 10,668,214, which is a continuation of application No. 15/606,839, filed on May 26, 2017, now Pat. No. 10,080,842, which is a continuation of application No. 14/710,851, filed on May 13, 2015, now Pat. No. 9,694,133, which is a continuation of application No. 14/014,711, filed on Aug. 30, 2013, now Pat. No. 9,056,168, which is a continuation of application No. 12/305,582, filed as application No. PCT/US2007/014477 on Jun. 19, 2007, now Pat. No. 8,548,544.

(60) Provisional application No. 60/815,235, filed on Jun. 19, 2006, provisional application No. 60/859,625, filed on Nov. 17, 2006, provisional application No. 60/904,495, filed on Mar. 1, 2007.

(51) Int. Cl.
| | | |
|---|---|---|
| *A61M 5/172* | (2006.01) | |
| *G06N 5/048* | (2023.01) | |
| *G16H 20/10* | (2018.01) | |
| *G16H 20/13* | (2018.01) | |
| *G16H 50/50* | (2018.01) | |

(52) U.S. Cl.
CPC .............. *G06N 5/048* (2013.01); *G16H 20/10* (2018.01); *G16H 20/13* (2018.01); *G16H 50/50* (2018.01); *A61M 2230/005* (2013.01); *A61M 2230/201* (2013.01)

(56) References Cited

U.S. PATENT DOCUMENTS

| | | |
|---|---|---|
| 7,353,152 B2 | 4/2008 | Brazhnik et al. |
| 8,548,544 B2 * | 10/2013 | Kircher, Jr. ............ G16H 20/13 |
| | | 600/347 |
| 9,056,168 B2 | 6/2015 | Kircher et al. |
| 9,694,133 B2 | 7/2017 | Kircher et al. |
| 10,080,842 B2 | 9/2018 | Kircher et al. |
| 10,668,214 B2 | 6/2020 | Kircher et al. |
| 2003/0208113 A1 | 11/2003 | Mault et al. |
| 2004/0167418 A1 | 8/2004 | Nguyen et al. |
| 2004/0197846 A1 | 10/2004 | Hockersmith et al. |
| 2005/0038674 A1 | 2/2005 | Braig et al. |
| 2005/0065465 A1 | 3/2005 | Lebel et al. |
| 2005/0163842 A1 | 7/2005 | Boehm et al. |
| 2005/0171503 A1 | 8/2005 | Van Den Berghe et al. |
| 2005/0245878 A1 | 11/2005 | Mernoe et al. |
| 2006/0001471 A1 | 1/2006 | Chu |
| 2008/0183060 A1 | 7/2008 | Steil et al. |

OTHER PUBLICATIONS

Habbi A., et al., "An Improved Self-Tuning Mechanism of Fuzzy Control of Gradient Descent Method," Proceedings 17th European Simulation Multi Conference, 2003, pp. 43-47.

Nomura H., et al., "A Self-Tuning Method of Fuzzy Control by Descent Method," Proceedings of the IFSA '91, 1991, pp. 155-158.

Rabiner L.R., "A Tutorial on Hidden Markov Models and Selected Applications in Speech Recognition," Proceedings of the IEEE, vol. 77, No. 2, Feb. 1989, pp. 257-286.

* cited by examiner

| Fuzzy set for Dose | | | |
|---|---|---|---|
| Variable | A | D | W |
| D00 | 0.00 | 0.00 | 0.10 |
| D01 | 0.05 | 0.00 | 0.05 |
| D02 | 0.10 | 0.00 | 0.05 |
| D05 | 0.25 | 0.00 | 0.10 |
| D10 | 0.40 | 0.00 | 0.15 |
| D20 | 0.75 | 0.00 | 0.25 |
| D30 | 1.10 | 0.00 | 0.35 |
| D40 | 1.50 | 0.00 | 0.40 |
| D50 | 2.00 | 0.00 | 0.25 |
| D60 | 2.25 | 0.00 | 0.25 |
| D70 | 2.50 | 0.00 | 0.25 |
| D80 | 3.00 | 0.00 | 0.50 |
| D90 | 4.50 | 0.00 | 1.50 |

SYSTEM, METHOD AND ARTICLE FOR CONTROLLING THE DISPENSING OF INSULIN

BACKGROUND OF THE INVENTION

Field of the Invention

This disclosure generally relates to a system, method and article for predicting and controlling blood glucose levels, and more particularly to a system, method and article for controlling the dispensing of insulin.

Description of the Related Art

Carefully controlling blood sugar is a key to maintaining good health. Insulin, a hormone produced by the pancreas, helps maintain normal blood sugar levels. Diabetes mellitus, usually called diabetes, is a disease in which an individual's pancreas does not make enough insulin or the individual's body cannot use normal amounts of insulin properly. Hypoglycemia, blood glucose that is too low, and hyperglycemia, blood sugar that is too high, can result from poor control of blood glucose levels.

In otherwise healthy diabetics, uncontrolled or high blood sugar levels can lead to health complications such as blindness, heart diseases, and kidney disease. Recent research of patients in hospital Intensive Care Units has shown that trauma resulting from severe illness and surgery can also induce elevated blood sugar, which aggravates infection and extends the recovery process.

BRIEF SUMMARY OF THE INVENTION

This disclosure is directed to a system, method and device for automatically predicting and controlling blood glucose levels. This disclosure is further directed to a system, method and device for automatically controlling the dispensing of insulin. Yet further, this disclosure is directed to a system, method and device for automatically adjusting a control system to respond to insulin sensitivity in real time.

In one embodiment, a blood glucose system comprises means for sensing indications of blood glucose levels and means for predicting blood glucose levels based on sensed indications of blood glucose levels communicatively coupled to the means for sensing indications of blood glucose levels. In one embodiment, the control system further comprises means for dispensing insulin wherein the means for predicting is configured to control the means for dispensing insulin based on the sensed indications. In one embodiment, the means for sensing indications of blood glucose levels comprises a plurality of blood glucose sensors. In one embodiment, the blood glucose control system further comprises means for receiving user input. In one embodiment, the means for receiving user input comprises a keypad. In one embodiment, the means for receiving user input comprises a computer readable memory medium. In one embodiment, the blood glucose control system further comprises means for providing user output.

In one embodiment, the means for predicting is further configured to detect a dangerous condition. In one embodiment, the dangerous condition is an active insulin level above a threshold active insulin level and the means for predicting is further configured to suspend the dispensing of insulin when the dangerous condition is detected. In one embodiment, the dangerous condition is a predicted active insulin level above a threshold active insulin level and the means for predicting is further configured to suspend the dispensing of insulin when the dangerous condition is detected. In one embodiment, the dangerous condition is a blood glucose level above a high-threshold blood glucose level. In one embodiment, the dangerous condition is a predicted blood glucose level above a high-threshold blood glucose level. In one embodiment, the dangerous condition is a blood glucose level below a low-threshold blood glucose level. In one embodiment, the dangerous condition is a predicted blood glucose level below a low-threshold blood glucose level.

In one embodiment, the means for predicting is configured to control postprandial and fasting blood sugar in an insulin dependent diabetic and the sensed indications are compared to blood sugar targets which are a function of a level of compliance with an intensive insulin therapy protocol. In one embodiment, the means for predicting is configured to transition into a semi-automatic mode. In one embodiment, the means for predicting is configured to transition into a fully automatic mode. In one embodiment, the means for predicting is configured to detect high blood glucose levels. In one embodiment, the means for predicting is configured to predict high blood glucose levels. In one embodiment, the means for predicting is configured to detect low blood glucose levels. In one embodiment, the means for predicting is configured to predict low blood glucose levels. In one embodiment, the means for predicting is configured to selectively transition between a post-meal correction mode and a fasting mode based on the sensed indications of blood glucose levels. In one embodiment, the means for predicting is configured to selectively transition from the post-meal correction mode to the fasting mode when a fasting criteria is satisfied. In one embodiment, the means for predicting is configured to selectively transition from the fasting mode to the post-meal correction mode when a prandial event is detected. In one embodiment, the means for predicting is configured to selectively transition from the fasting mode to a user-input mode when a prandial event is detected.

In one embodiment, the means for predicting is configured to maintain a data structure based on the sensed indications. In one embodiment, the means for predicting is configured to predict blood glucose levels based on the maintained data structure. In one embodiment, the means for predicting is configured to predict blood glucose levels based on the sensed blood glucose levels and previously predicted blood glucose levels. In one embodiment, the means for predicting is configured to predict a subsequent blood glucose level by treating a previously predicted blood glucose level as an actual blood glucose level.

In one embodiment, the means for predicting is configured to maintain a fuzzy-logic rules matrix based on the sensed indications. In one embodiment, the means for predicting is configured to maintain the fuzzy-logic rules matrix based on the sensed indications and previously predicted blood glucose levels. In one embodiment, the means for predicting is configured to predict blood glucose levels based on the maintained fuzzy-logic rules matrix.

In one embodiment, a control system comprises a blood glucose sensor system configured to sense data indicative of blood glucose levels, a user input device configured to receive user data, an insulin dispenser configured to selectively dispense insulin in response to a control signal, and a controller configured to selectively generate the control signal and communicatively coupled to the sensor system, the dispenser and the user input device, wherein the controller is configured to automatically transition between states of operation comprising a compliant state of operation and an insulin-dose-control state of operation. In one embodiment, the states of operation further comprise a semi-compliant state of operation and the controller is configured to automatically transition between the compliant state of operation, the semi-compliant state of operation and the insulin-dose-control state of operation.

In one embodiment, the control system further comprises a memory coupled to the controller and configured to store previously sensed data related to blood glucose levels, wherein the controller is configured to selectively generate the control signal based on currently sensed data and the stored previously sensed data. In one embodiment, the control system further comprises a blood glucose level predictor.

In one embodiment, the blood glucose sensor system comprises a plurality of blood glucose sensors. In one embodiment, the blood glucose sensor system is configured to sense data related to blood glucose levels at fifteen-minute intervals, or other periodic or non-periodic intervals.

In one embodiment, the controller is configured to transition to the insulin-dose-control state of operation when a fasting criteria is satisfied. In one embodiment, the controller is configured to determine whether the fasting criteria is satisfied by comparing an indicator of a current blood glucose level to a fasting blood glucose level range. In one embodiment, the control signal comprises and indication of an amount of insulin to be dispensed by the insulin dispenser. In one embodiment, the control signal comprises an indication of a schedule for insulin to be dispensed by the insulin dispenser. In one embodiment, the controller is configured to transition out of the insulin-dose-control state in response to an indication of a prandial event. In one embodiment, the controller is configured to transition from the insulin dose control state to the compliant state when the indication of a prandial event includes an indication of a blood sugar content. In one embodiment, the controller is further configured to selectively transition to a user-input mode of operation.

In one embodiment, the controller is configured to transition to the user-input mode of operation in response to an indication of a dangerous condition. In one embodiment, the indication of a dangerous condition is an indication that a blood glucose level exceeds a threshold maximum level. In one embodiment, the indication of a dangerous condition is an indication that a blood glucose level is below a threshold minimum level. In one embodiment, the indication of a dangerous condition is an indication that an active insulin level exceeds a threshold active insulin level. In one embodiment, the controller employs fuzzy logic to generate the control signal in the fasting mode of operation. In one embodiment, the controller employs a look-up table to generate the control signal in the fasting mode of operation. In one embodiment, the control signal is generated by comparing sensed blood glucose levels to target levels.

In one embodiment, a method of automatically controlling dispensing of insulin comprises automatically analyzing data related to blood glucose levels, when the analysis of the data is consistent with a prandial event, automatically generating control signals to cause insulin to be dispensed according to a post-meal correction protocol; and when the analysis of the data is consistent with fasting, automatically generating control signals to cause insulin to be dispensed according to a fasting protocol. In one embodiment, the post-meal correction protocol comprises dispensing a bolus insulin dose. In one embodiment, the post-meal correction protocol comprises adjusting a basal insulin dose. In one embodiment, the method of automatically controlling dispensing of insulin further comprises measuring indicators of blood glucose levels, wherein analyzing the data comprises analyzing the measured indicators of blood glucose levels. In one embodiment, the method of automatically controlling dispensing of insulin further comprises receiving user-input-data, wherein analyzing the data comprises analyzing the received user-input-data.

In one embodiment, the method of automatically controlling dispensing of insulin further comprises automatically detecting a dangerous condition; and when the dangerous condition is detected, selectively generating control signals to terminate automatic control. In one embodiment, automatically detecting a dangerous condition comprises determining whether a blood glucose level is above a threshold blood glucose level. In one embodiment, automatically detecting a dangerous condition comprises determining whether a rate of change of a blood glucose level is above a threshold rate of change. In one embodiment, automatically detecting a dangerous condition comprises determining whether an active insulin level exceeds a threshold active insulin level and, when the dangerous condition is detected, selectively generating control signals to cause the suspension of dispensing of insulin.

In one embodiment, the method of automatically controlling dispensing of insulin further comprises, when the dangerous condition is detected, generating control signals to alert a user to the dangerous condition. In one embodiment, the method of automatically controlling dispensing of insulin further comprises, when the dangerous condition is detected, generating control signals to request user input. In one embodiment, the method of automatically controlling dispensing of insulin further comprises employing fuzzy logic to generate the control signals to cause insulin to be dispensed when insulin is dispensed under the fasting protocol. In one embodiment, the fuzzy logic inputs comprise an indicator of blood glucose level, an indicator of a rate of change of the blood glucose level, and an indicator of an acceleration of the blood glucose level. In one embodiment, the method of automatically controlling dispensing of insulin further comprises maintaining a data structure. In one embodiment, the method of automatically controlling dispensing of insulin further comprises maintaining a fuzzy-logic matrix. In one embodiment, maintaining a fuzzy logic matrix comprises modifying values in the fuzzy-logic matrix based on the analysis of the data related to blood glucose levels. In one embodiment, the analysis of the data comprises predicting future blood glucose levels. In one embodiment, the method of automatically controlling dispensing of insulin further comprises storing instructions in a computer readable memory medium to cause a controller to control the dispensing of insulin by performing the method.

In one embodiment, a computer-readable memory medium contains instructions for causing a controller to control the dispensing of insulin by analyzing data related to blood glucose levels, when the analysis of the data is consistent with a prandial event, generating control signals to cause insulin to be dispensed according to a post-meal correction protocol, and when the analysis of the data is consistent with fasting, generating control signals to cause insulin to be dispensed according to a fasting protocol. In one embodiment, the instructions further cause the controller to control the dispensing of insulin by analyzing indicators of a dangerous condition, and when the analysis of the indicators of a dangerous condition is consistent with the dangerous condition, generating control signals to suspend dispensing of insulin. In one embodiment, the post-meal correction protocol comprises dispensing a bolus insulin dose. In one embodiment, the post-meal correction protocol comprises adjusting a basal insulin dose. In one embodiment, the instructions further cause the controller to control the dispensing of insulin by measuring indicators of blood glucose levels, wherein the analyzed data comprises the measured indicators of blood glucose levels. In one embodiment, the instructions further cause the controller to control the dispensing of insulin by receiving user-input-data, wherein the analyzed data comprises the received user-input-data. In one embodiment, the instructions further cause the controller to control the dispensing of insulin by predicting future blood glucose levels, wherein the analyzed data comprises the predicted future blood glucose levels. In one embodiment, the instructions further cause the controller to control the dispensing of insulin by determining an active insulin level, wherein the analyzed data comprises the determined active insulin level. In one embodiment, the instructions further cause the controller to control the dispensing of insulin by maintaining a fuzzy-logic matrix, wherein the analyzed data comprises values in the maintained fuzzy-logic matrix.

In one embodiment, a system for predicting blood glucose levels comprises a data input subsystem configured to receive blood glucose-related data, a blood glucose level predictor coupled to the input system and configured to predict blood glucose levels based on the received data, and an output subsystem coupled to the blood glucose level predictor and configured to selectively generate output signals based on the received data and the predicted blood glucose levels. In one embodiment, the system for predicting blood glucose levels further comprises a processor and a memory coupled to the processor and the blood glucose level predictor wherein the memory is configured to generate predicted blood glucose levels from the received blood glucose-related data. In one embodiment, the output signals comprise control signals for controlling dispensing of insulin. In one embodiment, the system for predicting blood glucose levels further comprises an insulin dispenser. In one embodiment, the output signals comprise control signals for maintaining blood glucose levels within a threshold fasting range. In one embodiment, the output signals comprise control signals for bringing blood glucose levels within the threshold fasting range. In one embodiment, the output signals are control signals for selectively causing an alert signal to be generated.

In one embodiment, a method of predicting blood glucose levels comprises receiving historical data related to blood glucose levels, automatically analyzing the historical data, and automatically predicting a future blood glucose level based on the analysis. In one embodiment, the method of predicting blood glucose levels further comprises receiving real-time blood-glucose-related data, wherein the automatically analyzing comprises comparing the real-time blood-glucose-related data to the analyzed historical data. In one embodiment, the method of predicting blood glucose levels further comprises maintaining model parameters, wherein the automatically analyzing comprises applying the model parameters. In one embodiment, maintaining the model parameters comprises maintaining a fuzzy-logic table. In one embodiment, maintaining the model parameters comprises comparing real-time blood-glucose-related data to historical data and selectively revising the model parameters based on the comparison. In one embodiment, the automatically analyzing the historical data comprises calculating an active insulin level. In one embodiment, the automatically analyzing comprises comparing changes in blood glucose levels with time. In one embodiment, the automatically analyzing comprises applying a probability model. In one embodiment, the automatically analyzing comprises maintaining a dynamic probability model.

In one embodiment, a method of dispensing insulin comprises receiving blood glucose data, generating blood glucose prediction data, comparing the received blood glucose data to the generated blood glucose prediction data, and generating control signals to control dispensing of insulin based on the comparison. In one embodiment, the method of dispensing insulin further comprises adjusting control parameters based on the comparison. In one embodiment, the generating control signals comprises applying the control parameters. In one embodiment, the control parameters are model parameters used to generate the blood glucose prediction data. In one embodiment, the control parameters comprise fuzzy-logic multipliers. In one embodiment, adjusting the control parameters comprises adjusting a fuzzy logic rules matrix. In one embodiment, the fuzzy logic rules matrix is adjusted according to a dosing matrix coherency policy.

In one embodiment, a system for controlling the dispensing of insulin comprises a data input subsystem configured to received blood glucose-related data, a blood glucose level predictor coupled to the input system and configured to predict blood glucose levels based on the received data, a parameter adjuster, and an output subsystem configured to generate control signals to control the dispensing of insulin based on received data and the predicted blood glucose levels. In one embodiment, the blood glucose level predictor is configured to predict blood glucose levels based on parameters of a statistical model and the parameter adjuster is configured to adjust the parameters of the statistical model. In one embodiment, the output system is configured to generate the control signals based on control parameters and the parameter adjuster is configured to adjust the control parameters. In one embodiment, the parameter adjuster is configured to adjust the control parameters based on a comparison of the predicted blood glucose levels to the received data.

In one embodiment, a blood glucose control system comprises means for sensing indications of blood glucose levels, means for maintaining control parameters, and means for generating output signals based on sensed indications of blood glucose levels and the maintained control parameters communicatively coupled to the means for sensing indications of blood glucose levels and the means for maintaining control parameters. In one embodiment, the means for generating output signals comprises means for predicting blood glucose levels based on the sensed indications of blood glucose levels. In one embodiment, the blood glucose control system further comprises means for dispensing insulin, wherein the output signals comprise control signals to control the means for dispensing insulin. In one embodiment, the means for sensing indications of blood glucose levels comprises a plurality of blood glucose sensors. In one embodiment, the blood glucose control sensor further comprises means for receiving user input. In one embodiment, the blood glucose control sensor further comprises means for providing output data, wherein the output signals comprise control signals to control the means for providing output data. In one embodiment, the means for generating output signals is further configured to detect a dangerous condition. In one embodiment, the dangerous condition is an active insulin level above a threshold active insulin level and the means for generating output signals is further configured to suspend the dispensing of insulin when the dangerous condition is detected. In one embodiment, the dangerous condition is a predicted active insulin level above a threshold active insulin level and the means for generating output signals is further configured to suspend the dispensing of insulin when the dangerous condition is detected. In one embodiment, the means for generating output signals is configured to transition into a semi-automatic mode. In one embodiment, the means for generating output signals is configured to transition into a fully automatic mode. In one embodiment, the means for generating output signals is configured to detect high blood glucose levels. In one embodiment, the means for generating output signals is configured to predict high blood glucose levels. In one embodiment, the means for generating output signals is configured to selectively transition between a post-meal correction mode and a fasting mode. In one embodiment, the means for generating output signals is configured to selectively transition from the post-meal correction mode to the fasting mode when a fasting criteria is satisfied. In one embodiment, the means for generating output signals is configured to selectively transition from the fasting mode to the post-meal correction mode when a prandial event is detected. In one embodiment, the means for generating output signals is configured to selective transition from the fasting mode to a user-input mode when a prandial event is detected. In one embodiment, the control parameters comprise model parameters. In one embodiment, the control parameters comprise fuzzy-logic multipliers. In one embodiment, the means for maintaining control parameters is configured to selectively adjust a fuzzy logic rules matrix. In one embodiment, the means for maintaining is configured to selectively adjust the fuzzy logic rules matrix according to a dosing matrix coherency policy. In one embodiment, the means for generating is configured to predict a subsequent blood glucose level by treating a previously predicted blood glucose level as an actual blood glucose level. In one embodiment, the means for maintaining is configured to maintain a fuzzy-logic rules matrix based on the sensed indications. In one embodiment, the means for maintaining is configured to maintain the fuzzy-logic rules matrix based on the sensed indications and previously predicted blood glucose levels. In one embodiment, the means for generating is configured to predict blood glucose levels based on the maintained fuzzy-logic rules matrix.

In one embodiment, an insulin dispensing system comprises means for sensing indications of blood glucose levels, means for dispensing insulin, means for receiving user input, means for providing user output, and means for controlling the means for dispensing insulin communicatively coupled to the means for sensing indications of blood glucose levels, the means for receiving user input and the means for providing user output, wherein the means for controlling the means for dispensing insulin is configured to automatically transition between a post-meal correction protocol and a fasting protocol based on sensed indications of blood glucose levels.

In one embodiment, the means for sensing indications of blood glucose levels comprises a plurality of blood glucose sensors. In one embodiment, the means for receiving user input comprises a keypad. In one embodiment, the means for controlling the means for dispensing insulin is further configured to detect a dangerous condition and to suspend the dispensing of insulin when the dangerous condition is detected. In one embodiment, the dangerous condition is an active insulin level above a threshold active insulin level. In one embodiment, the means for controlling the means for dispensing insulin is configured to control postprandial and fasting blood sugar in an insulin dependent diabetic and the sensed indications are compared to blood sugar targets which are a function of a level of compliance with an intensive insulin therapy protocol. In one embodiment, the means for controlling the means for dispensing insulin is configured to transition into a semi-automatic mode. In one embodiment, the means for controlling the means for dispensing insulin is configured to transition into a fully automatic mode. In one embodiment, the means for controlling the means for dispensing insulin is configured to detect high blood glucose levels. In one embodiment, the means for controlling the means for dispensing insulin is configured to predict high blood glucose levels. In one embodiment, the means for controlling the means for dispensing insulin is configured to detect low blood glucose levels. In one embodiment, the means for controlling the means for dispensing insulin is configured to predict low blood glucose levels.

In one embodiment, a blood glucose control system comprises a processor, a memory, a data input subsystem, a blood glucose level predictor, a parameter and model adjuster, an output subsystem, and a bus system. In one embodiment, a blood glucose control system comprises a blood glucose sensor system configured to sense data indicative of blood glucose levels; an insulin dispenser configured to selectively dispense insulin in response to a control signal; and a controller configured to selectively generate the control signal and communicatively coupled to the sensor system. In one embodiment, the blood glucose control system further comprises a user input device configured to receive user input.

In one embodiment, a system for dispensing insulin comprises a computing device having a computer-readable memory medium. In one embodiment, in a system for dispensing insulin comprising a computing device having a computer-readable memory medium, the contents of the computer-readable memory medium causes the computing device to perform a method for dispensing insulin. In one such embodiment, the method for dispensing insulin comprises receiving blood glucose data; generating blood glucose prediction data; comparing the received blood glucose data to the generated blood glucose prediction data; based on the comparison, generating control signals to control dispensing of insulin; and, based on the comparison, adjusting control parameters.

In one embodiment, fuzzy logic control parameters may be automatically adjusted on the basis of a physician-defined ideal trajectory. In one embodiment, a blood sugar prediction model may provide a method for automatically adjusting fuzzy logic control parameters. In one embodiment, the prediction model may be statistical. In one embodiment, a fuzzy logic controller may be adaptive. In one embodiment, a fuzzy logic controller may be based on a physician-defined blood sugar trajectory and/or based on a statistical model of a glucoregulatory system of a patient. In one embodiment, the blood sugar prediction model may be used in a device for alerting a patient.

The various embodiments disclosed herein may be employed, for example, as stand-alone systems or as components operative with one or more disclosed components in an integrated blood sugar management system, such as a system for controlling the dispensing of insulin. The embodiments may be combined in whole or in part to create additional embodiments.

BRIEF DESCRIPTION OF THE SEVERAL VIEWS OF THE DRAWINGS

In the drawings, identical reference numbers identify similar elements or acts, unless the context indicates otherwise. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not necessarily intended to convey any information regarding the actual shape of particular elements, and have been selected solely for ease of recognition in the drawings.

DETAILED DESCRIPTION OF THE INVENTION

In the following description, certain details are set forth in order to provide a thorough understanding of various embodiments of devices, methods and articles. However, one of skill in the art will understand that other embodiments may be practiced without these details. In other instances, well-known structures and methods associated with blood glucose sensors, data transmission, semiconductor devices, insulin dispensers and control systems have not been shown or described in detail to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is as "including, but not limited to."

Reference throughout this specification to "one embodiment," or "an embodiment" means that a particular feature, structure or characteristic described in connection with the embodiment is included in at least one embodiment. Thus, the appearances of the phases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure or the claimed invention.

Figure 1:
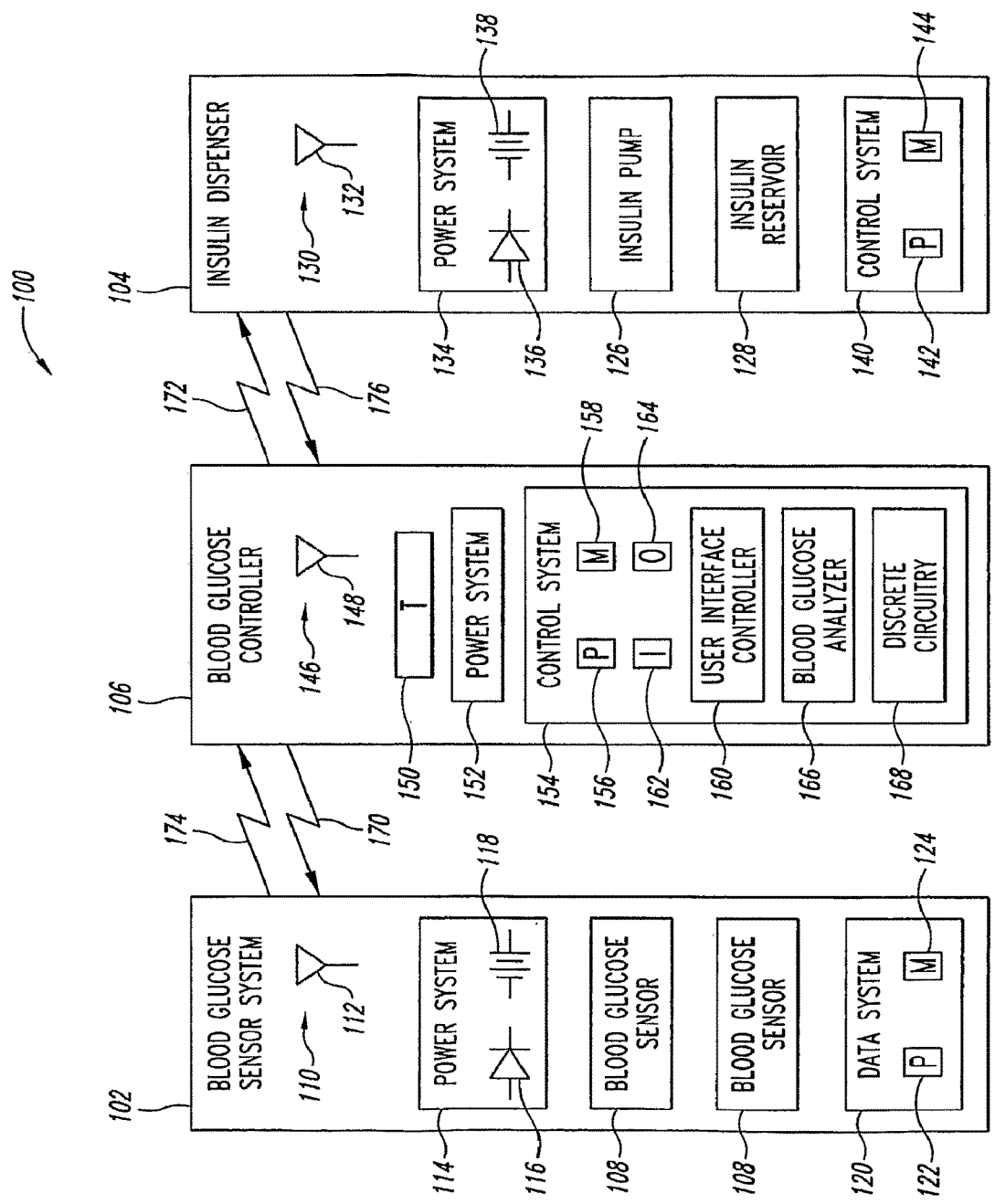
FIG. 1 is a functional block diagram of an embodiment of a dispenser control system.

FIG. 1 is a functional block diagram of a dispenser control system 100 comprising a sensor system, which as illustrated is a blood glucose sensor system 102, a dispenser, which as illustrated is an insulin dispenser 104, and a controller, which as illustrated is a blood glucose controller 106.

The blood glucose sensor system 102 is a device that measures blood glucose levels or an indication of blood glucose levels. The blood glucose sensor system 102 may operate with, or without, user interaction, as discussed in more detail below. The blood glucose sensor system 102 may be configured to take periodic measures, such as measurements every fifteen minutes. The blood glucose sensor system 102 may be configured to take measurements in response to received commands. The blood glucose sensor system 102 may be implanted, for example, subcutaneously, intramuscularly or intravenously. The blood glucose sensor system 102 may measure blood glucose levels directly or indirectly. For example, the blood glucose sensor system 102 may be configured to measure interstitial fluid glucose levels.

The blood glucose sensor system 102 as illustrated comprises one or more blood glucose sensors 108, a communication system 110, which as illustrated comprises an antenna 112, an optional power system 114, which as illustrated comprises an optional rectifier 116 and an optional battery 118, and a data system 120, which as illustrated comprises a processor 122 and a memory 124. The blood glucose sensors 108 may measure blood glucose levels directly or indirectly. The use of multiple blood glucose sensors 108 facilitates detection of errors or malfunctions, but multiple blood glucose sensors are not required. Other error checking means may be employed, alone or in combination with multiple glucose sensors, such as error detection routines stored in a memory, such as the memory 124, and executed by a processor, such as the processor 122.

The communication system 110 sends data signals and optionally sends and receives data, control and power signals and may comprise bus systems, connectors, switches, wires, multiple antennas, multiple antenna arms, and parasitic elements, instead of or in addition to the illustrated antenna 112. Various data transmission methods and protocols may be employed, such as, for example, serial bus signals, parallel bus signals, radio-frequency signals, infrared signals, amplitude modulation protocols, and frequency modulation protocols. The power system 114 provides power to the blood glucose sensor system 102 and may be configured to provide power in a passive and/or an active manner. The data system 120 is configured to generate output and/or control signals in response to signals received from the blood glucose sensors 108 and/or the communication system 110. In some embodiments, the data system 120 may comprise discrete circuitry in addition to, or instead of, the illustrated processor 122 and/or the memory 124.

The insulin dispenser 104 is a device that dispenses insulin. The insulin dispenser 104 may operate with, or without, user interaction. The insulin dispenser 104 may be configured to supply insulin in a variety of ways, such as, for example, through an IV drip, through subcutaneous or intramuscular injection, through a pen-dispensing device, or through an inhaler.

The insulin dispenser 104 as illustrated comprises an insulin pump 126, an insulin reservoir 128, a communication system 130, which as illustrated comprises an antenna 132, an optional power system 134, which as illustrated comprises an optional rectifier 136 and an optional battery 138, and a control system 140, which as illustrated comprises a processor 142 and a memory 144.

The communication system 130 sends and receives data, control and power signals and may comprise bus systems, connectors, wires, switches, multiple antennas, multiple antenna arms, and parasitic elements, instead of or in addition to the illustrated antenna 132. Various data transmission methods and protocols may be employed, such as, for example, serial bus signals, parallel bus signals, radio-frequency signals, infrared signals, amplitude modulation protocols, and frequency modulation protocols. The power system 134 provides power to the insulin dispenser 104 and may be configured to provide power in a passive and/or an active manner. The control system 140 is configured to generate control and/or output signals in response to signals received from the blood glucose sensor system 102 and/or the blood glucose controller 106 via the communication system 130. In some embodiments, the control system 140 may comprise discrete circuitry in addition to, or instead of, the illustrated processor 142 and/or the memory 144.

The blood glucose controller 106 as illustrated comprises a communication system 146, which as illustrated comprises an antenna 148 and a transceiver 150, a power system 152, and a control system 154, which as illustrated comprises a processor 156, a memory 158, a user interface controller 160, an input device 162, an output device 164, a blood glucose analyzer 166, and discrete circuitry 168.

The communication system 146 sends and receives data and control signals and may comprise bus systems, connectors, wires, switches, multiple antennas, multiple antenna arms, and parasitic elements, instead of or in addition to the illustrated antenna 148 and transceiver 150. The transceiver 150 transmits and receives control and/or data signals. For example, the transceiver 150 may transmit control signals to the blood glucose sensor system 102 and/or the insulin dispenser 104, and may receive data signals from the blood glucose sensor system 102 and/or the insulin dispenser 104.

The power system 152 provides power to the blood glucose controller 106. The user interface controller 160 controls the receipt of user input, which may be received from any suitable user interface, such as the input device 162, which may comprise, for example, a keypad, or from a remote device, such as the insulin dispenser 104 via the communication system 146. User input data may include indications of, for example, the weight of an individual, an individual's body mass index, the medical condition of an individual, an individual's insulin sensitivity, an individual's average daily insulin dose, a meal estimate, a carbohydrate estimate for a meal, changes in an individual's physical activity, changes in an individual's emotional state, prior insulin doses, the time of day, and other information and factors pertinent to control of an individual's blood glucose level.

The user interface controller 160 also controls the output of information, such as a warning signal or the display of information entered by a user, which may be communicated to a user through any suitable user interface, such as the user output device 164, which may comprise, for example, a visual display, an audio system, and/or a printer.

The blood glucose analyzer 166 analyzes data inputs and outputs, and histories of data inputs and outputs, and generates control signals to control the blood glucose controller 106 so as to facilitate control of the operation of the insulin dispenser 104 and/or to generate appropriate warning signals. For example, the blood glucose analyzer 166 may use data received from the blood glucose sensor system 102 to determine a current blood glucose level, an indication of a rate of change of the blood glucose level (e.g., a first time derivative), and/or an indication of an acceleration of the blood glucose level (e.g., a second time derivative). In another example, the blood glucose analyzer 166 may determine an active insulin level based on a history of insulin doses over a period of time and a projection of the reduction in insulin activity for each dose in the history period based on the time that has elapsed since the dose was administered. In another example, a long-term history of blood glucose levels and insulin doses, alone or together with a history of user inputs, may be used by the blood glucose analyzer 166 to predict future blood glucose levels and to generate control signals to control the blood glucose controller 106 so as to control the operation of the insulin dispenser 104.

In some embodiments, the control system 154 may comprise discrete circuitry 168 in addition to, or instead of, the illustrated processor 156, the memory 158, the user interface controller 160, and the blood glucose analyzer 166. In the illustrated embodiment, the blood glucose sensor system 102, the insulin dispenser 104 and the blood glucose controller 106 are communicatively coupled together through radio-frequency signals 170, 172, 174, 176. In other embodiments, the blood glucose sensor system 102, the insulin dispenser 104 and the blood glucose controller 106 may be communicative coupled together through other suitable means, such as a bus system, or through combinations of means.

In one example mode of operation, the blood glucose controller 106 queries (e.g., interrogates) one or more blood glucose sensor systems, such as blood glucose sensor system 102, with a wireless signal, such as an electromagnetic signal. The blood glucose controller 106 may be, for example, configured to periodically interrogate one or more blood glucose sensor systems, to interrogate one or more blood glucose sensor systems in response to user input or a control signal, or various combinations thereof. In the embodiment as illustrated, the blood glucose controller 106 broadcasts an RF interrogation signal 170. The RF interrogation signal 170 may be modulated to carry data, instructions or commands. For example, the RF interrogation signal 170 may be modulated to carry a command directing the blood glucose sensor system 102 to return a signal indicative of a blood glucose level. The blood glucose sensor system 102 may extract power from the interrogation signal 170. The blood glucose sensor system 102 may extract power from the battery 118. In response to the interrogation signal 170, the blood glucose sensor system 102 may respond to the interrogation signal 170 with a response signal. As illustrated in FIG. 1, the blood glucose sensor system 102 responds to the interrogation signal 170 with a response signal 174. The response signal 174 may be, for example, a modulation backscatter signal conveying information indicative of a blood glucose level at a sample time period.

The blood glucose controller 106 receives the response signal 174 and extracts the information in the response signal 174 indicative of a blood glucose level. The blood glucose controller 106 may also receive user input. In response to the response signal 174, prior response signals, and/or any user input, the blood glucose controller 106 may generate one or more control signals to control the insulin dispenser 104. As illustrated in FIG. 1, the blood glucose controller 106 selectively transmits a radio-frequency control signal 172 to the insulin dispenser 104. In response to the control signal 172, the insulin dispenser 104 may dispense a specified amount of insulin at a specified rate. The insulin dispenser 104 may extract power from the control signal 172 and/or from the battery 138. The insulin dispenser 104 may transmit one or more signals 176 to the blood glucose controller 106, such as a signal confirming that a specified amount of insulin has been dispensed at the specified rate.

In another example mode of operation, the blood glucose sensor system 102 is configured to periodically transmit data, such as data embedded in the illustrated radio-frequency signal 174, and the blood glucose controller 106 is configured to receive the data, for example by extracting the data from the radio-frequency signal 174, and to generate and transmit a control signal to control operation of the insulin dispenser 104.

The data system 120 and the control systems 140, 154 may be implemented in a variety of ways, including as a combined control system or as separate subsystems. The data system 120 and the control systems 140, 154 may be implemented as one or more microprocessors, digital signal processors (DSP), application-specific integrated circuits (ASIC), or the like, or as a series of instructions stored in a memory, such as the memories 124, 144, 158, and executed by a controller, such as the processors 122, 142, 156, or various combinations of the above. Thus, software modifications to existing hardware may allow the implementation of the dispenser control system 100. Various subsystems, such as the blood glucose analyzer 166, are identified as separate blocks in the functional block diagram of FIG. 1 because they perform specific functions that will be described in more detail below. These subsystems may be discrete units. For example, the data system 120 may be implemented with a discrete circuit. The subsystems also may not be discrete units but may be functions of a software routine, which will probably, but not necessarily, be separately callable and identifiable elements. The various subsystems may be combined. For example, all or portions of the blood glucose analyzer 166 may be integrated into the user interface controller 160. In another example, the blood glucose controller 106 may be combined with the insulin dispenser 104. In another example, the blood glucose sensor system 102, the insulin dispenser 104 and the blood glucose controller 106 may be combined.

While the illustrated embodiment denotes a single processor 156 in the blood glucose controller 106, other embodiments may comprise multiple processors. Similarly, the illustrated embodiment shows three processors 122, 142, 156 in the dispenser control system 100, a single processor could be used on some embodiments. The memories 124, 144, 158 may comprise, for example, registers, read only memory ("ROM"), random access memory ("RAM"), flash memory and/or electronically erasable programmable read only memory ("EEPROM"), and may provide instructions and data for use by the data system 120 and/or the control systems 140, 154.

Figure 2:
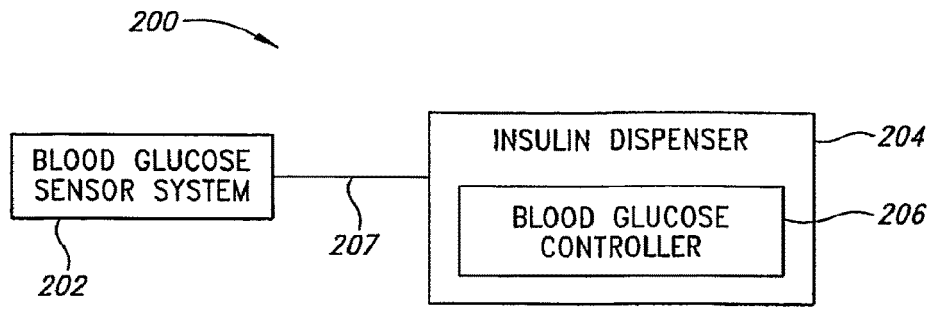
FIG. 2 is functional block diagram of another embodiment of dispenser control system.

FIG. 2 is a functional block diagram of another embodiment of a dispenser control system 200. The dispenser control system 200 comprises a blood glucose sensor system 202 and an insulin dispenser 204 comprising a blood glucose controller 206. Details of the blood glucose sensor system 202, the insulin dispenser 204 and the blood glucose controller 206 are omitted from FIG. 2 for ease of illustration. The blood glucose sensor system 202 is communicatively coupled to the insulin dispenser 204 through communication link 207. The communication link 207 may comprise, for example, radio-frequency communication links, a bus system, one or more wires, an infrared communication link or combinations of various communication links.

Figure 3:
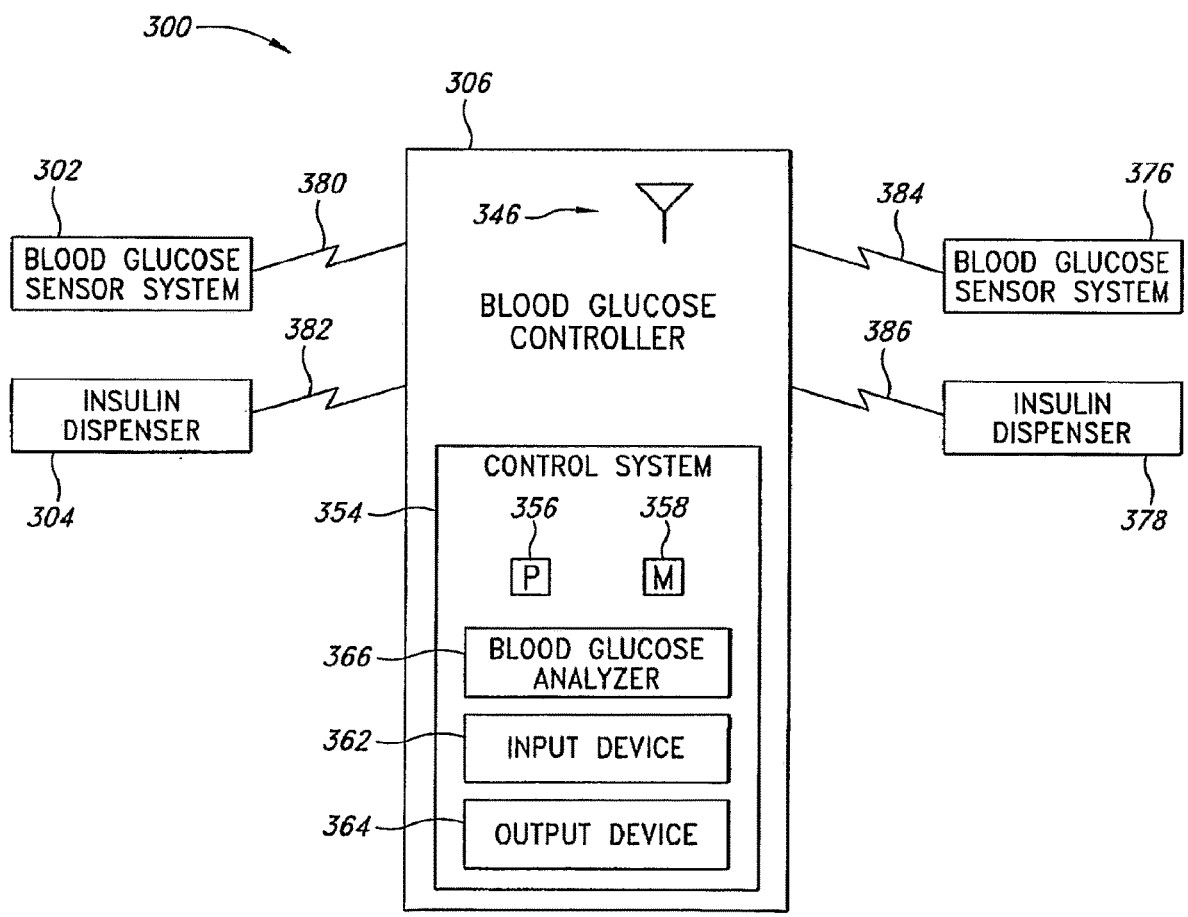
FIG. 3 is a functional block diagram of another embodiment of a dispenser control system.

FIG. 3 is a functional block diagram of another embodiment of a dispenser control system 300. The dispenser control system 300 comprises a plurality of blood glucose sensor systems 302, 376, a plurality of blood glucose dispensers 304, 378, and a blood glucose controller 306. The components of the dispenser control system 300 are communicatively linked together through communication links 380, 382, 384, 386, which may comprise, for example, radio-frequency communication links, a bus system, one or more wires, an infrared communication link, or combinations of various communication links. The blood glucose controller 306 comprises a control system 354, which as illustrated comprises a processor 356, a memory 358, a blood glucose analyzer 366, an input device 362 and an output device 364. The input device 362 accepts user input, such as data related to carbohydrate consumption or other information regarding an individual, and the output device 364 provides information to the user, such as warnings, confirmation of user input data, current and historical blood glucose levels, operational modes or presumptions (e.g., an indication the dispenser control system 300 is in a regressive carbohydrate reduction mode or an indication the dispenser control system 300 has determined a monitored individual is sleeping) or recommendations (e.g., a recommendation to postpone a meal or to limit a meal's carbohydrate content). The embodiment illustrated in FIG. 3 may be advantageously employed to monitor and control the blood glucose and/or active insulin levels in multiple individuals.

Figure 4:
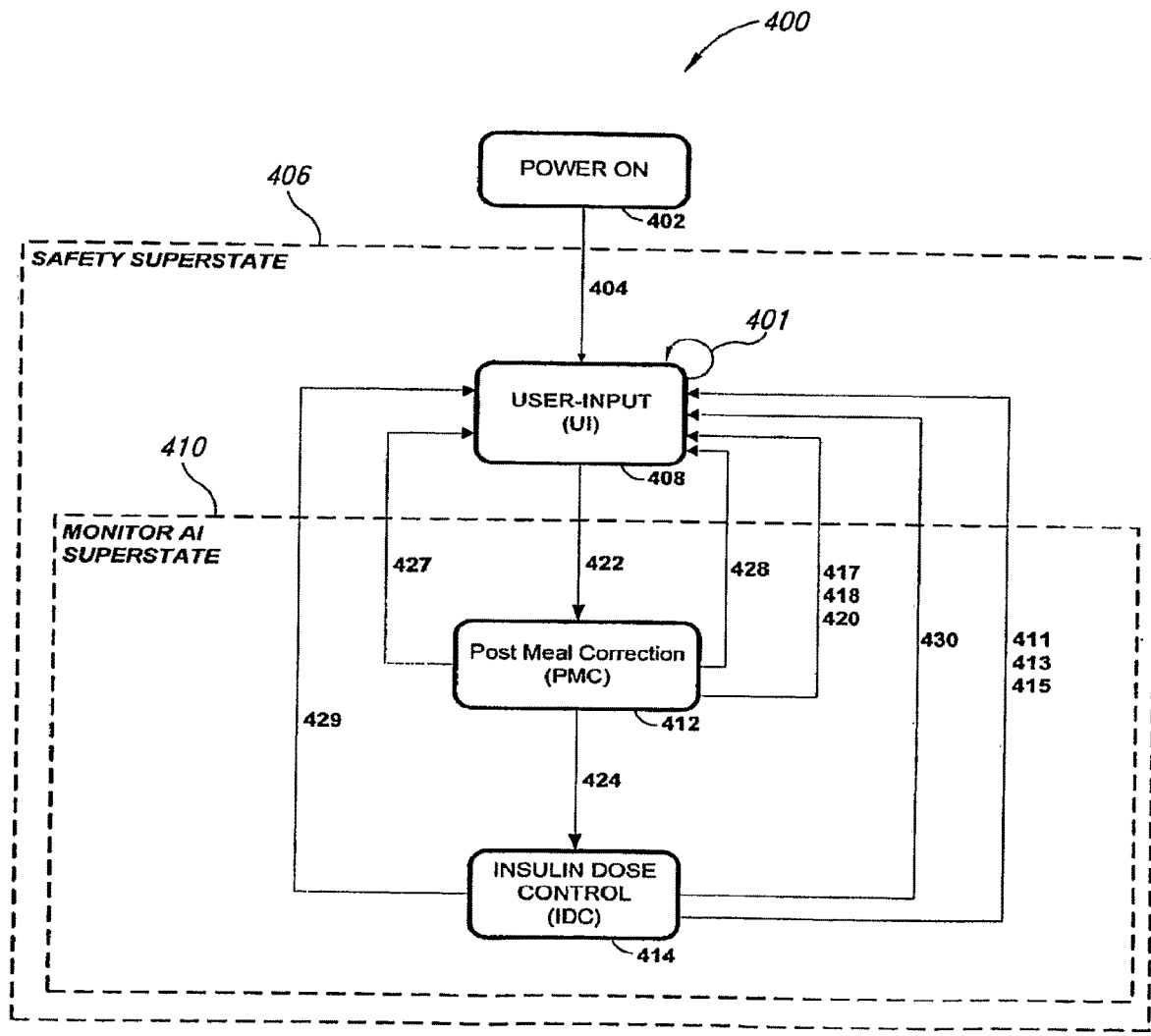
FIG. 4 is high-level hierarchical state diagram for an embodiment of a method of operating a dispenser control system.

FIG. 4 is a high-level hierarchical state diagram 400 illustrating an example method of an embodiment of controlling a dispenser control system, such as the dispenser control systems 100, 200, 300 illustrated in FIGS. 1-3. For convenience, the state diagram 400 will be described with reference to the dispenser control system 100 illustrated in FIG. 1. The dispenser control system 100 is initiated at initiation state 402. A user may typically initiate the dispenser control system 100 just prior to consumption of a meal or when it is desirable to enter information regarding an individual.

The dispenser control system 100 transitions 404 from initiation state 402 to a safety super-state 406 and enters a wait-for-user-input state 408.

While in the safety super-state 406, the dispenser control system 100 determines whether data generated or received by dispenser control system 100 indicates that a dangerous condition exists. When the dispenser control system 100 determines in the safety super state 406 that a dangerous condition exits, the dispenser control system 100 may be configured to generate control signals to activate an alarm (e.g., a visual alarm, an audio alarm, a vibration alarm, a remote alarm, and/or combinations of the above), which may vary based on the nature of the dangerous condition and/or the operational state of the dispenser control system, and to cause the dispenser control system 100 to transition to the wait-for-user-input state 408. For example, when the dispenser control system 100 determines that an individual is sleeping and that a dangerous condition has arisen, the dispenser control system may be configured to sound an alarm loud enough to wake the individual. The dispenser control system 100 may be configured to determine that a dangerous condition exists in response to, for example: an indication that a monitored blood glucose level is below or above threshold levels; an indication that a predicted blood glucose level will be below or above threshold levels; an indication of an equipment failure; or an indication of improbable blood glucose levels for an individual (for example, blood glucose levels inconsistent with an individual's history or historical glycemic profile, or with data received regarding an individual, such as an indication of when a meal was consumed or a carbohydrate ratio of a meal).

In the illustrated state diagram 400, the dispenser control system 100 also is configured to determine whether a dangerous condition exists by monitoring the active insulin level in the monitor active insulin (AI) super-state 410, as discussed in more detail below. When the dispenser control system 100 determines in the monitor active insulin super state 410 that a dangerous condition exits based on the monitoring of the active insulin level, the dispenser control system 100 is configured to generate control signals to active an alarm and to limit insulin infusion, and to transition to the wait-for-user-input state 408.

The threshold levels and ranges may be fixed or may be functions and may be based on statistical analysis. For example, an indication of a blood glucose level below a threshold level of 80 mg/dl may cause the dispenser control system 100 to determine that a dangerous condition exists. In another example, an active insulin level above a threshold level of 20 International Units (hereinafter insulin units) may cause the dispenser control system 100 to determine in the monitor active insulin super state 410 that a dangerous condition exists. An active insulin level may be determined based on a history of doses over a selected time period, with the impact of each dose adjusted using a form factor indicative of the reduced insulin activity due to the time elapsed since the dose was given. A threshold active insulin maximum level may be fixed or a function, and may be set using an adjustable input parameter. Similarly, the determination of whether a blood glucose level is improbable may be based on thresholds, functions and statistical analysis. Look-up tables, fuzzy logic and/or neural networks may be employed, for example. Indications of equipment failure may include direct indications (for example, an error signal from the insulin dispenser 104), or indirect indications (for example, inconsistent indications of blood glucose levels from multiple blood glucose sensors 108 in a blood glucose sensor system 102, or an indication that a pump is not operating properly, such as an indication an insulin dispenser 104 is not responding to a control signal).

In the state diagram illustrated in FIG. 4, when the dispenser control system 100 determines that a dangerous condition exists, the dispenser control system 100 may be configured to trigger an alarm (such as an alarm by the user output 164 and/or a remote alarm) and to enter the wait-for-user-input state 408.

The dispenser control system 100 is configured to enter the wait-for-user-input state 408 when the dispenser control system 100 is initiated, when invoked by the user (for example, when the user wishes to enter information such as information regarding a meal), which may be at the same time as initiation, or in response to a dangerous condition or an anomaly being detected. In the wait-for-user-input state 408, the dispenser control system 100 is configured to wait for user input. The dispenser control system 100 may be configured to prompt the user for input, and may be configured to signal an alarm. For example, when the wait-for-user-input state 408 is entered from the safety super-state 406 or the monitor AI super state 410, the dispenser control system 100 may be configured to signal an alarm. The dispenser control system 100 may be configured to time-out if no user input is received within a threshold period of time. For example, when the wait-for-user-input state 408 is entered from initiation state 402, the dispenser control system 100 may be configured to wait for a threshold period of time for input from a user, and then transition to another state such as the Post Meal Correction state 412 or the insulin dose control state 414 if certain conditions are satisfied, as discussed in more detail below. The dispenser control system 100 may be configured to respond to direct commands to dispense particular amounts of insulin, and may be further configured to require confirmation if a commanded dose is inconsistent with an actual or predicted blood glucose level or an active insulin level. For example, the dispenser control system 100 may be configured to return 401 to the user-input state 408 in response to a command that is inconsistent with data.

The user input may include information regarding a meal about to be consumed, a meal recently consumed, or information about an individual, as discussed above. When the information includes information regarding a meal that is about to be consumed, the dispenser control system 100 may be configured to generate control signals to cause the insulin dispenser 104 to dispense a bolus dose (or a pre-meal dose) of insulin. The bolus dose may be calculated using known methods using factors that may include, for example, insulin sensitivity and a carbohydrate ratio. The dispenser control system 100 may also be configured to generate control signals to cause the insulin dispenser 104 to dispense insulin doses during a fasting period.

The dispenser control system 100 may be configured to transition 422 from the wait-for-user-input state 408 to the Post Meal Correction state 412 when it is determined that sufficient time, for example T_threshold, has passed since insulin has been infused, and the blood glucose level is or predicted to be within the threshold range for post meal corrections to begin. The actual blood glucose threshold range for transitioning from the wait-for-user-input state 408 to the Post Meal Correction state 412 may be determined by an event that initiated the wait-for-user-input state. Threshold values for instances of the wait-for-user-input state that are initiated by carbohydrate entries are lower than instances of the state initiated by a meal signal only. Instances of the wait-for-user-input state that that are initiated by user-initiated boluses may have lower threshold values than instances initiated by meal only signals. These three threshold values may be physician-set during the patient's enrollment process. See Table 3. The more the patient complies with intensive insulin therapy, the lower the threshold values.

The more information that a user, such as a patient, tells the system about a meal, for example, the lower the blood sugar targets that may be set. For example, if the patient estimates the meal carbs, the blood sugar target may be lower than if the patient only signals the meal, which may be lower than if the patient provides no information at all about the meal. The blood sugar targets are typically on a per meal basis, which means if a normally compliant patient estimates the carbs of their breakfast meal but forgets to estimate or signal their dinner meal, the blood sugar target for dinner is higher than breakfast. This same concept can be applied to non-meal or fasting periods.

As illustrated, the wait-for-user-input state 408 is within the safety super state 406. Thus, the dispenser control system 100 will not transition from the wait-for-user input state 408 to another state if a dangerous condition exists, and if it is determined that a dangerous condition has developed while the dispenser control system 100 is in the wait-for-user-input state 408, the dispenser control system 100 may be configured to generate control signals to activate an alarm.

In the Post Meal Correction state 412, the dispenser control system 100 is configured to periodically determine whether an additional bolus dose should be provided, or whether the conditions are such that the dispenser control system 100 should transition 424 to the insulin dose control state 414. For example, if an acceleration of blood glucose level indicates an insufficient bolus dose was provided, the dispenser control system 100 may be configured to dispense an additional bolus dose.

The dispenser control system 100 may be configured to transition 424 from the Post Meal Correction state 412 to the insulin dose control state 414 when threshold safety conditions are satisfied. For example, if the history is consistent with a sufficient post-prandial period, the blood glucose level is or is predicted to be within a safe threshold range (e.g., between 90 and 140 mg/dl), and the active insulin level is below a threshold (e.g., 20 insulin units).

As illustrated, the Post Meal Correction state 412 is within the safety super state 406 and the monitor active insulin super state 410. The dispenser control system 100 is configured to activate an alarm and transition 428 from the Post Meal Correction state 412 to the wait-for-user-input state 408 when it is determined that a dangerous condition exists. For example, if the blood glucose level is or is predicted to be outside of a threshold range (e.g., between 90 and 140 mg/dl), and the active insulin level is or is predicted to be above a threshold (e.g., 20 insulin units). Further, if the determination that a dangerous condition exists is based in part on a determination that an active insulin level exceeds a threshold level, the dispenser control system 100 may be configured to limit insulin infusion. For example, the dispenser control system 100 may limit insulin infusion to a threshold amount for a threshold period of time. The dispenser control system 100 may be configured to transition 417 from the Post Meal Correction state 412 to the wait-for-user-input state 408 in response to commands received by the dispenser control system 100 (e.g., a command entered by a user, for example, an indication that a meal is about to be consumed without entering the estimated carbs for that meal.) The dispenser control system 100 may be configured to transition 418 from the Post Meal Correction state 412 to the wait-for-user-input state 408 in response to commands received by the dispenser control system 100 (e.g., a command entered by a user, for example, an indication that a meal is about to be consumed by entering the estimated carbs for that meal.) The dispenser control system 100 may be configured to transition 420 from the Post Meal Correction state 412 to the wait-for-user-input state 408 in response to commands received by the dispenser control system 100 (e.g., a command entered by a user, for example, an indication that a user-initiated manual correction bolus was entered.)

The dispenser control system 100 may be configured to transition 424 from the Post Meal Correction state 412 to the insulin dose control state 414 when it is determined that sufficient time has passed since post meal corrective doses have been infused, and the blood glucose level is or is predicted to be within the threshold range for fully automatic insulin dosing control to begin. The actual threshold range for transitioning from the Post Meal Correction state 412 to the insulin dose control state 414 may be determined by an event that initiated the Post Meal Correction state. For example, to the extent the patient complies with intensive insulin therapy, lower threshold values may be employed.

The dispenser control system 100 may be configured in the insulin dose control state 414 to monitor blood glucose levels and to periodically dispense insulin based on the current blood glucose level and the history of the monitored blood glucose levels. The dispenser control system 100 may be configured to dispense insulin based on other information about an individual, as discussed above. The dispenser control system 100 may employ, for example, fuzzy logic, a neural network, a look-up table, software routines or combinations thereof to periodically dispense insulin based on the history of the monitored blood glucose levels and other information.

Table 1 illustrates an example fuzzy logic Dosing Rules Matrix that may be applied by the dispenser control system 100 to control the dispensing of subcutaneous insulin while in the insulin dose control state. The dosing identifiers in Table 1 represent experimentally distinct doses of insulin, which may be measured in Units of Insulin. The dosing identifiers from largest dose to smallest dose are D90 (very large) to D01 (very small). The first fuzzy input is the current blood glucose level BGL in mg/dl units, represented in the bottom four rows with fuzzy coverings BV (very high), BH (high), BM (medium), and BN (normal). The second fuzzy input is the rate of change of the blood glucose level, represented in row BGL RATE with fuzzy coverings RN (negative), RZ (zero), RP (positive) and RV very positive. The third fuzzy variable is acceleration of the blood glucose level, represented in row BGL Acceleration with fuzzy coverings AN (negative), AZ (zero) and AP (positive). Example trajectories corresponding to the blood glucose level rate of change and acceleration are illustrated in row BGL Trajectory. The fuzzy coverings may be experimentally determined, and may vary based on additional factors such as the method of delivering a dose of insulin.

TABLE 1

EXAMPLE DOSING RULES MATRIX

| BGL Rate: | | RN | | | RZ | | | RP | | | RV | | |
|---|---|---|---|---|---|---|---|---|---|---|---|---|---|
| BGL Acceleration: | | AN | AZ | AP | AN | AZ | AP | AN | AZ | AP | AN | AZ | AP |
| BGL Trajectory: | | ↘ | ↘ | ↘ | ↗ | → | ↘ | ↗ | → | → | ↗ | ↗ | ↗ |
| BGL | BV | D01 | D10 | D70 | D01 | D20 | D80 | D01 | D80 | D80 | D01 | D90 | D90 |
| | BH | D01 | D10 | D20 | D01 | D20 | D50 | D01 | D80 | D80 | D01 | D90 | D90 |
| | BM | D01 | D05 | D10 | D01 | D10 | D20 | D01 | D40 | D40 | D01 | D80 | D90 |
| | BN | D01 | D05 | D01 | D01 | D02 | D05 | D01 | D05 | D10 | D01 | D05 | D10 |

The dispenser control system 100 may be configured to transition 411 from the insulin dose control state 414 to the wait-for-user-input state 408 in response to commands received by the dispenser control system 100 (e.g., a command entered by a user, for example, an indication that a meal is about to be consumed without entering the estimated carbs for that meal.) The dispenser control system 100 may be configured to transition 413 from the insulin dose control state 414 to the wait-for-user-input state 408 in response to commands received by the dispenser control system 100 (e.g., a command entered by a user, for example, an indication that a meal is about to be consumed by entering the estimated carbs for that meal.) The dispenser control system 100 may be configured to transition 415 from the insulin dose control state 414 to the wait-for-user-input state 408 in response to commands received by the dispenser control system 100 (e.g., a command entered by a user, for example, an indication that a user-initiated manual correction bolus was entered.)

As illustrated, the insulin dose control state 414 is within the safety super state 406 and the monitor active insulin super state 410. The dispenser control system 100 is configured to activate an alarm and transition 430 from the insulin dose control state 414 to the wait-for-user-input state 408 when it is determined that a dangerous condition exists. For example, if the blood glucose level is or is predicted to be outside of a threshold range (e.g., between 90 and 140 mg/dl), and the active insulin level is or is predicted to be above a threshold (e.g., 20 insulin units). Further, if the determination that a dangerous condition exists is based in part on a determination that an active insulin level exceeds a threshold level, the dispenser control system 100 may be configured to limit insulin infusion. For example, the dispenser control system 100 may limit insulin infusion to a threshold amount for a threshold period of time.

Embodiments of the method of operating a dispenser control system illustrated by the hierarchical state diagram 400 of FIG. 4 may not contain all of the illustrated states, superstates and transitions, may contain additional states, superstates and transitions, or may combine or separate illustrated states and superstates. For example, the Post Meal Correction state 412 and the insulin dose control state 414 may be combined into an automatic dose control state in some embodiments. The threshold levels and ranges discussed with respect to FIG. 4 may be fixed or may be functions and may be based on statistical analysis.

An example embodiment of an IDC method and its application is provided in Example 1.

Personalization

Insulin dosing may be adjusted to be appropriate for a particular patient, or personalized. For example, the details of a basic IDC design may be set as if they applied to a nominal or standard patient, with a capability to adjust one or more parameters of that design for each particular patient.

An example of a personalization parameter is an overall multiplier of the IDC dose listed as Mult_per in an enrollment table. An example IDC method is designed to be appropriate for an active 20-year-old male of 75 kg weight, with an average daily dose of insulin of 49.9 units. For that patient no adjustment is necessary and the Mult_per is 1.0. Three example methods for choosing an adjusted value of Mult_per for a patient are given.

The first example method is to determine Mult_per by the patient's weight. For example:

Mult_per=weight/75, where the weight is given in kgs.

A second example method is to use the average daily insulin dose of the patient recorded over the previous week. A patient starting use of an ICD controlled insulin pump may already have experience with a manually controlled insulin pump which records the total of the insulin doses received each day. Those totals, averaged over a week, are compared to the standard patient's average daily dose to yield the multiplier. For example:

Mult_per=(TDD for new patient)/(TDD for standard patient) which, for the example standard patient is:

Multi_per=(TDD for new patient)/(49.9 units).

The third example method may be called the ABCD method, where "A," "B," "C" and "D" characterize the blood sugar vs. time graph resulting from the standard patient's response to consuming a particular amount of carbohydrate normalized by body weight.

The "A" term represents the maximum peak blood sugar; "B" is the time required to reach the maximum; "C" represents the "A" value minus the steady state blood sugar recorded after consuming the carbohydrate, and "D" is the time required to achieve the steady state blood sugar. In this example method the particular patient consumes the same amount of carbohydrate, normalized to their body weight and their deltas to the standard patient ABCD values are recorded. The particular Mult_per for a patient may be determined, for example, on a case by case basis by a physician's analysis of the ABCD deltas.

From time to time there may be a need to change Mult_per if the patient has a significant change in health status or activity level. Examples are: change from sedentary to active life style or vice versa, entrance into puberty, entrance into menopause or a large change in weight.

Embodiments of the state diagram illustrated in FIG. 4 may contain additional states not shown in FIG. 4, may not contain all of the states illustrated in FIG. 4, may contain additional transitions not illustrated in FIG. 4, may not contain all of the transitions illustrated in FIG. 4, and may combine or separate states illustrated in FIG. 4. For example, the dispenser control system 100 may be configured to set an alarm and transition to the user-input state 408 whenever an error is detected, such as an equipment malfunction, or if unsafe blood glucose levels are detected or predicted (e.g., blood glucose levels outside a threshold range, or blood glucose levels above a threshold in combination with a rate of increase in the blood glucose level that is above a threshold rate of increase, or blood glucose level that is predicted to be unsafe using statistical methods, such as those described herein). The threshold levels and ranges discussed with respect to FIG. 4 may be fixed or may be functions and may be based on statistical analysis.

Figure 5A:
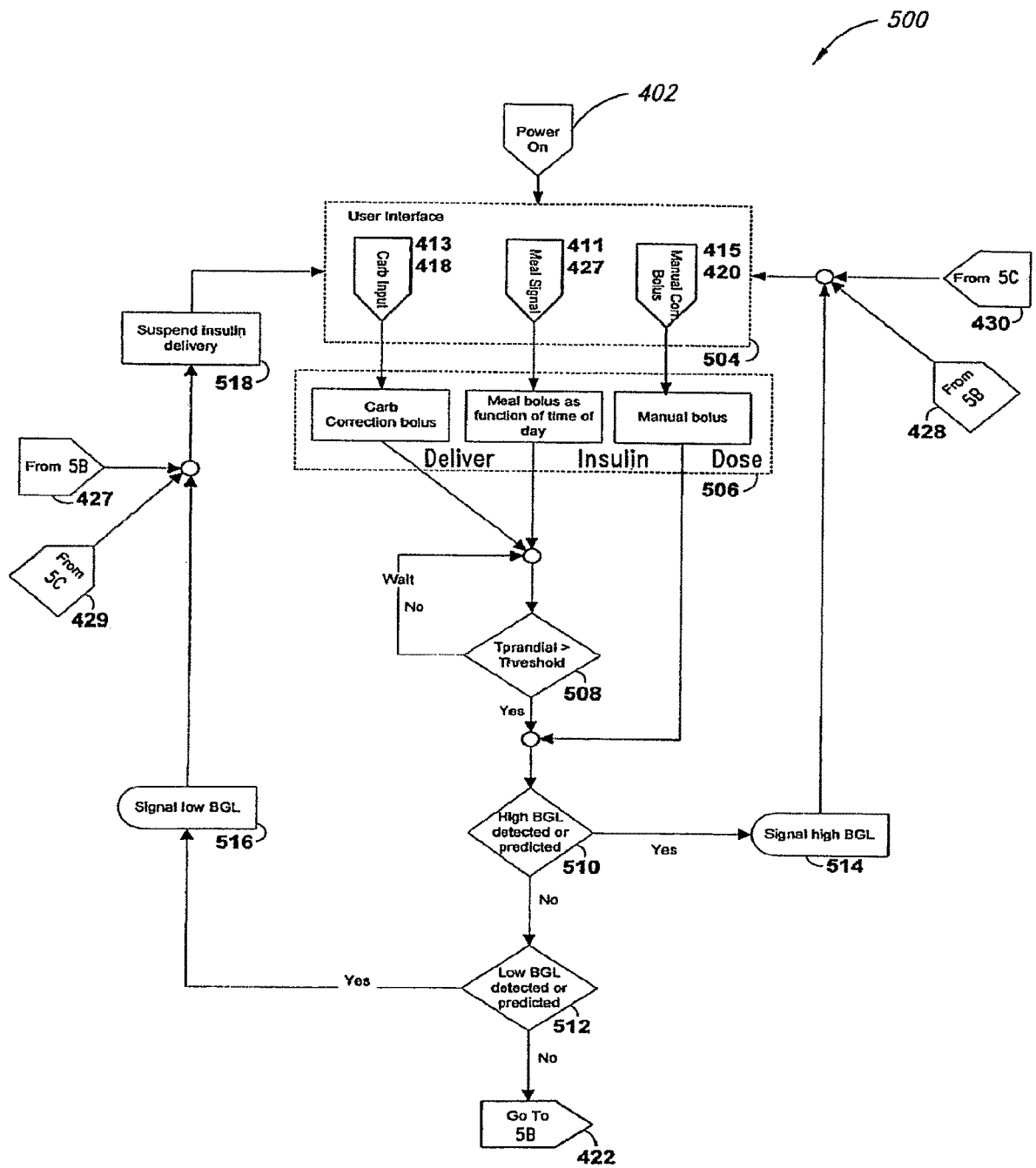
FIGS. 5A through 5C are a mid-level flow diagram for an embodiment of a method of operating a dispenser control system.
Figure 5B:
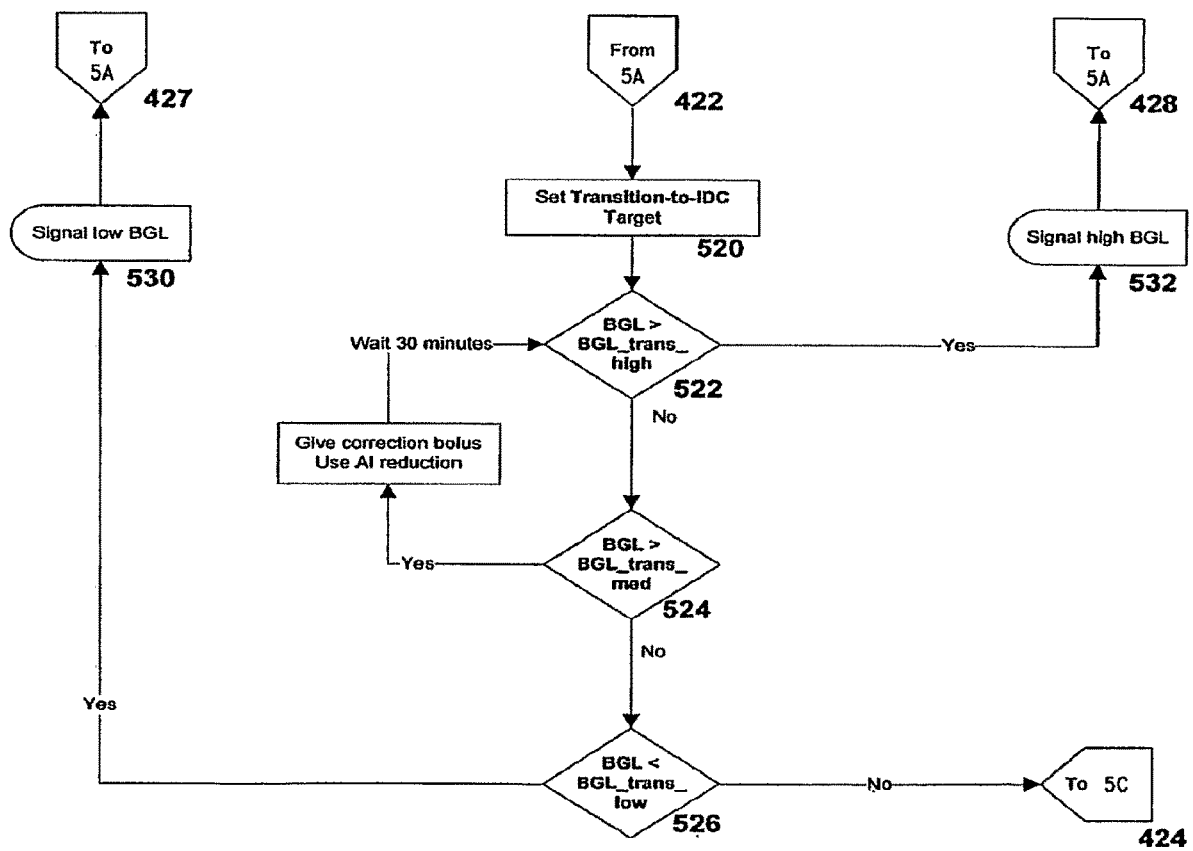
Figure 5C:
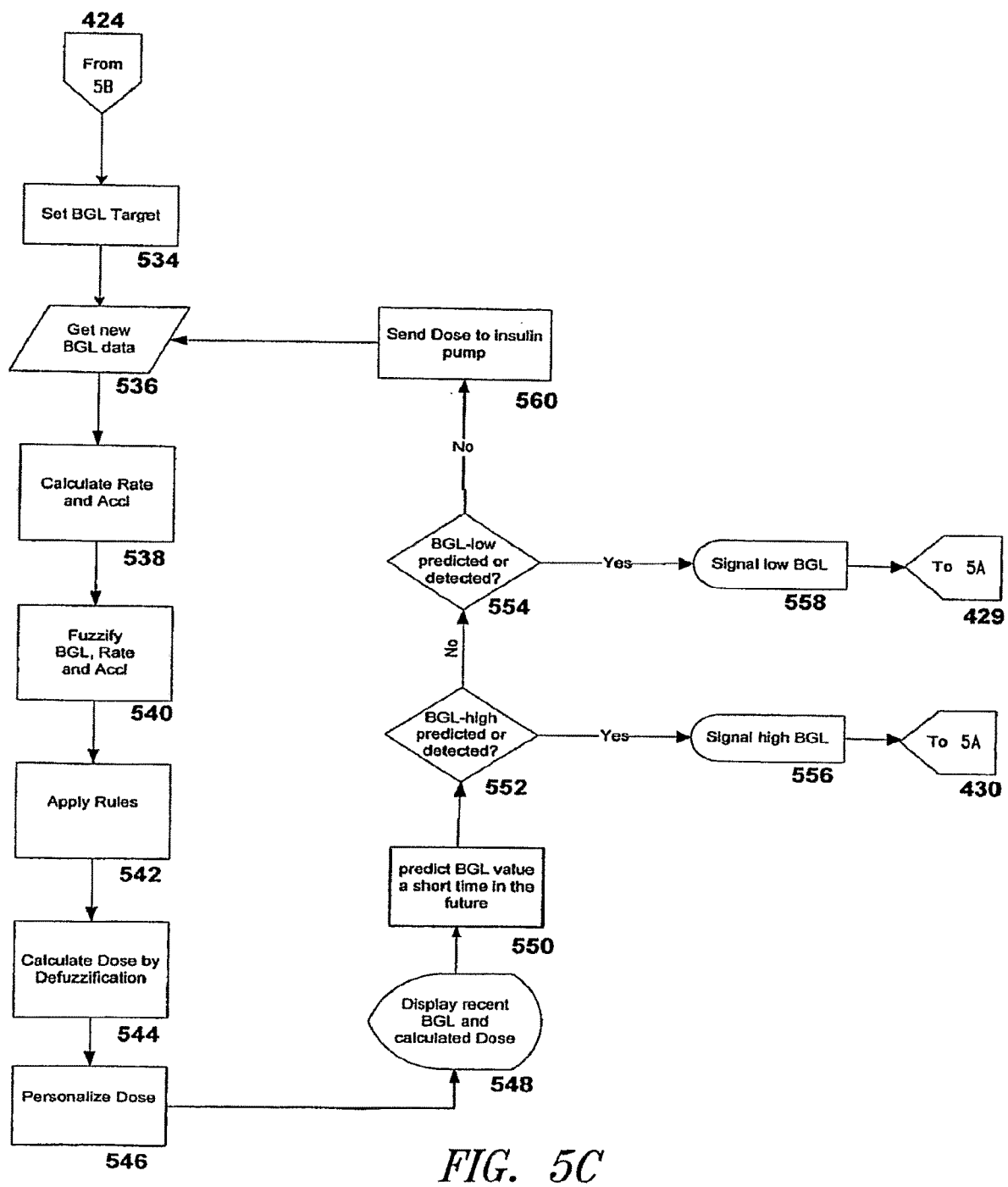

FIGS. 5A through 5C illustrate a mid-level flow diagram of an embodiment of a method 500 that may be employed by a dispenser control system, such as the dispenser control systems 100, 200 and 300 illustrated in FIGS. 1 through 3, to control the dispensing of insulin. For convenience, the method will be described with respect to the embodiment of a dispenser control system 100 illustrated in FIG. 1.

The dispenser control system 100 initializes the method 500 at 402. The method 500 proceeds from 402 to 504. At 504, the dispenser control system 100 requests user input and optionally provides information to the user.

At 504, the dispenser control system 100 determines whether there is an indication of user input. For example, the user may enter data indicating a prandial event is about to occur, with or without an indication of a carbohydrate content of the meal, or may enter data indicating a BGL correction bolus. In the case of a compliant patient the insulin dose may be calculated 413 as Carb_compliant*Carb_bolus_factor. In the case of a semi-compliant patient the insulin dose may be calculated 411 based on which time window is active (T_breakfast, T_lunch, T_dinner or T_other) and the corresponding assumed carb (Carb_breakfast, Carb_lunch, Carb_dinner, Carb_other). In the case of a manual correction the insulin dose may be calculated 415, for example, by (BGL_current−BGL_correction)*BGL_corr_factor or by a direct insulin dose entry. The method then proceeds from 504 to 506.

At 506, the dispensing control system 100 instructs the insulin pump to deliver the insulin dose calculated in 504. The method proceeds from 506 to 508 in the case of a meal indication or 510 in the case of a manual correction.

At 508, the dispenser control system 100 determines whether sufficient time has elapsed since the postprandial infusion event. The dispenser control system 100 may determine whether sufficient time has elapsed by, for example, comparing the elapsed time T_prandial to a threshold time T_threshold (e.g., 120 minutes). When the dispenser control system 100 determines that a sufficient amount of time has elapsed since the prandial event, the method proceeds from 508 to 510. In some embodiments, high BGL readings may be ignored during this time.

At 510, the dispensing control system 100 determines whether a dangerously high blood glucose condition exists or is predicted. The dispensing control system 100 may, for example, determine that a dangerously high blood glucose condition exists if an indication of a current blood glucose level exceeds a threshold amount BGL_high (e.g., 180 mg/dl) and a rate of change of the blood glucose level exceeds a threshold rate of change (e.g., an increase of 50 mg/dl over fifteen minutes). The dispensing control system 100 may, for example, determine by statistical methods, such as those described herein, that a dangerously high blood glucose condition is predicted to exceed a threshold. When the dispensing control system 100 determines that a dangerously high blood glucose condition exists, the method proceeds from 510 to 514. At 514, the dispensing control system 100 sets appropriate warning flags. For example, the dispensing control system 100 may set a flag to cause the output device to sound an alarm. The method then proceeds from 514 to 504. When the dispensing control system 100 determines that a dangerously high blood glucose condition does not exist, the method proceeds from 510 to 512.

At 512, the dispensing control system 100 determines whether a dangerously low blood glucose condition exists. The dispensing control system 100 may, for example, determine that a dangerously low blood glucose condition exists if an indication of a current blood glucose level is lower than a threshold amount, BGL_low (e.g., 80 mg/dl) and a rate of change of the blood glucose level falls below a threshold rate of change (e.g., a decrease of 30 mg/dl over fifteen minutes). The dispensing control system 100 may, for example, determine by statistical methods, such as those described herein, that a dangerously low blood glucose condition exceeds or is predicted to exceed a threshold. When the dispensing control system 100 determines that a dangerously low blood glucose condition exists, the method proceeds from 512 to 516. At 516, the dispensing control system 100 sets appropriate warning flags. For example, the dispensing control system 100 may set a flag to cause the output device to sound an alarm and suspend insulin infusion. The method then proceeds from 516 to 504. When the dispensing control system 100 determines that a dangerously low blood glucose condition does not exist, the method 500 transitions via 422 to 520.

At 514, the dispenser control system 100 signals the user that the blood glucose level is too high and transitions to 504.

At 516, the dispenser control system 100 signals the user that the blood glucose level is too low and proceeds from 516 to 518.

At 518, the dispenser control system 100 suspends insulin delivery. The method then proceeds from 518 to 504.

At 520 the PMC state is entered and the target BGL levels to transition to the IDC state are determined or retrieved. The criteria for determining when to transition from PMC to IDC may depend, for example, on how the PMC state was entered. For example, if the PMC state was initiated by a Carb User-Input, then the BGL transition levels (BGL_high_trans, BGL_med_Trans, BGL_low_trans) may be set to a lowest level. This may be viewed as a the compliant control mode. In another example, if the PMC state was initiated by a Meal signal User-Input, then the BGL transition levels (BGL_high_trans, BGL_med_Trans, BGL_low_trans) may be set higher. This may be viewed as a the semi-compliant control mode. In another example, if the PMC state was initiated by a Manual bolus User-Input, or from No patient input, then the BGL transition levels (BGL_high_trans, BGL_med_Trans, BGL_low_trans) may be set to a highest level. This may be viewed as a Non-compliant control mode.

These targets may be set, for example, by a physician during an Enrollment process. See Table 2. The method proceeds to 522.

At 522 the current BGL is compared to the BGL_trans_high level determined or retrieved in 520. If the BGL is above this level the method proceeds to 532. If not the method proceeds to 524.

At 524, the dispensing control system 100 determines whether a post meal correction is desirable, for example, by comparing it to the BGL_med_trans level set in 520. The dispensing control system 100 may, for example, determine that post meal correction is desirable if an indication of a current blood glucose level exceeds a threshold amount BGL_trans_med and a rate of change of the blood glucose level exceeds a threshold rate of change (e.g., an increase of 10 mg/dl over fifteen minutes). When the dispensing control system 100 determines that post meal correction is not necessary, the method proceeds from 524 to 526.

At 526 the current BGL is compared to the BGL_trans_low level set in 520. If the BGL is below this level the method proceeds to 530. If not the method transitions via 424 to 534.

At 530, the dispenser control system 100 signals the user that the blood glucose level is too low and transitions via 427 from 530 to 504.

At 532, the dispenser control system 100 signals the user that the blood glucose level is too high and transitions via 428 to 504.

At 534, the dispensing control system 100 determines or retrieves the target BGL. These may be set based upon the entry condition, for example, to BGL_comp for entry from the compliant mode, to BGL_semi for entry from the semi-compliant mode, and to BGL_non for entry from the non-compliant mode. Also the BGL fuzzy covering may be shifted from the baseline based on the target BGL. BGL_comp, BGL_semi, and BGL_non as well as other items may be constants and may be initialized by the physician according to an enrollment process such as defined below. The method proceeds from 534 to 536. The values may depend on how a PMC state was entered. For example, the IDC target BGL may be set lowest when the PMC state was initiated by a user carbohydrate input, to a higher level when the PMC state was initiated by a meal-signal user input, and to a highest level when the PMC state was initiated by a manual bolus user input or no input.

At 536, the dispensing control system 100 receives a recently measured value of the blood glucose level from the sensor. The measurements may normally be taken at a fixed time interval, but this is not required. The method proceeds from 536 to 538.

At 538, the dispensing control system 100 calculates the rate and acceleration. Bi is the BGL value at the current time Ti. Bi−1 is the BGL value at the previous time Ti−1. The rate, Ri, and the acceleration, Ai, may be calculated as follows: Ri=(Bi−Bi−1)/(Ti−Ti−1). Ai=2 (Ri−Ri−1)/(Ti−Ti−2) (This definition can account for variable time steps.) The method proceeds from 538 to 540.

At 540, the dispensing control system 100 fuzzifies the blood glucose level, the blood glucose rate and the blood glucose acceleration. This may be done, for example, by applying the fuzzy coverings of Table 2 to the values of blood glucose level, blood glucose rate, and blood glucose acceleration. This yields a set of truth-values for the appropriate fuzzy members. The method proceeds from 540 to 542.

At 542, the dispensing control system 100 applies fuzzy logic rules to determine a fuzzy insulin control dose. For example, the dispensing control system 100 may apply the fuzzy logic rules illustrated in Table 1. This yields the fuzzy insulin control dose, which is represented by a set of truth-values for the appropriate members of the dose fuzzy covering. The method proceeds from 542 to 544.

At 544, the dispensing control system 100 calculates the insulin dose by defuzzifying the fuzzy insulin control dose. The dose value may be calculated, for example, by determining the centroid of the fuzzy insulin control dose. (Centroid is sometimes called center of mass or center of area.) The method proceeds from 544 to 546.

At 546, the dispensing control system 100 personalizes the insulin control dose by applying formula, which may be a simple formula such as multiplication by a constant parameter. The value of that parameter may be set, for example by a physician at enrollment and based on personal information regarding the individual. For example, it may be desirable to adjust the dosage based on the weight of an individual, that person's historical average insulin dose or other personal characteristics determined in laboratory testing. The method proceeds from 546 to 548.

At 548, the dispensing control system 100 displays the recent blood glucose history and the personalized insulin control dose. The method proceeds from 548 to 550.

At 550, a predicted BGL value, for example, a short time in the future, is calculated. This predicted value may be based on statistical analysis of the long-term BGL history or an extrapolation of the recently measured BGL data. The method proceeds from 550 to 552.

At 552, both the current BGL value and the predicted BGL value are compared to BGL_high, the high BGL safety threshold. (BGL_high may be set, for example, by a physician at enrollment.) If the threshold is exceeded the method proceeds to 556. Otherwise the method proceeds to 554.

At 554, both the current BGL value and the predicted BGL value are compared to BGL_low, the low BGL safety threshold. (BGL_low may be set, for example, by a physician at enrollment.) If the threshold is exceeded the method proceeds to 560. Otherwise the method proceeds to 558.

At 556, the dispensing control system 100 signals the high BGL, which may include displaying the high BGL safety condition as a text message and also as an aural signal. The method proceeds to transition 430 to 504.

At 558, the dispensing control system 100 signals the low BGL, which may include displaying the low BGL safety condition as a text message and also as an aural signal. The method proceeds to transition 429 to 504.

At 560, the dispensing control system 100 instructs the insulin pump to deliver the personalized insulin control dose. The method proceeds from 560 to 536.

Embodiments of the method illustrated in FIGS. 5A through 5C may contain additional acts not shown in FIGS. 5A through 5C, may not contain all of the acts shown in FIGS. 5A through 5C, may perform acts shown in FIGS. 5A through 5c in various orders, and may combine acts shown in FIGS. 5A through 5c. References to the states of FIG. 4 and to the systems of FIG. 1 in the description of FIG. 5 are intended as examples only.

An example enrollment procedure, which may be performed by or under the direction of a physician, is shown in Table 2 below. For convenience, it will be described as performed by a physician. The physician may use an enrollment procedure when an individual patient starts using embodiments of the automatic insulin delivery device described herein. The physician may decide the appropriate numerical value or ranges for variables and settings, such as control thresholds, that are appropriate for that individual and enter those values or ranges into an enrollment database. In some embodiments, the ability to enter the enrollment data may be limited to the physician and other designated medical personnel and protected, for example, by a password.

TABLE 2

EXAMPLE ENROLLMENT DATA

| Variable | Example Value | Description |
| --- | --- | --- |
| BGL_comp | 110 mg/dL | BGL target for IDC during compliant mode |
| BGL_semi | 140 mg/dL | BGL target for IDC during semi-compliant mode |
| BGL_non | 175 mg/dL | BGL target for IDC during non-compliant mode |
| BGL_low | 80 mg/dL | Low BGL Threshold for safety purposes |
| BGL_med | 150 mg/dL | Medium BGL Threshold |
| BGL_high | 180 mg/dL | High BGL Threshold for safety purposes |
| T_threshold | 120 minutes | Time to wait following a meal before entering the PMC state. |
| Carb_breakfast | 40 g | Assumed carb count for semi-compliant patient at breakfast |
| T_breakfast | 6:00 to 9:59 | Time window for breakfast |
| Carb_lunch | 60 g | Assumed carb count for semi-compliant patient at lunch |
| T_lunch | 10:00 to 14:59 | Time window for lunch |
| Carb_dinner | 100 g | Assumed carb count for semi-compliant patient at dinner |
| T_dinner | 15:00 to 20:59 | Time window for dinner |
| Carb_other | 30 g | Assumed carb count for semi-compliant patient at other time |
| T_other | 21:00 to 5:59 | Time other than T_breakfast, T_lunch or T_dinner |
| AI_max | 21 units | Active insulin cutoff |
| T_insulin | 205 minutes | Insulin activity time |
| Mult_per | 0.87 | Personalization multiplier |
| Carb_compliant | 50 g | Carbohydrate entered for a meal by compliant patient |
| Carb_bolus_factor | 1/10 U/g | The carb bolus factor for a compliant patient |
| BGL_correction | 120 mg/dL | The target BGL for a patient in need of a BGL correction |
| BGL_current | 200 mg/dL | The BGL indicated at the most current reading |
| BGL_corr_factor | 1/50 U/(mg/dL) | The BGL correction factor for a patient |
| T_prandial | 100 minutes | Elapsed time from a prandial event |
| BGL_trans_high | 180 mg/dL | High transition level from PMC to IDC |
| BGL_trans_med | 130 mg/dL | Medium transition level from PMC to IDC |
| BGL_trans_low | 100 mg/dL | Low transition level from PMC to IDC |

The system may be configured to predict when a particular insulin-dependent diabetic will experience hypo- or hyper-glycemia with a probability greater than some patient-specific, predetermined, settable alerting threshold. The techniques used here can be modified to predict other BGL related target values or trends expressed in terms of sequences of blood sugar values.

Hidden Markov Models (HMMs) are statistical models of sequential data that have been used successfully in many machine-learning applications, especially for speech recognition. [L. R. Rabiner, "A tutorial on hidden Markov models and selected applications in speech recognition," Proceedings of the IEEE, vol. 77, no. 2, pp. 257-286, 1989.]

The same techniques may be applied to the modeling the interaction of insulin and blood glucose in diabetics. An example application of HMM techniques is described below.

If the range of BGL values are partitioned into groups of, for example, ten, we may view the over-time dynamics of blood sugar as a time sequence of discrete state transitions, where each integer BGL value is the state. Suppose a patient's BGL is measured every fifteen minutes, and the last four measurements were 95, 111, 130 and 139, then the sequence S would be s(1)=95, s(2)=111, s(3)=130, s(4)=139

When using today's blood glucose sensors, without loss of generality, blood sugar measurements may be placed into groups of 10 where bg1=[10-19], bg2=[20-29], bg3=[30-39] and so on. In general, for positive integer N, bgN=[N*10, N*10+9]. Using the broader states the above sequence reads s(1)=bg9, s(2)=bg11, s(3)=bg13, s(4)=bg13

For a diabetic who subcutaneously infuses insulin, their Active Insulin (AI), or Insulin on Board, at any particular time, is a number that represents the amount of insulin in their body that is available to lower blood sugar. Because each dose of insulin generally produces effects for 8 hours, the AI number represents the cumulative effects, i.e., the "stacking" of the previous 8 hours of dosing.

The Active Insulin at time t for any patient may be expressed as:

$$AI(tc) = \Sigma D_i F(tc - t_i)$$

where Di, ti are the set of doses at times ti. F(t) is the attenuation factor for a dose earlier than the current time by t hours. There is no attenuation for a dose at the current time [F(t)=1.0]. A dose that is eight or more hours previous to the current time is completely attenuated [F(t)=0.0]. In between F(t) is a smooth curve given by the formula:

$$F(t) = \Sigma c_j t^{**j}$$

The coefficients for this polynomial of degree 6 are:
c0=0.9998
c1=0.045
c2=0.184
c3=0.0485
c4=0.005172
c5=0.0002243
c6=0.00000215

Because it is normally a decimal fraction, for simplicity the ai value can be set to the greatest integer less than its calculated value.

The BGL observation state space for a given patient may be expressed as a mathematical set: BG={bg|bg has the form bgj=[j*10, j*10+9] where positive integer j has min<=j<=max, and min and max are selected to represent the total range of blood glucose values for that patient}

For a patient whose blood sugar measurements are always between 55 and 433 mg/DL, their state space may be expressed as {5, 6, 7, . . . 43}

The BGL hidden state space for a given patient may be expressed as

BG-HMM={(bg,ai)|bg is as above and ai is the calculated Active Insulin at the time the blood glucose was measured.}

The BGL hidden state space for a given patient may be constructed as follows. Sufficient historical blood sugar measurement information for a patient is loaded into a database, along with insulin infusion information as downloaded from an insulin infusion pump. The blood sugar information may be frequent enough to obtain measurements for every fifteen-minute time interval. By correlating the blood sugar measurements with the insulin infusion records, the ai (Active Insulin) number is calculated for each bg (blood glucose) measurement. Similarly, the state transition probability for each (bg,ai) state can be calculated. See the Rabiner paper or any Markov Model textbook for state transition matrix construction details. The state transition matrix is a square matrix where the row and columns correspond with the states. The elements of row j, for example, are numbers between 0.0 and 1.0, the sum of which total 1.0. If the i-th element in row j is 0.3, that means that there is a 0.3 probability of transitioning from state j to state i. The sum of each row elements is 1.0 because it is true that given any state, you must transition somewhere.

To make every state in a patient's model accessible, we can choose the BGL and AI granularity to be wide enough; like 20+/−BGL and +/−AI. The more historical data available for a particular patient, the finer the granularity can be.

The Viterbi algorithm is a dynamic programming algorithm for finding the most likely sequence of hidden states—known as the Viterbi path—that result in a sequence of observed states. The list of possible sequences in the space is restricted to those that are physiologically possible for the patient, and is unique to each patient.

Figure 6:
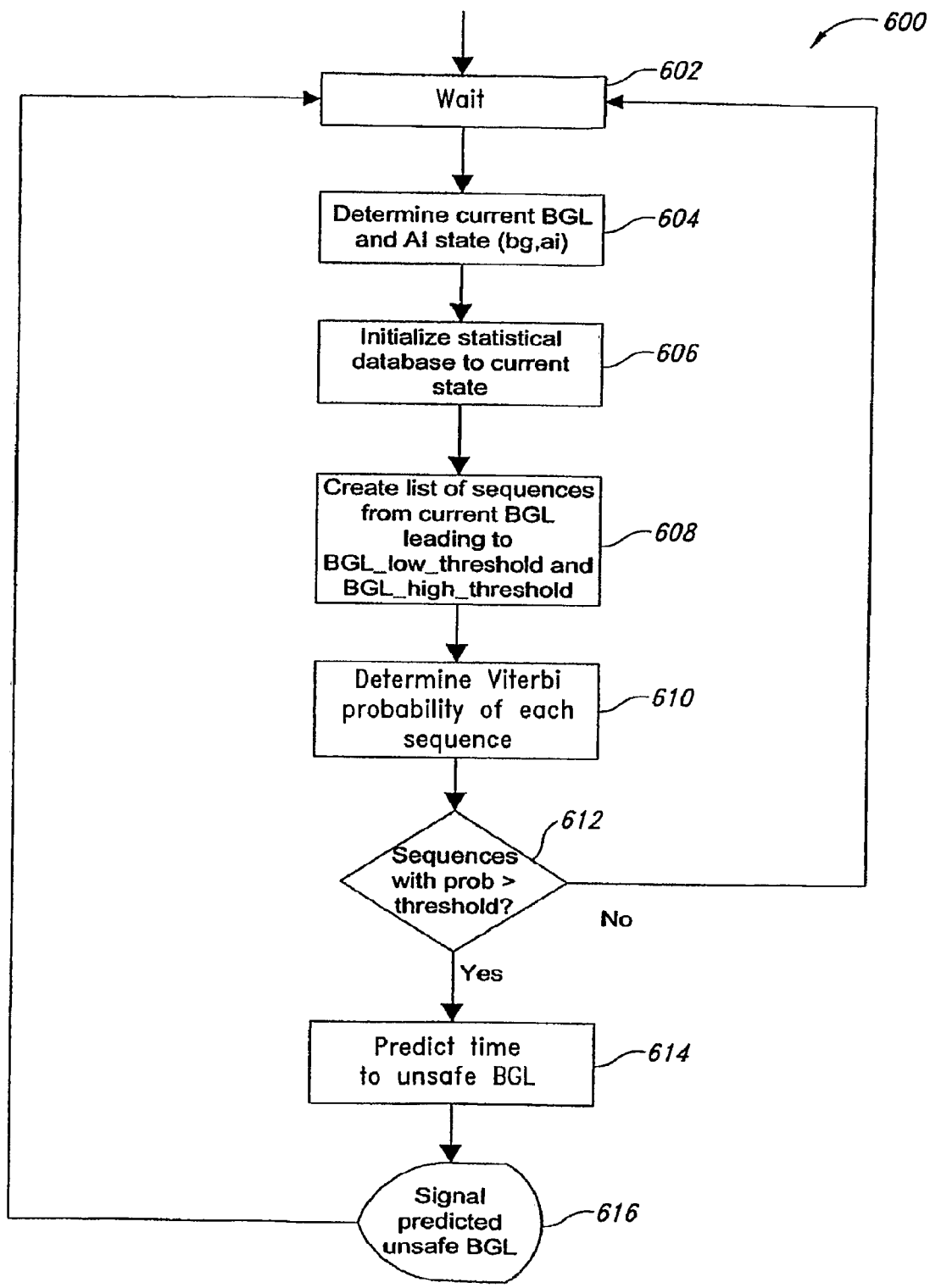
FIG. 6 is a high-level flow diagram for an embodiment of a method of predicting an unsafe blood glucose level.

FIG. 6 illustrates an embodiment of a method 600 of operating a system, such as the dispenser control systems 100, 200, 300 illustrated in FIGS. 1-3, to predict hypoglycemia in a patient. This may be done, for example, by predicting the probability that a sequence of observed states will produce a blood glucose level at or below a threshold $BG_{MIN}$ during a selected time period. When the probability is non-zero or above a threshold probability, the system may be configured to predict when a hypoglycemic event will occur. The threshold $BG_{MIN}$ may be a constant or a variable. For convenience, the method will be described by example with respect to the dispenser control system 100 of FIG. 1.

At 602, the system 100 waits until a beginning of a prediction cycle. For example, the system 100 may be configured to run a prediction cycle when new data are available. The system may be configured to run a prediction cycle periodically, such as at 15 minute intervals. The method 600 proceeds from 602 to 604.

At 604, the system 100 determines a current blood glucose level, active insulin level and the BGL HMM hidden state, BGL_HMM (bg, ai)$_{CUR}$, as discussed above for example. The method 600 proceeds from 604 to 606. At 606, the system 100 initializes a statistical database to the current state. The method 600 proceeds from 606 to 608.

At 608, the system 100 determines a set S of sequences $s_i$ of BGL observed stated BG. Conditions may be imposed on the sequences. For example, for each I, $s_i(1)=bg_{CUR}$ and $s_i(last)=bg_{MIN}$, wherein $s_i(last)$ is the last element of the sequence $s_i$, conditions may include for all j, k where $1 \leq j \leq k$ last$_i$, $s_i(j) \leq s_i(k)$, and $s_i(k)-s_i(j) \leq$ the maximum recorded BGL. The sequences $s_i$ will have a finite length, there will be a finite number such sequences, and the sequences will be reasonable. For example, sequences will not have an element that falls more quickly than previously experienced by a patient. The method 600 proceeds from 608 to 610.

At 610, the system 100 determines a probability for the sequences in the set S that the sequence $s_i$ will produce a BGL less than a threshold BGL. This may be done, for example, by determining a Viterbi probability for each sequence $s_i$ in the set S. The method 600 proceeds from 610 to 612.

At 612, the system 100 compares the probability for the sequences in the set S to a threshold probability, which may be zero. When the system 100 determines that the probability for one or more sequences $s_i$ in the set S exceeds the threshold probability, the method 600 proceeds from 612 to 614. When the system 100 determines that none of the sequences $s_i$ in the set S have a probability exceeding the threshold probability, the method 600 proceeds from 612 to 602.

At 614, the system 100 predicts when a hypoglycemic event will occur. This may be done, for example, by selecting the shortest sequence having a probability exceeding the threshold probability and predicting a time based on the length of the selected sequence and the length of the prediction cycle or of the data cycle (which may be the same). For example, if data are received every 15 minutes and a prediction cycle occurs in response to the receipt of the data, the length of the selected sequence may be divided by four to predict when an event will occur in hours. The method 600 proceeds from 614 to 616, where the unsafe BGL is predicted to occur and when may include instructions or suggestions for avoiding the unsafe BGL. The method 600 proceeds from 616 to 602.

Embodiments of the method 600 of FIG. 6 may contain additional acts not shown in FIG. 6, may not contain all of the acts illustrated in FIG. 6, and may combine or separate acts illustrated in FIG. 6. For example, the dispenser control system 100 may be configured to predict hyperglycemic events in addition to or instead of hypoglycemic events (e.g., predict blood glucose levels above a threshold range, or predict blood glucose levels above a threshold in combination with a rate of increase in the blood glucose level that is above a threshold rate of increase). The threshold levels and ranges discussed with respect to FIG. 6 may be fixed or may be functions and may be based on statistical analysis.

Figure 7:
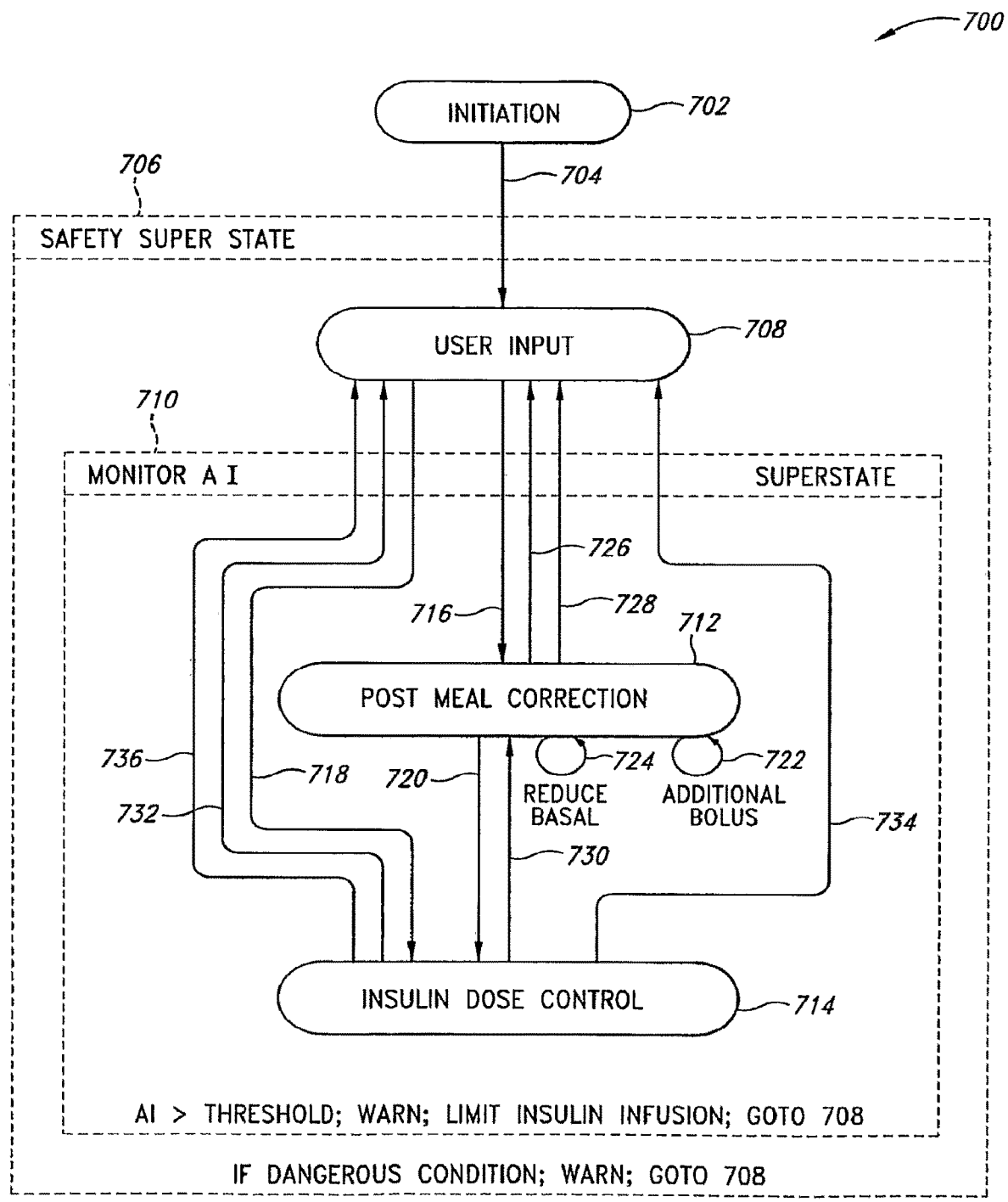
FIG. 7 is a high-level hierarchical state diagram for an embodiment of a method of operating a dispenser control system.

FIG. 7 is another high-level hierarchical state diagram 700 illustrating another example method of controlling a dispenser control system, such as the dispenser control systems 100, 200, 300 illustrated in FIGS. 1-3. For convenience, the state diagram 700 will be described with reference to the dispenser control system 100 illustrated in FIG. 1. The dispenser control system 100 is initiated at initiation state 702. A user may typically initiate the dispenser control system 100 just prior to consumption of a meal or when it is desirable to enter information regarding an individual.

The dispenser control system 100 transitions 704 from initiation state 702 to a safety super-state 706 and enters a wait-for-user-input state 708.

While in the safety super-state 706, the dispenser control system 100 determines whether data generated or received by dispenser control system 100 indicates that a dangerous condition exists. When the dispenser control system 100 determines in the safety super state 706 that a dangerous condition exits, the dispenser control system 100 may be configured to generate control signals to active an alarm (e.g., a visual alarm, an audio alarm, a vibration alarm, a remote alarm, and/or combinations of the above), which may vary based on the nature of the dangerous condition and/or the operational state of the dispenser control system, and to cause the dispenser control system 100 to transition to the wait-for-user-input state 708. For example, when the dispenser control system 100 determines that an individual is sleeping and that a dangerous condition has arisen, the dispenser control system may be configured to sound an alarm loud enough to wake the individual. The dispenser control system 100 may be configured to determine that a dangerous condition exists in response to, for example: an indication that a monitored blood glucose level is below or above threshold levels; an indication that a predicted blood glucose level will be below or above threshold levels; an indication of an equipment failure; or an indication of improbable blood glucose levels for an individual (for example, blood glucose levels inconsistent with an individual's history or historical glycemic profile, or with data received regarding an individual, such as an indication of when a meal was consumed or a carbohydrate ratio of a meal).

In the illustrated state diagram 700, the dispenser control system 100 also is configured to determine whether a dangerous condition exists by monitoring the active insulin level in the monitor active insulin (AI) super-state 710, as discussed in more detail below. When the dispenser control system 100 determines in the monitor active insulin super state 710 that a dangerous condition exits based on the monitoring of the active insulin level, the dispenser control system 100 may be configured to generate control signals to active an alarm and to limit insulin infusion, and to transition to the wait-for-user-input state 708.

The threshold levels and ranges may be fixed or may be functions and may be based on statistical analysis. For example, an indication of a blood glucose level below a threshold level of 80 mg/dl may cause the dispenser control system 100 to determine that a dangerous condition exists. In another example, an active insulin level above a threshold level of 20 insulin units may cause the dispenser control system 100 to determine in the monitor active insulin super state 710 that a dangerous condition exists. An active insulin level may be determined based on a history of doses over a selected time period, with the impact of each dose adjusted using a form factor indicative of the reduced insulin activity due to the time elapsed since the dose was given. A threshold insulin activity maximum level may be fixed or a function, and may be set using an adjustable input parameter. Similarly, the determination of whether a blood glucose level is improbable may be based on thresholds, functions and statistical analysis. Look-up tables, fuzzy logic and/or neural networks may be employed, for example. Indications of equipment failure may include direct indications (for example, an error signal from the insulin dispenser 104), or indirect indications (for example, inconsistent indications of blood glucose levels from multiple blood glucose sensors 108 in a blood glucose sensor system 102, or an indication that a pump is not operating properly, such as an indication an insulin dispenser 104 is not responding to a control signal).

In the state diagram illustrated in FIG. 7, when the dispenser control system 100 determines that a dangerous condition exists, the dispenser control system 100 is configured to trigger an alarm (such as an alarm by the user output 164 and/or a remote alarm) and to enter the wait-for-user-input state 708.

The dispenser control system 100 is configured to enter the wait-for-user-input state 708 when the dispenser control system 100 is initiated, when invoked by the user (for example, when the user wishes to enter information such as information regarding a meal), which may be at the same time as initiation, or in response to a dangerous condition or an anomaly being detected. In the wait-for-user-input state 708, the dispenser control system 100 is configured to wait for user input. The dispenser control system 100 may be configured to prompt the user for input, and may be configured to signal an alarm. For example, when the wait-for-user-input state 708 is entered from the safety super-state 706 or the monitor AI super state 710, the dispenser control system 100 may be configured to signal an alarm. The dispenser control system 100 may be configured to time-out if no user input is received within a threshold period of time. For example, when the wait-for-user-input state 708 is entered from initiation state 702, the dispenser control system 100 may be configured to wait for a threshold period of time for input from a user, and then transition to another state such as the post-meal correction state 712 or the insulin dose control state 714 if certain conditions are satisfied, as discussed in more detail below. The dispenser control system 100 may be configured to respond to direct commands to dispense particular amounts of insulin, and may be further configured to require confirmation, for example, if a commanded dose is inconsistent with an actual or predicted blood glucose level or an active insulin level.

The user input may include information regarding a meal about to be consumed, a meal recently consumed, or information about an individual, as discussed above. When the information includes information regarding a meal that is about to be consumed, the dispenser control system 100 may be configured to generate control signals to cause the insulin dispenser 104 to dispense a bolus dose (or a pre-meal dose) of insulin. The bolus dose may be calculated using known methods using factors that may include, for example, insulin sensitivity and a carbohydrate ratio. The dispenser control system 100 may also be configured to generate control signals to cause the insulin dispenser 104 to dispense a basal insulin dose. Basal insulin doses may be dispensed periodically and a wide range of dosing intervals may be employed (e.g., fifteen minute dosing intervals).

The dispenser control system 100 is configured to transition 716 from the wait-for-user-input state 708 to the post-meal correction state 712 when it is determined that a meal has recently been consumed. This determination may be made, for example, in response to user input indicating a meal has been consumed or in response to an indication, such as a blood sugar level history, consistent with a meal being consumed. Fuzzy logic, a neural network and/or a look-up table may be employed, for example, to determine whether a meal has been consumed.

The dispenser control system 100 may be configured to delay the transition 716. For example, the dispenser control system 100 may be configured upon determining that an unreported meal has been consumed, to prompt the user for information about the meal and to wait a threshold period of time before transitioning 716 to the post-meal correction state 712. In another example, it may be desired to delay post-meal correction for a threshold period of time after a meal is consumed. In such a case, the dispenser control system 100 may be configured to wait until a post-prandial delay threshold (e.g. two hours) has been exceeded before transitioning 716 from the wait-for-user-input state 708 to the post-meal correction state 712.

The dispenser control system 100 is configured to transition 718 from the wait-for-user-input state 708 to the insulin dose control state 714 when threshold conditions are satisfied. The threshold conditions may include, for example, a blood glucose level within an acceptable range, an active insulin level within an acceptable range, and the absence of an indication that a meal has been consumed within a threshold period of time. For example, if the history is consistent with a sufficient post-prandial period, the user has not entered information indicating a meal has been or is about to be consumed, the blood glucose level is within a threshold range (e.g., between 90 and 140 mg/dl), the active insulin level is below a threshold level (e.g., 20 insulin units), and the time is consistent with nocturnal operation, the dispenser control system 100 may be configured to transition 718 from the wait-for-user-input state 708 to the insulin dose control state 714 (e.g., for nocturnal control of blood glucose level). The dispenser control system 100 may be configured to require user input before transitioning 718 from the wait-for-user-input state 708 to the insulin dose control state 714 (e.g., express confirmation that no meal has been consumed for the past several hours and that no meal will be consumed for the next several hours). Determining whether the user has entered information indicating a meal has been or is about to be consumed may include waiting a threshold period of time for the user to enter information, if desired.

As illustrated, the wait-for-user-input state 708 is within the safety super state 706. Thus, the dispenser control system 100 may be configured not to transition from the wait-for-user input state 708 to another state if a dangerous condition exists, and when it is determined that a dangerous condition has developed while the dispenser control system 100 is in the wait-for-user-input state 708, the dispenser control system 100 may be configured to generate control signals to activate an alarm.

In the post-meal correction state 712, the dispenser control system 100 is configured to periodically determine whether an additional bolus dose should be provided, whether a basal dose should be reduced, or whether the conditions are such that the dispenser control system 100 should transition 720 to the insulin dose control state 714. For example, if an acceleration of blood glucose level indicates an insufficient bolus dose was provided, the dispenser control system 100 may be configured to dispense an additional bolus dose 722. In another example, if a rate of change of blood glucose level indicates too large a bolus dose was provided, the dispenser control system 100 may be configured to reduce the basal dose 724. A minimum basal dose level may be set or determined based on information about the individual. In another example, the dispenser control system 100 may be configured to transition 720 to the insulin dose control state 714 when threshold conditions are satisfied. For example, if the history is consistent with a sufficient post-prandial period, the blood glucose level is within a threshold range (e.g., between 90 and 140 mg/dl), and the active insulin level is below a threshold (e.g., 20 insulin units), the dispenser control system 100 may be configured to transition 720 from the post-meal correction state 712 to the insulin dose control state 714.

As illustrated, the post-meal correction state 712 is within the safety super state 706 and the monitor active insulin super state 710. The dispenser control system 100 may be configured to activate an alarm and transition 726 from the post-meal correction state 712 to the wait-for-user-input state 708 when it is determined that a dangerous condition exists. Further, when the determination that a dangerous condition exists is based in part on a determination that an active insulin level exceeds a threshold level, the dispenser control system 100 may be configured to limit insulin infusion. For example, the dispenser control system 100 may limit insulin infusion to a threshold amount for a threshold period of time. The dispenser control system 100 also may be configured to transition 728 from the post-meal correction state 712 to the wait-for-user-input state 708 in response to commands received by the dispenser control system 100 (e.g., a command entered by a user).

The dispenser control system 100 is configured in the insulin dose control state 714 to monitor blood glucose levels and to periodically dispense insulin based on the current blood glucose level and the history of the monitored blood glucose levels. The dispenser control system 100 may be configured to dispense insulin based on other information about an individual, as discussed above. The dispenser control system 100 may employ, for example, fuzzy logic, a neural network, a look-up table, or software routines to periodically dispense insulin based on the history of the monitored blood glucose levels and other information. Table 3 below illustrates an example fuzzy logic Dosing Rules Matrix that may be applied by the dispenser control system 100 to control the dispensing of insulin while in the insulin dose control state. The dosing identifiers in Table 3 represent experimentally distinct doses of insulin, which may be measured in Units of Insulin. The dosing identifiers from largest dose to smallest dose are VVL (very very large), VL (very large), LRH (large high), LR (large), LRL (large low), MDH (medium high), MD (medium), MDL (medium low), SMH (small high), SM (small), SML (small low) and VSM (very small). The first fuzzy input is the current blood glucose level BGL in mg/dl units, represented in the bottom four rows with fuzzy coverings VH (very high), HI (high), MD (medium), and NR (normal). The second fuzzy input is the rate of change of the blood glucose level, represented in row BGL RATE with fuzzy coverings N (negative), Z (zero), P (positive) and very positive. The third fuzzy variable is acceleration of the blood glucose level, represented in row BGL Acceleration with fuzzy coverings N (negative), Z (zero) and P (positive). Example trajectories corresponding to the blood glucose level rate of change and acceleration are illustrated in row BGL Trajectory. The fuzzy coverings may be experimentally determined, and may vary based on additional factors such as the method of delivering a dose of insulin.

TABLE 3

EXAMPLE DOSING RULES MATRIX

| BGL Rate: | | N | | | Z | | | P | | | VP | |
|---|---|---|---|---|---|---|---|---|---|---|---|---|
| BGL Acceleration: | N | Z | P | N | Z | P | N | Z | P | N | Z | P |
| BGL Trajectory: | | | | | | | | | | | | |
| BGL VH | LRL | LR | LRH | LRH | LRH | VL | VL | VL | VL | WL | WL | VVL |
| HI | SM | SMH | MDH | SMH | MDL | LRL | MDH | VL | VL | MDH | VVL | WL |
| MD | SML | SM | SMH | SM | SMH | MDL | SMH | MDH | MDH | SMH | WL | WL |
| NR | VSM | VSM | VSM | VSM | SML | SM | SML | SM | SMH | SML | SM | SMH |

The dispenser control system 100 is configured to transition 730 from the insulin dose control state 714 to the post-meal correction state 712 when the dispenser control system 100 determines that a meal has been consumed and that the size of the meal is such that additional user input regarding the meal is not necessary. For example, the dispenser control system 100 may be configured to transition 730 from the insulin dose control state 714 to the post-meal correction state 712 when a current indication of a blood glucose level is within a threshold level (e.g., between 160 mg/dl and 200 mg/dl) and the increase in the current indication of a blood glucose level from the previous indication of a blood glucose level exceeds a threshold level (e.g., the indication of a blood glucose level jumped by more than 10 mg/dl since the last measurement was received). The dispenser control system 100 may be configured to transition 732 from the insulin dose control state 714 to the wait-for-user input state 708 when the dispenser control system 100 determines that a large meal has been consumed and that it is desirable and/or necessary to obtain user input. For example, the dispenser control system 100 may be configured to transition 732 from the insulin dose control state 714 to the wait-for-user input state 708 when a current indication of a blood glucose level is above a threshold level (e.g., above 200 mg/dl) and the increase in the current indication of a blood glucose level from the previous indication of a blood glucose level exceeds a threshold level (e.g., the indication of a blood glucose level jumped by more than 10 mg/dl since the last measurement was received).

As illustrated, the insulin dose control state 714 is within the safety super state 706 and the monitor active insulin super state 710. The dispenser control system 100 is configured to activate an alarm and transition 734 from the insulin dose control state 714 to the wait-for-user-input state 708 when it is determined that a dangerous condition exists. Further, when the determination that a dangerous condition exists is based in part on a determination that an active insulin level exceeds a threshold level, the dispenser control system 100 may be configured to limit insulin infusion. For example, the dispenser control system 100 may limit insulin infusion to a threshold amount for a threshold period of time. The dispenser control system 100 also may be configured to transition 736 from the insulin dose control state 714 to the wait-for-user-input state 708 in response to commands received by the dispenser control system 100 (e.g., a command entered by a user, for example, an indication that a meal is about to be consumed).

Embodiments of the method of operation a dispenser control system illustrated by the hierarchical state diagram 700 of FIG. 7 may not contain all of the illustrated states, superstates and transitions, may contain additional states, superstates and transitions, or may combine or separate illustrated states and superstates. For example, the post-meal correction state 712 and the insulin dose control state 714 may be combined into an automatic dose control state in some embodiments. The threshold levels and ranges discussed with respect to FIG. 7 may be fixed or may be functions and may be based on statistical analysis. The embodiment of FIG. 7 may also be modified to transition to the wait-for-user-input state and to sound an alarm upon an indication predictive of a dangerous condition.

Figure 8:
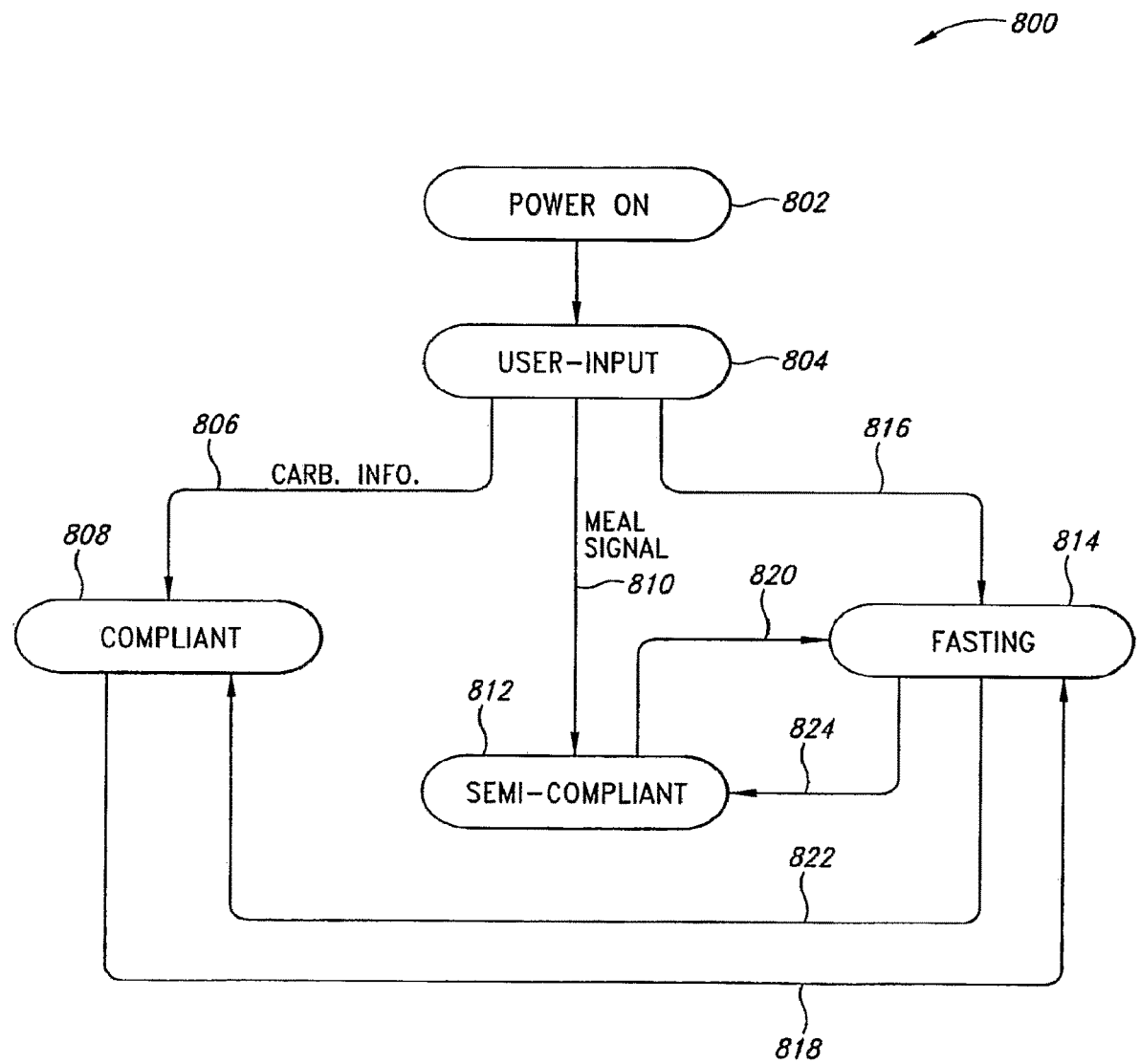
FIG. 8 is a high-level state diagram for an embodiment of an example method of operating a dispenser control system.

FIG. 8 is a high-level state diagram 800 illustrating another example method of operating a system, such as the dispenser control systems 100, 200, 300 illustrated in FIGS. 1-3. For convenience, the state diagram will be described with reference to the dispenser control system 100 illustrated in FIG. 1.

The dispenser control system 100 is powered on at state 802. The dispenser control system 100 enters a user-input state or mode 804. In the user-input state 804, the dispenser control system 100 waits for user input (e.g., for a threshold period of time), and based on any received user input and/or data received or previously stored by the dispenser control system 100, may transition to one of three states or modes of operation. User-input may also be received in other states or modes of operation, for example, as discussed in more detail below.

When the dispenser control system 100 is in the user-input state 804 and receives information indicating a meal has been or is about to be consumed (e.g., user input or received data indicating a meal has been consumed) and user input indicative of a carbohydrate content for the meal, the dispenser control system 100 is configured to transition 806 from the user-input state 804 to a compliant state or mode 808. The compliant state 808 is entered because the user has complied with a request to supply information indicative of the carbohydrate content of the meal that is about to be, or has recently been, consumed. In some embodiments, the indication that a meal has been or is about to be consumed may be determined solely based on user input. In some embodiments, the system may prompt the user for carbohydrate information and, depending on whether information is provided in response to the prompt, transition to either the compliant 808 or semi-compliant 812 state.

When the dispenser control system 100 is in the user-input state 804 and receives information indicating a meal is about to be or has been recently consumed, but does not receive information indicative of a carbohydrate content for the meal, the dispenser control system 100 transitions 810 from the user-input state 804 to a semi-compliant state 812. The semi-compliant state 812 is entered because the dispenser control system 100 has determined that a meal was recently, or is about to be, consumed, but has not been provided with an indication of the carbohydrate content of the meal. In some embodiments, the indication that a meal has been or is about to be consumed may be determined solely based on user input.

When the dispenser control system 100 is in the user-input state 804, and determines that it is appropriate to operate in a fasting state or mode 814, the dispenser control system 100 is configured to transition 816 from the user-input state 804 to the fasting state 814. For example, the dispenser control system 100 may determine it is appropriate to transition 816 from the user-input state 804 to the fasting state 814 when there is no indication that a meal is about to be or has been recently consumed, and an indication of a blood glucose level is within a threshold range (e.g., between 90 and 140 mg/dl). In another example, the dispenser control system may also determine it is appropriate to transition 816 from the user-input state 804 to the fasting state 814 when the user inputs data indicating the user is fasting, and an indication of a blood glucose level or history is consistent with this input (e.g., the blood glucose level is within a threshold range).

In the compliant mode 808, the dispenser control system 100 sets a post-prandial blood glucose level target and may generate control signals to dispense insulin doses based on the target post-prandial blood glucose level, the information regarding the carbohydrate content of the meal, stored and received data regarding the individual consuming the meal, and/or current and historical indications of the blood glucose level of the individual. For example, the dispenser control system 100 may dispense and adjust bolus and basal insulin doses (see, for example, the discussion above with respect to the post-meal correction state 712 of FIG. 7).

The dispenser control system 100 is configured to transition 818 from the compliant state 808 to the fasting state 814 when a fasting criteria is satisfied. For example, the dispensing control system 100 may be configured to transition 818 from the compliant state 808 to the fasting state 814 when a threshold amount of time has passed since the dispenser control system 100 entered the compliant state 808 (e.g., three hours) and the blood glucose level is within a threshold range (e.g., 90 to 140 mg/dl). Other criteria may be imposed. For example, a rate of change of the blood glucose level may need to be within a threshold range for the fasting criteria to be satisfied.

In the semi-compliant mode 812, the dispenser control system 100 sets a post-prandial blood glucose level target and may generate control signals to dispense insulin doses based on the target post-prandial blood glucose level, stored and received data regarding the individual consuming the meal (which may include indications of historical carbohydrate levels), and/or current and historical indications of the blood glucose level of the individual. For example, the dispenser control system 100 may dispense and adjust bolus and basal insulin doses (see, for example, the discussion above with respect to the post-meal correction state 712 of FIG. 7).

The dispenser control system 100 is configured to transition 820 from the semi-compliant state 812 to the fasting state 814 when a fasting criteria is satisfied. For example, the dispensing control system 100 may be configured to transition 820 from the semi-compliant state 812 to the fasting state 814 when a threshold amount of time has passed since the dispenser control system 100 entered the semi-compliant state 812 (e.g., three hours) and the blood glucose level is within a threshold range (e.g., 90 to 140 mg/dl). Other criteria may be imposed. For example, a rate of change of the blood glucose level may need to be within a threshold range for the fasting criteria to be satisfied.

The dispenser control system 100 is configured in the fasting state 814 to monitor blood glucose levels and to periodically dispense insulin based on the current blood glucose level and the history of the monitored blood glucose levels. For example, the dispenser control system 100 may selectively generate one or more control signals to cause the insulin dispenser 104 to dispense one or more doses of insulin to maintain a desired fasting blood glucose level. The number, size and timing of the doses may be determined based on any number of criteria, including, for example, information stored by the dispenser control system 100 or entered through the user input device 162 regarding patient weight or body-mass index, sensed current and historical blood glucose levels, including past post-prandial blood glucose histories for the patient, indications of insulin sensitivity for the patient, and other information pertinent to maintaining a target fasting blood glucose level. The dispenser control system 100 may employ, for example, fuzzy logic, a neural network, a look-up table, software routines, or combinations thereof to periodically dispense insulin based on the history of the monitored blood glucose levels. For example, the fuzzy logic rules illustrated in the matrix of Table 1 may be applied.

When the dispenser control system 100 is operating in the fasting state 814 and receives information (e.g., indications of a change in blood glucose level consistent with eating a meal) or user input is received that provides an indication that a meal has been or is about to be consumed and an indication of a carbohydrate content for the meal, the dispenser control system 100 transitions 822 to the compliant state 808. When the dispenser control system 100 is in the fasting state and receives information (e.g., indications of a change in blood glucose level consistent with eating a meal) or user input is received that indicates a meal has been or is about to be consumed, but no or insufficient information is received regarding a carbohydrate content for the meal, the dispenser control system 100 transitions 824 to the semi-compliant state 812.

Embodiments of the state diagram illustrated in FIG. 8 may contain additional states not shown in FIG. 8, may not contain all of the states illustrated in FIG. 8, may contain additional transitions not illustrated in FIG. 8, may not contain all of the transitions illustrated in FIG. 8, and may combine or separate states illustrated in FIG. 8. For example, the dispenser control system 100 may be configured to set an alarm and transition to the user-input state whenever an error is detected, such as an equipment malfunction, or if unsafe blood glucose levels are detected or predicted (e.g., blood glucose levels outside a threshold range, or blood glucose levels above a threshold in combination with a rate of increase in the blood glucose level that is above a threshold rate of increase). In another example, the compliant and semi-compliant modes may be combined in some embodiments. The threshold levels and ranges discussed with respect to FIG. 8 may be fixed or may be functions and may be based on statistical analysis.

Figure 9A:
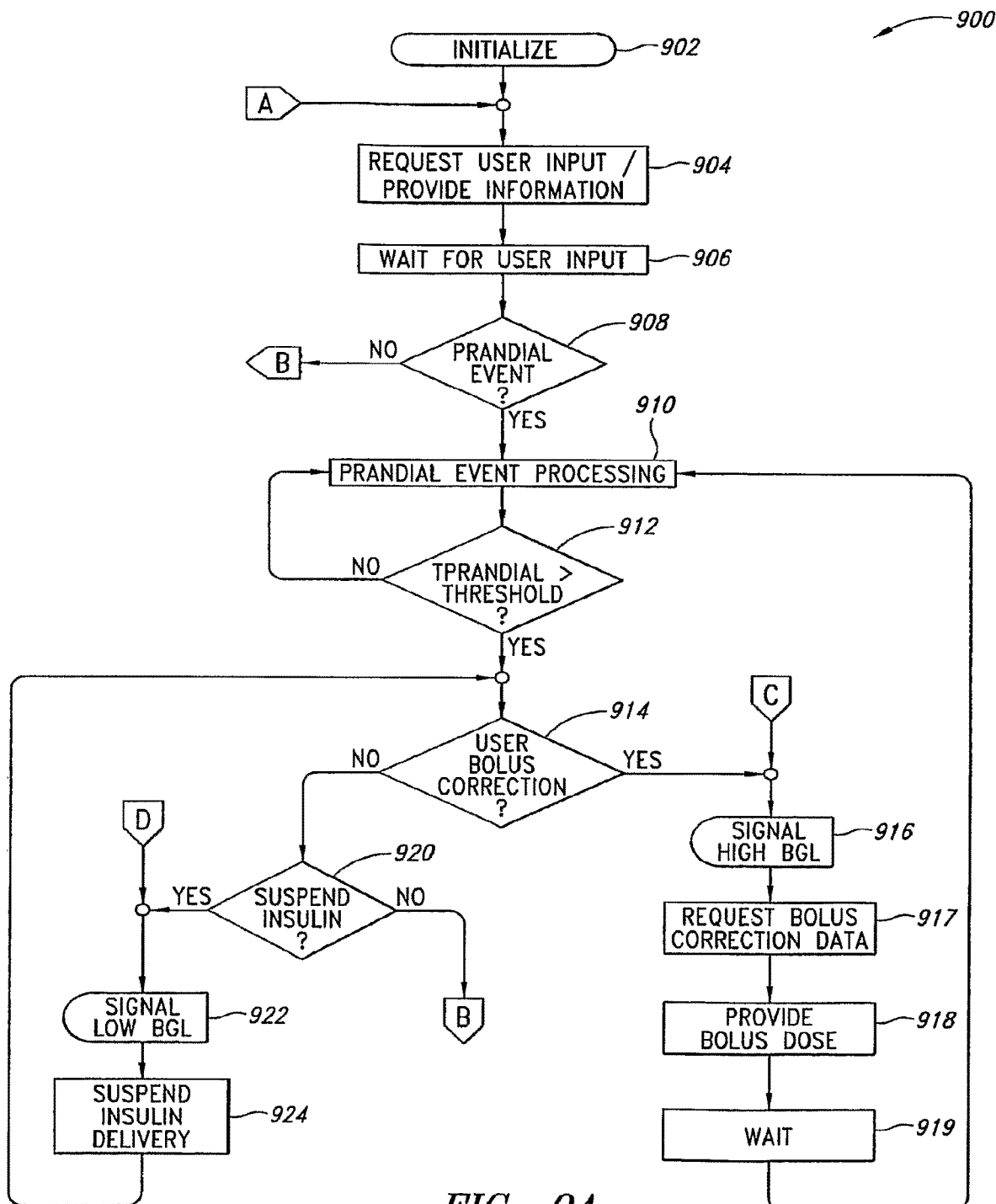
FIGS. 9A through 9C are a mid-level flow diagram for an embodiment of a method of operating a dispenser control system.
Figure 9B:
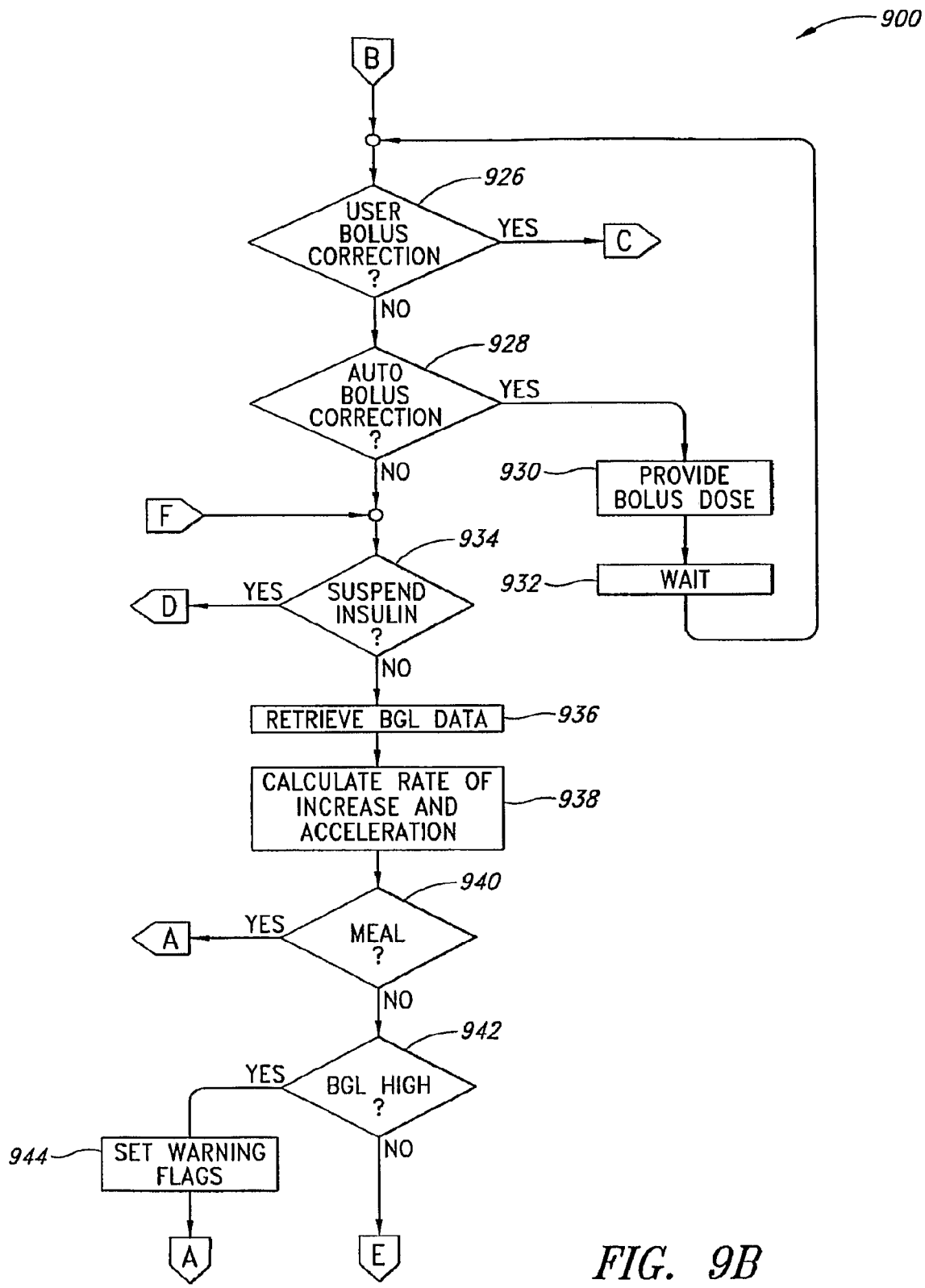
Figure 9C:
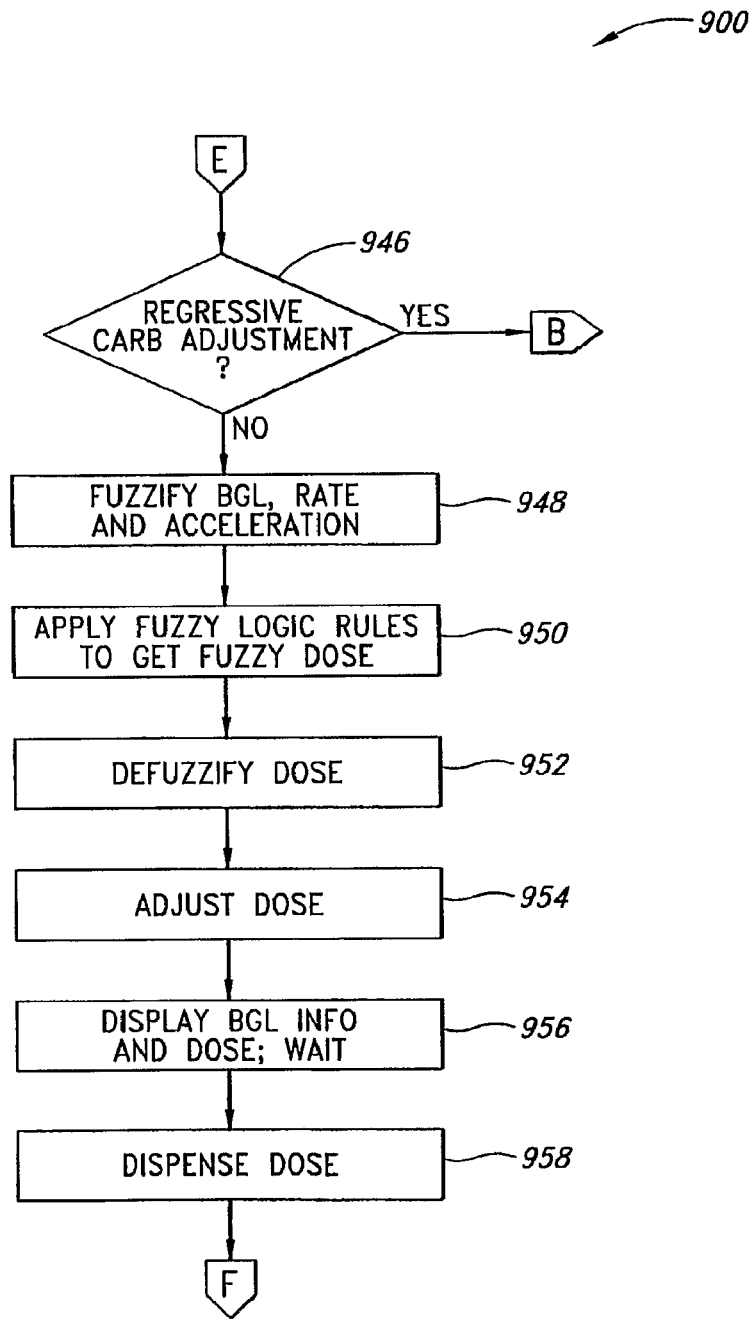

FIGS. 9A through 9C illustrate a mid-level flow diagram of an another example embodiment of a method 900 that may be employed by a system, such as the dispenser control systems 100, 200 and 300 illustrated in FIGS. 1 through 3, to control the dispensing of insulin. For convenience, the method will be described with respect to the embodiment of a dispenser control system 100 illustrated in FIG. 1.

The dispenser control system 100 initializes the method 900 at 902. The method 900 proceeds from 902 to 904. At 904, the dispenser control system 100 requests user input and optionally provides information to the user. For example, when the method 900 has proceeded to 904 in response to an initialization, the dispenser control system 100 may be configured to request data input regarding the individual for whom the dispenser control system 100 is to control the blood glucose level, such as, for example, input identifying an individual which can be associated with previously stored information. In another example, the dispenser control system 100 may be configured to request user-input related to whether a meal is about to be or has recently been consumed, and if so, information related to the meal, such as information related to a carbohydrate content of the meal. In another example, when the method has proceeded to 904 in response to the detection of a dangerous condition, the dispenser control system 100 may be configured to alert the user to the dangerous condition and to request user-input related to a response to the dangerous condition. For example, the dispenser control system 100 may be configured to request information related to a bolus dose if the dangerous condition detected is an indication that a large meal was consumed. The dispenser control system 100 may, for example, be configured to set flags to facilitate requesting appropriate user-input for use in determining an appropriate response to a dangerous condition. In some embodiments, when the method has proceeded to 904 in response to the detection of a dangerously low blood glucose level, the dispenser control system 100 may be configured to alert the user to the dangerous condition, to suggest that the user take appropriate action, such as consuming a meal containing a particular range of carbohydrates, and to request that the user confirm consumption of the meal and enter information related to the carbohydrate content of the meal.

The method 900 proceeds from 904 to 906. At 906, the dispenser control system 100 waits for user input. The dispenser control system 100 may be configured to wait for user input for a threshold period of time, or to wait until user input is received, or combinations of the above. For example, the dispenser control system 100 may be configured to wait for information related to the identity of an individual, and after information identify the individual is received, to wait a threshold period of time to give the user an opportunity to enter information related to a meal. The threshold period of time may vary. For example, different threshold periods of time may be employed depending on whether a dangerous condition flag is set. The method 900 proceeds from 906 to 908.

At 908, the dispenser control system 100 determines whether there is an indication of a prandial event. The dispenser control system 100 may be configured to determine whether there is an indication of a prandial event in response to user input, data received, for example, from the blood glucose sensor system 102, historical data received by the blood glucose sensor system 102, data previously entered by the user, or combinations of the above. For example, the user may enter data indicating a prandial event is about to occur, with or without an indication of a carbohydrate content of the meal. In another example, the dispenser control system 100 may determine based on indications of blood glucose levels received from the blood glucose sensor system 102 that a prandial event has occurred. When the dispenser control system 100 determines that there is an indication of a prandial event, the method 900 proceeds from 908 to 910. When the dispenser control system 100 determines that there is not an indication of a prandial event, the method 900 proceeds from 908 to 926. In some embodiments, when the dispenser control system 100 determines that there is not an indication of a prandial event, the method 900 proceeds from 908 to 936.

At 910, the dispenser control system 100 generates control signals to control the dispensing of insulin in response to the prandial event based on any received user input and/or other data. For example, the dispenser control system 100 may dispense an initial bolus dose. In some embodiments, an indication of the blood glucose level may be checked periodically (e.g., every 30 minutes) to determine whether to request additional input data from the user. For example, in some embodiments if the blood glucose level exceeds a threshold amount after 30 minutes (e.g., 200 mg/dl), the user may be asked whether an additional bolus dose should be administered. The method proceeds from 910 to 912.

At 912, the dispenser control system 100 determines whether there the sufficient time has elapsed since the prandial event. The dispenser control system 100 may determine whether sufficient time has elapsed by, for example, comparing the elapsed time to a threshold (e.g., two hours). The dispenser control system 100 may employ, for example, look-up tables, neural networks, and/or fuzzy logic to determine whether a sufficient amount of time has elapsed since the prandial event. When the dispenser control system 100 determines that a sufficient amount of time has elapsed since the prandial event, the method 900 proceeds from 912 to 914. When the dispenser control system 100 determines that a sufficient amount of time has not elapsed since the prandial event, the method 900 proceeds from 912 to 910.

At 914, the dispenser control system 100 determines whether additional data from the user is desirable for use in making a bolus correction. For example, the dispenser control system 100 may determine that additional data is desirable if the blood glucose level is above a threshold level (e.g., 200 mg/dl) and the increase since a last blood glucose level is above a threshold (e.g., the blood glucose level has increased by more than 10 mg/dl since the last reading). The dispenser control system 100 may employ, for example, neural networks, look-up tables and/or fuzzy logic to determine whether additional data from the user is desirable.

When the dispenser control system 100 determines at 914 that additional data from the user is desirable, the method 900 proceeds from 914 to 916. At 916, the dispenser control system 100 signals the user that the blood glucose level is too high. The dispenser control system 100 may also be configured to set an indication of a new prandial event (e.g., the dispenser control system 100 may reset a counter tracking the time since the last prandial event.) The method 900 proceeds from 916 to 917. At 917, the dispenser control system 100 requests and waits for user input for use by the dispenser control system 100 in determining an appropriate bolus correction. The method 900 proceeds from 917 to 918. At 918, the dispenser control system 100 determines a bolus dose and generates control signals to cause the insulin dispenser to dispense the bolus dose. The size of the bolus correction insulin dose may be determined, for example, based user input, received data, stored data, the size and number of prior bolus doses, or combinations of the above. The dispenser control system 100 may employ, for example, neural networks, look-up tables and/or fuzzy logic to determine the size of the bolus dose. The method 900 proceeds from 918 to 919. At 919, the dispenser control system 100 waits a threshold period of time (e.g., thirty minutes) for the insulin in the bolus dose to work in the individual. After the threshold period of time has elapsed, the method 900 proceeds from 919 to 910.

When the dispenser control system 100 determines at 914 that requesting additional data from the user is not necessary or desirable, the method 900 proceeds from 914 to 920. At 920, the dispenser control system 100 determines whether insulin delivery should be suspended. For example, the dispenser control system 100 may determine that insulin delivery should be suspended when a current indication of a blood glucose level is below a threshold level (e.g., 80 mg/dl). The dispenser control system 100 may employ, for example, neural networks, look-up tables and/or fuzzy logic to determine whether insulin delivery should be suspended.

When the dispenser control system 100 determines at 920 that insulin delivery should be suspended, the method 900 proceeds from 920 to 922. At 922, the dispenser control system 100 signals the user that the blood glucose level is too low, and may be configured to suggest corrective action, such as the consumption of a small meal. The method 900 proceeds from 922 to 924. At 924, the dispenser control system suspends delivery of insulin. The method 900 proceeds from 924 to 914.

When the dispenser control system 100 determines at 920 that insulin delivery should not be suspended, the method 900 proceeds from 920 to 926. At 926, the dispenser control system 100 determines whether additional user input for use in making a bolus correction is desirable. For example, the dispenser control system 100 may determine that additional data is desirable if the blood glucose level is above a threshold level (e.g., 200 mg/dl) and the increase since a last blood glucose level is above a threshold (e.g., the blood glucose level has increased by more than 10 mg/dl since the last reading). The dispenser control system 100 may employ, for example, neural networks, look-up tables and/or fuzzy logic to determine whether additional data from the user is desirable. When the dispenser control system 100 determines at 926 that additional user input is desirable, the method 900 proceeds from 926 to 916. When the dispenser control system 100 determines at 926 that additional user input is not necessary, the method 900 proceeds from 926 to 928.

At 928, the dispenser control system 100 determines whether to administer an automatic bolus correction dose. For example, the dispenser control system 100 may determine to administer an automatic bolus correction dose if an indication of a current blood glucose level is within a threshold range (e.g., between 140 mg/dl and 200 mg/dl) and the change in the indication of a blood glucose level over a period of time exceeds a threshold (e.g., the blood glucose level has increased by more than 10 mg/dl over the proceeding fifteen minutes). The dispenser control system 100 may employ, for example, neural networks, look-up tables and/or fuzzy logic to determine whether to administer an automatic bolus correction dose.

When the dispenser control system 100 determines at 928 to administer an automatic bolus correction dose, the method 900 proceeds from 928 to 930. At 930, the dispenser control system 100 generates control signal to cause the insulin dispenser 104 to dispense a bolus correction insulin dose. The size of the bolus correction insulin dose may be determined based user input, received data, stored data, the size and number of prior bolus doses, or combinations of the above. For example, if no prior automatic bolus correction doses have been administered since the last prandial event, the dispenser control system 100 may generate control signals to cause the insulin dispenser 104 to administer a bolus dose equivalent to a default bolus dose. If the automatic bolus correction dose is a second automatic bolus correction dose since the last prandial event, the dispenser control system 100 may generate control signals to cause the insulin dispenser 104 to administer a bolus dose equivalent to, for example, eighty-percent of a default bolus dose. If the automatic bolus correction dose is a third automatic bolus correction dose since the last prandial event, the dispenser control system 100 may generate control signals to cause the insulin dispenser 104 to administer a bolus dose equivalent to, for example, sixty-percent of a default bolus dose. The dispenser control system 100 may employ, for example, neural networks, look-up tables and/or fuzzy logic to determine the size of an automatic bolus correction dose.

The method 900 proceeds from 930 to 932. At 932, the dispenser control system waits a threshold period of time (e.g., thirty minutes) for the insulin in the bolus dose to work in the individual. After the threshold period of time has elapsed, the method 900 proceeds from 932 to 926.

When the dispenser control system 100 determines at 928 not to administer an automatic bolus correction dose, the method 900 proceeds from 928 to 934. At 934, the dispenser control system 100 determines whether to suspend the dispensing of insulin. For example, the dispenser control system 100 may determine that insulin delivery should be suspended when a current indication of a blood glucose level is below a threshold level (e.g., 80 mg/dl). The dispenser control system 100 may employ, for example, neural networks, look-up tables and/or fuzzy logic to determine whether a blood glucose level is too low.

When the dispenser control system 100 determines at 934 that insulin delivery should be suspended, the method 900 proceeds from 934 to 922. When the dispenser control system 100 determines at 934 that insulin delivery should not be suspended, the method 900 proceeds from 934 to 936.

At 936, the dispensing control system 100 retrieves current and historical blood glucose level data. The method 900 proceeds from 936 to 938. At 938, the dispensing control system 100 calculates the rate of increase in the blood glucose level and the acceleration of the rate of increase in the blood glucose level. The method 900 proceeds from 938 to 940.

At 940, the dispensing control system 100 determines whether there is an indication that a meal has been eaten. The dispensing control system 100 may, for example, determine that there is an indication that a meal has been consumed based on user input, based upon current and historical indications of blood glucose levels, and/or combinations of the above. When the dispensing control system 100 determines at 940 that there is an indication that a meal has been consumed, the method 900 proceeds from 940 to 904. When the dispensing control system determines at 940 that there is no indication that a meal has been eaten, the method 900 proceeds from 940 to 942.

At 942, the dispensing control system 100 determines whether a dangerously high blood glucose condition exists. The dispensing control system 100 may, for example, determine that a dangerously high blood glucose condition exists if an indication of a current blood glucose level exceeds a threshold amount (e.g., 200 mg/dl) and a rate of change of the blood glucose level exceeds a threshold rate of change (e.g., an increase of 10 mg/dl over fifteen minutes). When the dispensing control system 100 determines that a dangerously high blood glucose condition exists, the method 900 proceeds from 942 to 944. At 944, the dispensing control system 100 sets appropriate warning flags or generates appropriate control signals. For example, the dispensing control system 100 may set a flag to cause the output device to sound an alarm. The method 900 proceeds from 944 to 904. When the dispensing control system 100 determines that a dangerously high blood glucose condition does not exist, the method 900 proceeds from 942 to 946.

At 946, the dispensing control system 100 determines whether post-meal correction is desirable. The dispensing control system 100 may, for example, determine that post-meal correction is desirable if an indication of a current blood glucose level exceeds a threshold amount (e.g., 160 mg/dl) and a rate of change of the blood glucose level exceeds a threshold rate of change (e.g., an increase of 10 mg/dl over fifteen minutes). When the dispensing control system 100 determines that post-meal correction is desirable, the method 900 proceeds from 946 to 926. When the dispensing control system 100 determines that post-meal correction is not necessary, the method 900 proceeds from 946 to 948.

At 948, the dispensing control system 100 fuzzifies the blood glucose level, the blood glucose rate and the blood glucose acceleration. This may be done, for example, by assigning the fuzzy coverings of Table One to ranges of blood glucose levels, blood glucose rates of increase, and blood glucose rates of acceleration. The method 900 proceeds from 948 to 950.

At 950, the dispensing control system 100 applies fuzzy logic rules to determine a fuzzy insulin control dose. For example, the dispensing control system 100 may apply the fuzzy logic rules illustrated in Table One. The method 900 proceeds from 950 to 952. At 952, the dispensing control system 100 determines the insulin dose by defuzzifying the fuzzy insulin control dose. The method proceeds to 954. At 954, the dispensing control system 100 optionally adjusts the insulin control dose based on personal information regarding the individual. For example, it may be desirable to adjust the dosage based on the weight of an individual. The method 900 proceeds from 954 to 956. At 956, the dispensing control system 100 displays the recent blood glucose history and the adjusted insulin control dose, and may wait a threshold period of time to allow the user to intervene. The method 900 proceeds from 956 to 958. At 958, the dispensing control system 100 generates control signals to cause the insulin dispenser 104 to dispense the adjusted insulin control dose. The method 900 proceeds from 958 to 934.

Embodiments of the method illustrated in FIGS. 9A through 9C may contain additional acts not shown in FIGS. 9A through 9C, may not contain all of the acts shown in FIGS. 9A through 9C, may perform acts shown in FIGS. 9A through 9C in various orders, and may combine acts shown in FIGS. 9C through 9C. For example, the method 900 may be modified to perform act 912 after act 920. In another example, the method 900 may be modified to monitor active insulin levels and to suspend dispensing of insulin when an active insulin level exceeds a threshold level. In another example, the method 900 may be modified to employ, for example, a look-up table or a neural network to determine the adjusted insulin control dose, in addition to, or instead of, employing fuzzy logic rules. In another example, the method 900 may be modified to combine acts 914 and 926. In another example, the method 900 may be modified to proceed from act 924 to act 904. In another example, the method 900 may be modified to proceed from act 940 to act 926 when it is determined that a meal has been consumed. In another example, the fuzzy logic rules may be adjusted to incorporate patient-specific information, such as weight variations.

Figure 10:
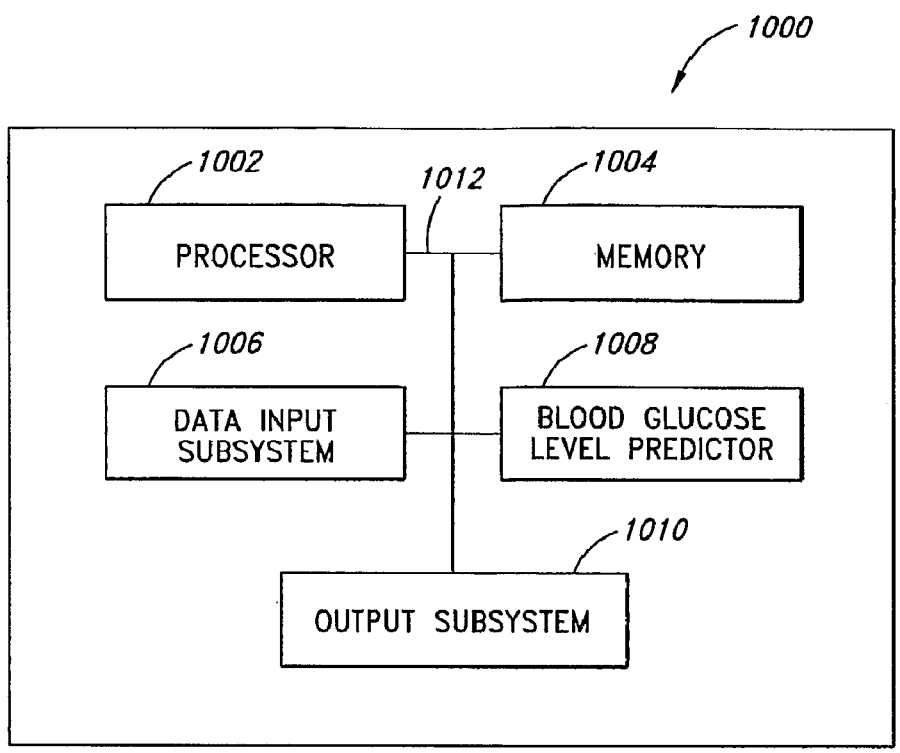
FIG. 10 is a functional block diagram of an embodiment of a system for predicting and controlling blood glucose levels.
Figure 11:
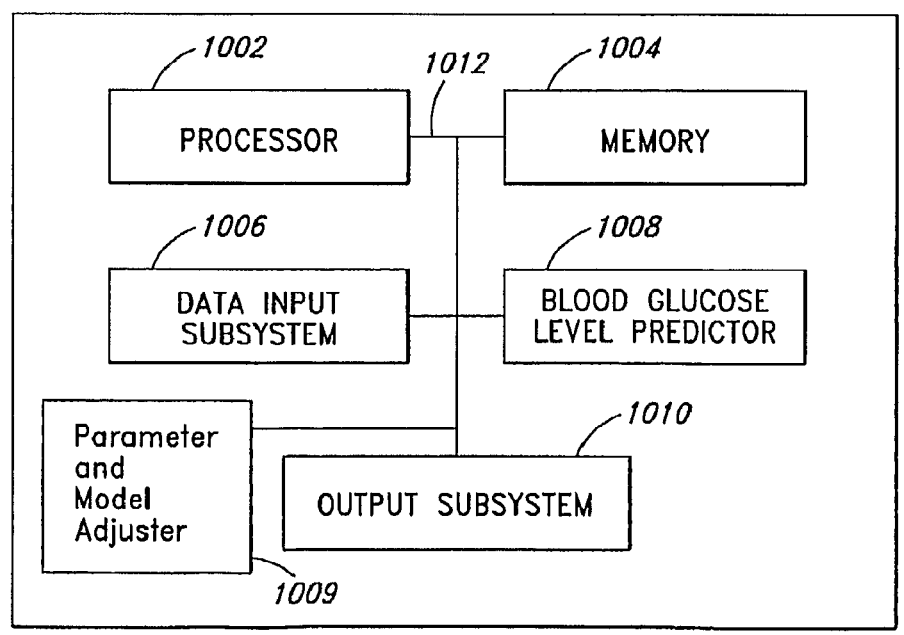
FIG. 11 is a functional block diagram of an embodiment of a blood glucose control system.

FIG. 10 is a functional block diagram of an embodiment of system 1000 for predicting and/or controlling blood glucose levels. The system 1000 comprises a processor 1002 and a memory 1004, a data input subsystem 1006, a blood glucose level predictor 1008, an output subsystem 1010 and a bus system 1012. FIG. 11 is a functional block diagram of system 1000 for predicting and/or controlling blood glucose levels wherein the system 1000 further comprises a parameter and model adjuster 1009. In some embodiments, discrete circuitry and/or one or more proportional and integral controllers may be employed instead of, or in addition to, the illustrated processor 1002, memory 1004, data input subsystem 1006, blood glucose level predictor 1008, parameter and model adjuster 1009 and output subsystem 1010. As described in more detail below, the system 1000 predicts blood glucose levels based on historical data.

Embodiments of a system and method for predicting blood glucose levels may be stand-alone, or may be incorporated into other systems and methods, such as those described herein. For example, the blood glucose level predictor 1008 may be incorporated into the data system 120 of FIG. 1. In another example, the blood glucose level predictor 1008 may be incorporated into the blood glucose analyzer 166 of FIG. 1. In another example, the blood glucose level predictor 1008 may be incorporated into the control system 140 of FIG. 1. In some embodiments, the predictions may be used to control the dispensing of insulin. In some embodiments, the predictions may be compared to results and models and/or parameters used in the predictions may be adjusted based on the comparison.

Figure 12:
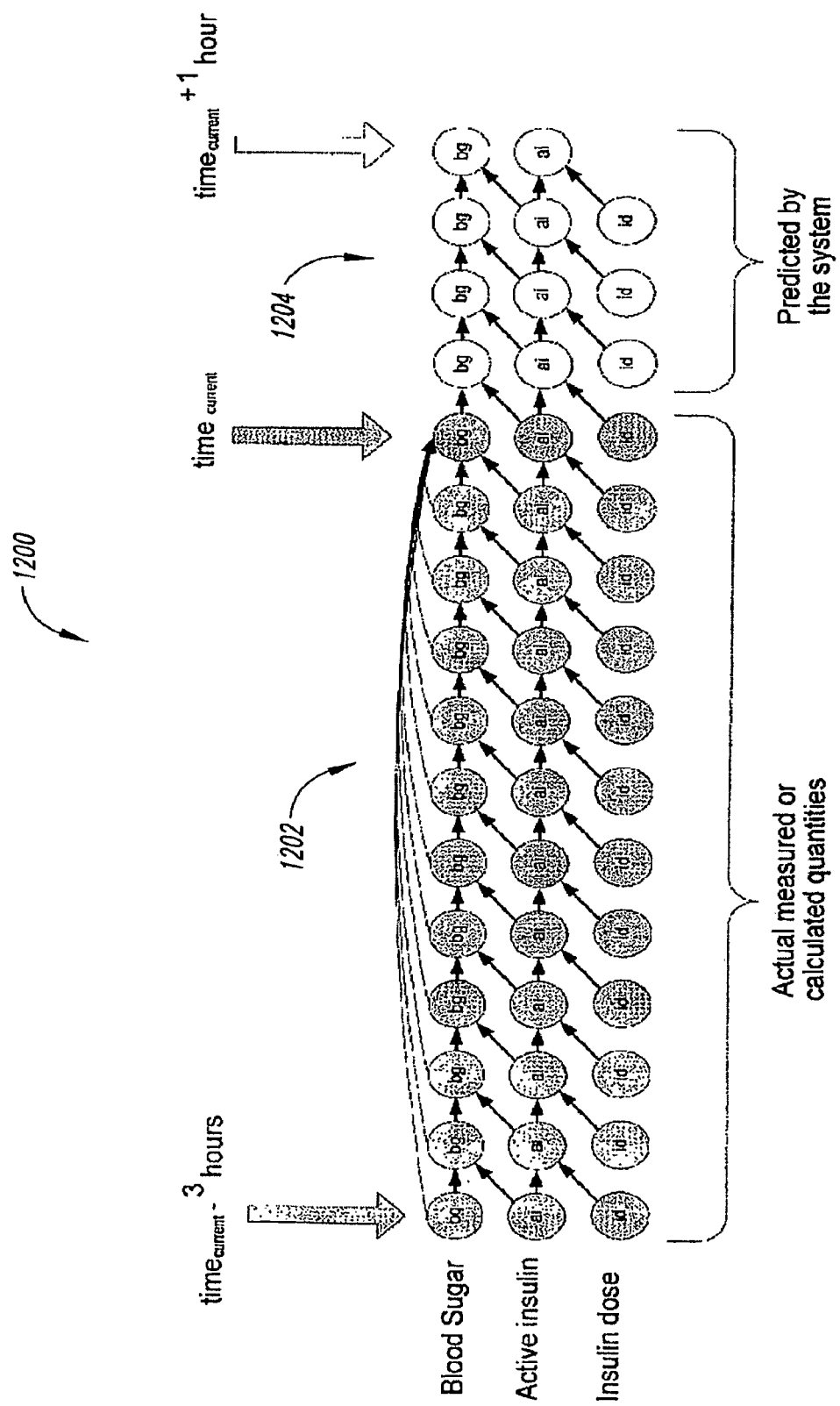
FIG. 12 illustrates an embodiment of a method of predicting blood glucose levels.

FIG. 12 illustrates an embodiment of a method 1200 of predicting blood glucose levels. The 15-minute sample time, and the 1-hour future prediction times are examples only. The method may employ arbitrary fixed and non-fixed blood sugar sample times and may predict arbitrarily far into the future. As illustrated, a blood sugar (bg) state depends upon the previous 12 sampled bg states 1202 (3 hours at 15 minute sample time) and the last calculated active insulin state (ai) state. The method predicts the next four bg states 1204, or the states for the next hour.

As a standalone system the Blood Glucose Prediction method could be used to prevent episodes of hypo- and hyper-glycemia by alerting the patient early enough so that they can manually adjust the insulin themselves. In this implementation, the Blood Glucose Prediction system could be resident on an automated blood sugar sensor device or an insulin infusion pump, for example. More generally, as a component of an integrated system, the Blood Glucose Prediction method could be resident on a system that included an insulin infusion pump and a blood glucose sensor. In this implementation, the Blood Glucose Prediction method could predict blood sugar as above and also automatically adjust the insulin pump dosing to maintain safe blood sugar levels. In this context the Blood Glucose Prediction system may be a closed-loop, adaptive Blood Glucose Management system. The system could be used, for example, where insulin is infused subcutaneously or intravenously.

In one embodiment, the system provides a novel way to model the behavior of the pancreas with regard to the secretion of insulin. Typically researchers attempt to model insulin and blood sugar behaviors in terms of differential equations. While differential equations produce good results in simulations, they do a poor job at representing real human metabolic behavior.

In one embodiment, the system and method inputs are blood sugar levels and insulin doses, for example, coming from continuous blood glucose monitors (CGM) and insulin infusion pumps respectively. Carbohydrate estimates are not required, but may be utilized in some embodiments. The system and method can be personalized for a patient by initializing the set of blood sugar and active insulin Feature Patterns to conform to that patient.

In one embodiment, the system and method adapts in real-time to the individual patient. Whenever a new actual blood sugar value is read, that value is compared with the previous predicted value to update the parameters of the model so as to make better future predictions. Similarly the coefficients of the Active Insulin polynomial function may be updated in real-time.

In one embodiment, transition probabilities can be incorporated into the system and method. Such probabilities may be generated, for example, by incorporating medical opinions and/or other information regarding the transition probabilities into the Feature Patterns to further enhance system performance. For example, it may be physiologically impossible to transition from some Feature Patterns to others. Initializing those transition probabilities to zero may increase the accuracy of the prediction system.

In some embodiments, system performance can be further improved by the incorporation of more accurate Feature Patterns, without changing the basic prediction mathematics. Straight-line patterns may be used for an initial set.

Figure 13:
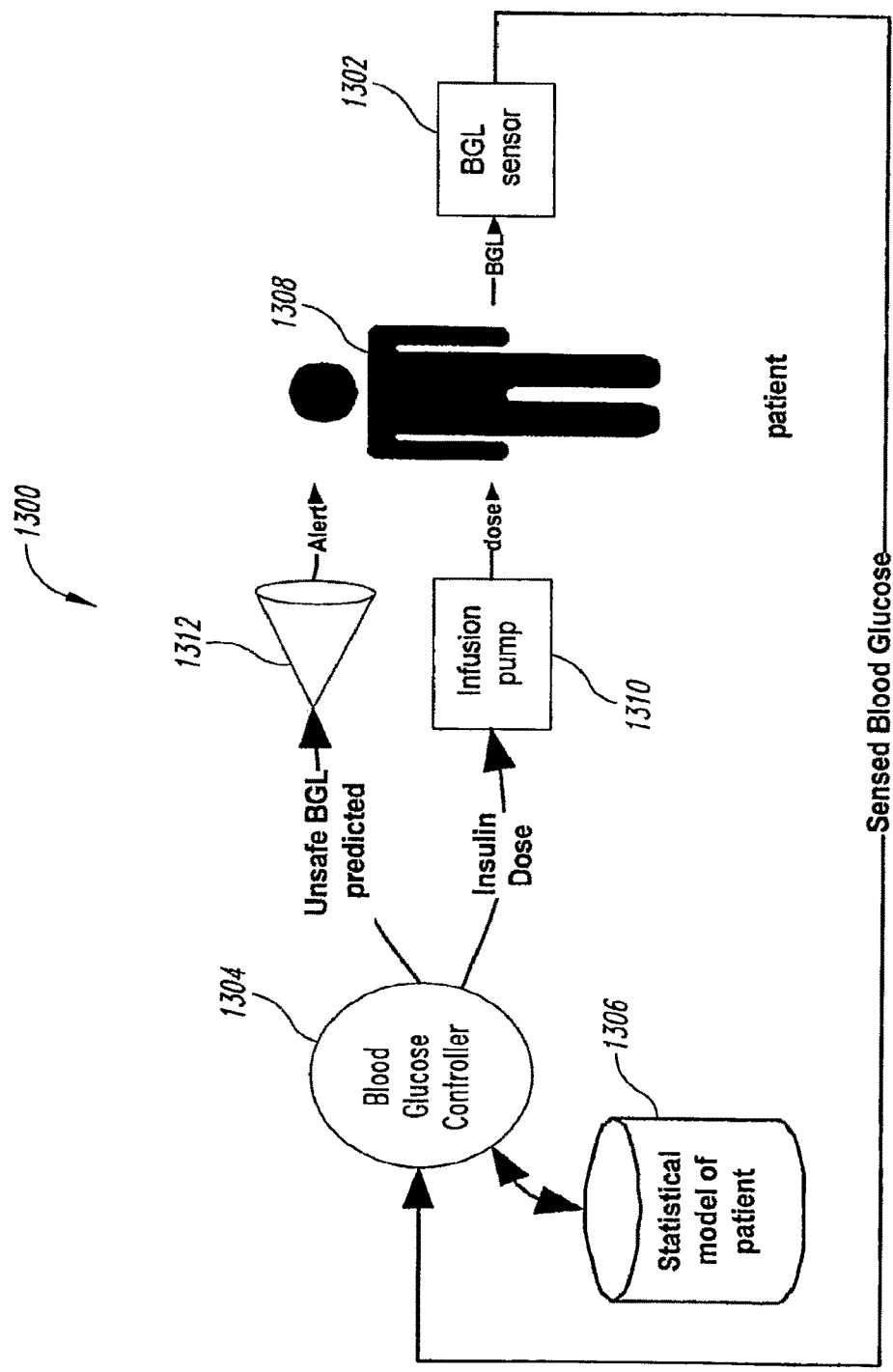
FIG. 13 illustrates an embodiment of a system and method for controlling blood glucose levels.

FIG. 13 illustrates an embodiment of a system and method of operating a system 1300, such as the dispenser control systems 100, 200, 300 illustrated in FIGS. 1-3, to control the dispensing of insulin. A BGL sensor 1302 is configured to sense one or more indications of a blood glucose level of a patient 1308, which may be done using direct or indirect measurement of blood glucose levels. The sensor 1302 is coupled to a blood glucose controller 1304. The blood glucose controller 1304 also is coupled to a data structure 1306. The blood glucose controller 1304 is configured to selectively update the data structure 1306 based on indications received from the sensor 1302 and to selectively generate control signals to cause an infusion pump 1310 to dispense insulin and an alert device 1312 to signal an alert.

An example embodiment of a system and method of predicting blood glucose levels is described below.

The variables employed by the example are:

time. Time is discrete at some interval (e.g., 15 minutes) and is represented by the time variable t, which can be an integer, representing an appropriate time interval. For example, t+1 may be 15 minutes (or any desired interval) later than time t. In the discussion below, the time interval is assumed to be 15 minutes. In other examples, different and/or non-fixed time intervals could be employed. For example, one-hour projection time frames and eight-hour histories are assumed in the discussion below. Other projection time frames and histories could be employed. Variable length projection time frames and histories could be employed. The time periods employed may be adjustable and may be set, for example, by adjusting model parameters. Selection of and changes to the selected time periods may be automated.

Insulin dose, at time t, represented by variable $d_t$. The variable $d_t$ is a real number (between 0 and 30). This range is represented by Dd. Also, $d_t = \{d_t, d_{t-1}, \ldots, d_{t-32}\}$ is the set of previous 8 hours of insulin doses (at 15 minute intervals).

Active Insulin (AI), a variable available at time t. This example uses $a_t$ to represent active insulin. In this example, active insulin represents the cumulated effect of a patient's insulin doses during previous 8 hours, and can be determined by the formula:

$$a_t = \sum_{\tau=0}^{32} d_{t-\tau} f_\tau$$

where $d_t$ is the insulin dose at time t, and $f_\tau$ is the attenuation factor for a dose $\tau$ time steps into the past. The factor $f_\tau$ may be specified by a 6th-order polynomial in $\tau$ given constants $c_0, \ldots, c_6$ which can be tailored for a current patient using, for example, an array lookup table. This example assumes that $f_0 = 1$ and $f_\tau = 0$ for $\tau > 32$. For $0 < \tau \leq 32$, this example assumes that $f_\tau$ is given by the following polynomial:

$$f_\tau = \sum_j c_j \tau^j$$

where $\{c_j\}_j$ are the coefficients of a 6th-degree polynomial given by:
$c_0 = 0.9998$,
$c_1 = 0.045$
$c_2 = -0.184$,
$c_3 = 0.0485$,
$c_4 = -0.005172$,
$c_5 = 0.0002243$,
$c_6 = -0.00000215$.

In this example, AI is a real number between 0 and 50, represented by the range $D_a$. In another embodiment, AI could be quantized to integer values, for example, 500 values representing numbers between 0.0 and 50.0.

Also, $a_t = \{a_t, a_{t-1}, \ldots, a_{t-32}\}$ is the set of previous 8 hours of active insulin levels.

blood glucose level (BGL), at time t represented by the variable $b_t$. In this example, this variable is measured at each time step.

Also, $b_t = \{b_t, b_{t-1}, \ldots, b_{t-32}\}$ is the set of previous 8 hours of blood glucose levels.

In this example, BGL is an integer between 30 and 999 (although with this many integer values, it may be useful to represent this as a continuous variable in other embodiments). The domain of (set of possible values for) $b_t$ is represented by db. BGL values may be viewed as representing a range. For example, a value of 80 may represent a range of values and a value of 300 another range of values. When BGL values are viewed as representing a range, it may be viewed as having fewer values. For example, it may be viewed as having 30 values if 30 ranges are represented.

Embodiments can predict $b_\tau$ for $\tau > t$, i.e., predict future values of blood glucose levels. This example assumes that for all times up to and including t, the true blood glucose levels are known. In the discussion below, $b_t$ is the blood glucose level at time t, and $\hat{b}_t$ is the previously predicted blood glucose level at time t. In some embodiments, $b_t - \hat{b}_t$ could be used as a corrector for the model.

In some embodiments, online adaptation may be employed. For example, whenever a new actual value of $b_t$ comes in, that actual value and the previous predicted value $\hat{b}_t$ could be used to update the parameters of the prediction system and method, so as to make better future predictions. For ease of description, some of the systems and methods are described with reference to a non-adaptive case, but could be generalized to the online adaptive case.

Embodiments of the system and method may employ a statistical model (such as an HMM or some variant) that is good at predicting the future values of BGL given information up to and including time t. Note that the information up to time t may include the actual values of the BGL array $b_t$, the active insulin array $a_t$, and the previous dose array $d_t$. Some embodiments may include a previous predicted blood glucose level $\hat{b}_t$ or an array of previously predicted blood glucose levels. In this example, four future blood glucose levels will be predicted at 15 minute intervals. A probability model will be produced, specifically a model that gives $p(b_\tau, a_t, d_t)$ for $\tau > t$. For a 15-minute interval and a one-hour prediction window, $b_\tau$ will be estimated for $$\tau \in \{t+1, t+2, t+3, t+4\}.$$

An embodiment is not required to use all of this information for conditioning. For example, the insulin dose information could be dropped to produce a model $p(b_\tau | b_t, a_t)$ that depends on BGL and AI if desired. In some embodiments, additional information may be used for conditioning. For example, the previously predicted blood glucose level may be added to produce a model $p(b_\tau | b_t, a_t, d_t, \hat{b}_{t_1})$. Additional information may be used in some embodiments to, for example, increase the accuracy of the predictions and/or selected dosing levels. Less information may be employed in some embodiments to, for example, decrease computation time and/or processing requirements, such as hardware requirements.

For example, a most likely BGL at time $\tau$ may be predicted according to:

$$b_\tau^* = \underset{b_t \in D_b}{\operatorname{argmax}} p(b_\tau \mid b_t, a_t, d_t)$$

The above approach treats the prediction as a classification problem and predicts a most probable value.

Alternatively, an expected value (i.e., average predicted) BGL at time $\tau$ may be predicted according to:

$$\bar{b}_\tau = E[b_\tau \mid b_t, a_t, d_t] = \sum_{b_\tau} b_\tau p(b_\tau \mid b_t, a_t, d_t)$$

This alternative treats the prediction as a regression problem. Blood glucose levels are discrete, and computing the regression estimates may be more computationally complex. A prediction method (for example, the most likely BGL or the expected BGL) may be selected based on empirical evaluation using training and test data for each model that is attempted. Other factors may be considered, such as computational requirement. In some embodiments different methods and/or combinations of methods may be employed.

However the probability model, for example, $p(b_\tau \mid b_t, a_t, d_t)$, is used, there are still a number of ways to implement (i.e., represent and learn) the model given training data. Some examples are discussed below.

Neural Network Solution

In the model $p(b_\tau \mid b_t, a_t, d_t)$, there are a fixed number of variables employed. For example, $b_t$, $a_t$, and $d_t$ are all vectors of a fixed length. Also, in the model, a few different models for r may be employed. (For example, the model may use $\tau_1 = t+1$, up to say 1 hour into the future $\tau_4 = t+4$).

One method that may be employed is to use four static models instead of a dynamic model. For example, for each $\tau_i$; i=1 ... 4, produce a separate predictor. This approach has the advantage that it is relatively easy to implement. Also, this approach does not require design of a large collection of features, since the equivalent "features" are learned automatically by the learning process. However, this approach may not be as easily generalized to other queries (i.e., given these models, computing other forms of probability query, such as, for example, $\tau_5 = t+5$, may be more difficult). In addition, these models may be less easily used with variable length input (for example, predictions with something different than the previous 8 hours).

In the example model, a single function g is produced and trained that maps from the input $b_t$, $a_t$, $d_t$ directly to a distribution on the output, of the form $$p(b_\tau \mid b_t, a_t, d_t) = g_w(b_\tau \mid b_t, a_t, d_t)$$

where W is a collection (vector) of parameters. A 3-layer multilayer perceptron (MLP) that is trained using stochastic gradient descent may provide an easy to use, yet still powerful and general, form of a model.

Two matrices of weight parameters $W_{i2h}$ (the input to hidden weights) and $W_{h2o}$ (the hidden to output weights) are produced. The input may be represented using the vector $$x_t = (b_t, a_t, d_t),$$

and the corresponding output as $$y_t = b_\tau$$

for notational simplicity. The form of the function is as follows:

$$p(y_t \mid x_t) = g_{h2o}(W_{h2o} g_{i2h}(W_{i2h} x_t))$$

where $g_{i2h}(\ )$ is a vector sigmoid function, namely it maps the vector $W_{i2h} x_t$ to a vector of outputs. Each sigmoid function maps a vector to a scalar and form:

$$g_{i2h}(z) = \frac{1}{1 + e^{\alpha z}}$$

where $\alpha$ is a vector of parameters, and in the case above, there is a set of K sigmoids, one for each element of the vector $W_{i2h} x_t$. The power of an MLP approach in fact is this parameter K, the larger the K the more powerful the classifier becomes, but also the more training data that is needed.

The 2nd function $g_{h2o}$ is a "softmax" function that maps its input vector as follows for the $i^{th}$ output:

$$g_{h2o}^i(z) = \frac{e^{\alpha_i z}}{\sum_i e^{\alpha_i z}}$$

This form may be trained using simple stochastic gradient descent (for example, adjusting the parameters of the model incrementally by repeatedly adding the derivative of a cost function to the weight vector).

The input, $x_t$, may be represented in a number of ways. In the example case, $x_t$ is a mix of variables. If $x_t$ consisted of $b_t$ and $a_t$, then it would have $30^{32} \times 500$ possible values (32 input variables each with 30 possible values and an additional input variable with 500 values). For example, $x_t$ could be encoded by encoding each variable (for example, use 5 bits for each 30-valued variable, and 9 bits for the 500-valued variable). Each variable value could be represented by a vector of inputs to the MLP corresponding to the pattern of 1s and 0s that encode its binary number. This produces an MLP that has

32·5+9=169, which is reasonably small for a neural network. Another way of encoding the MLP is to use the inputs directly, leading to 32+1=33 inputs. In this last case, it may be more advantageous to use more of the inputs. For example, $b_t$ and $a_t$ as well as all of $a_t$ and possibly $d_t$ as the input. This approach uses at least 4 separately trained models, one for each value of $\tau$.

Dynamic Model Solution

A dynamic model is one that models the entire sequence of variables. For example, let's suppose that there are a total of T time steps. This may be modeled as a joint distribution of the form:

$$p(b1, b2, \ldots, b_T, a1, a2, \ldots, a_T, d_1, d_2, \ldots d_T)$$

A model like an HMM, Dynamic Bayesian Network (DBN), or some form of dynamic graphical model may be employed. An advantage of a dynamic model is that, during training, the variables may be observed, which provides an opportunity for training procedures which might otherwise not be available.

One example model would use a set of patterns or curves designed to match aspects of a blood glucose history. It may include indicator "features" for each such pattern that indicated how well the current $b_t$ matched a given pattern.

Assume a collection of I temporal patterns $\phi_i(\tau)$ for $\tau = 0, \ldots, L_i$, where $L_i$ is a length of an $i^{th}$ pattern. For example, an 8-hour pattern may have a length of 32. Patterns may correspond to any length of observation of a variable or variables. In the training example discussed below, the values of $b_t$, $a_t$ and $d_t$ will be observed for time points up to and including time t.

When predicting into the future, $b_t$, $a_t$, $d_t$ will be known for points up to and including time t, but values for $\tau > t$ will not be known. When computing $b_\tau$ in the future by more than one time step, the length of these patterns may significantly impact the computation time and processing requirements, particularly when several steps into the future are computed. Fortunately, computing only a limited number of steps into the future may provide useful results. Several example solutions for predicting four steps into the future will be outlined below.

A set of features (or patterns) may be selected for use, along with uses for particular features or patterns in the set. For example, a given pattern may be compared for how well it matches to a current blood glucose history at a time t by using a simple dot product, as follows:

$$\Phi_i(t) = \sum_{\tau=0}^{L_i} \phi_i(\tau) b_{t-\tau} = \|\phi_i\| \|b_t\| \cos\theta$$

where θ is the angle between the two vectors $\phi_i$ and $b_t$. If $b_t$ is exactly the same, then the dot product will have a large value, but if the features are pointing in very different (orthogonal) directions, then cos θ will be small, leading to a small dot product.

In one approach, a large number of features or patterns may be in the set, for example, several thousand patterns. This corresponds to a "pre-warped" case, meaning that the patterns/curves are pre-warped to be all of the interesting shapes that might occur.

One alternative approach is to use a smaller number of patterns, for example 8 patterns, and treat them as pattern "templates" or "mother curves" which act as an exemplar for all other possibly warped curves. In this alternate approach, dynamic time warping may be employed in the calculation of the $\Phi_i(t)$ function. This dynamic time warping calculation may require another set of parameters, which may need to be learned. This alternative approach is more complicated.

The above feature functions $\Phi_i(t)$ so far only relate BGL levels to each other at different times. That is, the $\Phi_i(t)$ features are functions only of present and past values of BGL. The AI values may be utilized and "interact" with BGL values. There are several ways to do this, but regardless of how it is done, indicator-like feature functions (similar to the above dot-product features) may be utilized that express some important joint property among the variables $b_t$ and (at least) $a_t$. These features may be designed by a medical professional. A collection of such feature functions incorporating $a_t$ (and possibly other values such as dosing information) may be designated $\Psi_j(t)$. The variable j denotes that this is the $j^{th}$ feature, and that it applies at time t. Further, J such features may be employed. This means that for each j, $\Psi_j(t)$ is some fixed function of $a_t$, and possibly of some past values of AI and BGL as well (and if it is so desired, past and current values of dose).

All the feature functions $\Phi_i(t)$ for i=1 . . . I and $\Psi_j(t)$ for j=1 . . . J are deterministic, meaning they are fixed functions of past values of AI, BGL, and possibly dose. There are no learned parameters associated with these features. The learned parameters may be used to determine which (combination of) features are most important to predict future values of BGL.

For each feature $\Phi_i(t)$, one parameter $\lambda_i$ may be employed, and for each feature $\Psi_j(t)$, one parameter $y_j$ may be employed. These parameters are applicable for all time t. Each such parameter expresses how important the corresponding feature is at predicting BGL. A joint probability model (again ignoring dose $d_t$ for the moment) may be represented as:

$$p(b_1, b_2, \ldots, b_T, a_1, a_2, \ldots, a_T) = \frac{1}{Z} \prod_{t=1}^{T} \exp\left(\sum_i \lambda_i \Phi_i(t) + \sum_j \gamma_j \Psi_j(t)\right)$$

Given observed sequences of these values, there are a number of ways to train the parameters $\{\lambda_i\}_{i=1}^{I}$ and $\{\gamma_j\}_{j=1}^{J}$. For example, stochastic gradient descent (for example, the MLP above), or a perceptron algorithm may be employed. The stochastic gradient descent method described in "Adoptive Probabilistic Networks with Hidden Variables", by John Binder, et al., Machine Learning Journal, Volume 29, Numbers 2-3, November 1997, pages 213-244; the gradient descent methods and principles described in "A self-tuning method of fuzzy control by descent method," by Nomura, H., et al., Proc. of the IFSA'91 (1991), pp. 155-158; and "An Improved Self-Tuning Mechanism of Fuzzy Control by Gradient Descent Method," by Habbi, A., et al., Foundations for Successful Modeling & Simulation, 17th European Simulation Multiconference (2003), pp. 43-47, may be employed. The perceptron algorithm may be easier to use, but gradient descent methods may produce better results.

In one example embodiment, active insulin (AI) and blood glucose (BGL) data, such as histories, may be used as training data. Some embodiments may employ different and/or additional data and/or data histories as training data. In this example, a large collection of training data is available and the training data are used to select parameter values for a learning method. A large collection of training data is assumed. The training data may be used to determine the best parameter values for the learning algorithms. The training data in this example is a set of sequences of BGL and AI values. That is, D is a set of training data that may be notated as:

$$D = \{(b_{1:T_1}, a_{1:T_1}), (b_{1:T_2}, a_{1:T_2}), \ldots, (b_{1:T_M}, a_{1:T_M})\}$$

which means there will be M separate independent sequences of training data, and that the $m^{th}$ training sequence has time length $T_m$ (which means that each sequence may have a different time length).

In order to simplify notation even further, the parameters $\{\lambda_i\}_{i=1}^{I}$ and $\{y_j\}_{j=1}^{J}$ may be bundled into one long I+J-length vector called A. Also, the feature functions, $\Phi_i(t)$ for i=1 . . . I and $\Psi_j(t)$ for j=1 . . . J, may be bundled into one long I+J-length vector-valued function h(t). This means that the dot-product λh(t) is well-defined (λh(t) is just a scalar value), and that the probability model may be represented using the following notation:

$$p(b_1, b_2, \ldots, b_T, a_1, a_2, \ldots, a_T) = \frac{1}{Z} \prod_{t=1}^{T} e^{\lambda h(t)} = \frac{1}{Z} \exp\left(\sum_{t=1}^{T} \lambda h(t)\right)$$

where $$Z = \sum_{b_{1:T}, a_{1:t}} \exp\left(\sum_{t=1}^{T} \lambda h(t)\right)$$

Note that Z does not need to be computed, thus avoiding significant computational issues, and that Matlab™-like notation may be employed: $b_{1:T} = (b_1, b_2, \ldots, b_T)$ and $a_{1:T} = (a_1, a_2, \ldots, a_T)$. As defined above, each feature function h(t) involves BGL and AI values only up to and including time t—this means that h(t) does not involve any variables for times greater than t, as defined.

The learning with the training data D may be used to adjust the parameters λ so that the data are best represented by the parameters. The learning may include computing the most probable values of future (over the next hour) BGL levels. Some example methods that may be employed to compute the most probable values are summarized below, and subsequent material describes various learning procedures.

Assume that the current time (now) is to. The most probable values of $b_\tau$ for $\tau=t_0+1$, $\tau=t_0+2$, $\tau=t_0+3$, and $\tau=t_0+4$ (i.e., up to one hour into the future assuming 15-minute time steps) may be computed. The values of BGL and AI up to and including time to are known. The following probability model may be employed:

$$p(b_1, b_2, \ldots, b_\tau, a_1, a_2, \ldots, a_\tau) = \frac{1}{Z}\prod_{t=1}^{\tau} e^{\lambda h(t)}$$

for any desired τ.

For notational simplicity, $t_1=t_0+1$, $t_2=t_0+2$, $t_3=t_0+3$, $t_4=t_0+4$. Therefore, the estimated value of $b_{t_1}$, which may be denoted as $\hat{b}_{t_1}$, may be determined according to:

$$\hat{b}_{t_1} = \underset{b_{t_1} \in D_b}{\operatorname{argmax}} p(b_{t_1} \mid b_t, a_t)$$

$$= \underset{b_{t_1} \in D_b}{\operatorname{argmax}} p(b_{t_1}, b_t, a_t)$$

$$= \underset{b_{t_1} \in D_b}{\operatorname{argmax}} \sum_{a_{t_1}} p(b_{t_1}, a_{t_1}, b_t, a_t)$$

The second equality holds because $p(b_t, a_t)$ is a constant when taking the maximum over $b_{t_1}$. The third equality holds when the sum is computed over the AI values to obtain a marginal distribution that does not involve $a_{t_1}$. The value of $a_{t_1}$ is not known yet because the dose at time ti is not known.

Alternatively, because AI is related using a formula to the current dose time t, and if the dose at time $t_1$ is known, the value of AI at time ti may be known and the following computation may be employed:

$$\hat{b}_{t_1} = \underset{t_1 \in D_b}{\operatorname{argmax}} p(b_{t_1}, a_{t_1}, b_t, a_t)$$

where in this last form, $a_{t_1}$ is the computed value of $a_i$ computed based on the current dose.

In this example, BGL is predicted not only for time $t_1$ but also for times $t_2$ through $t_4$. One probabilistic way to do this would be to compute predictions of BGL at all times $t_1$ through $t_4$ simultaneously (i.e., jointly).

This may be represented as follows:

$$(\hat{b}_{t_1}, \hat{b}_{t_2}, \hat{b}_{t_3}, \hat{b}_{t_4}) = \underset{b_{t_1} \in D_b}{\operatorname{argmax}} \underset{b_{t_2} \in D_b}{\operatorname{argmax}} \underset{b_{t_3} \in D_b}{\operatorname{argmax}} \underset{b_{t_4} \in D_b}{\operatorname{argmax}} p(b_{t_1}, b_{t_2}, b_{t_3}, b_{t_4} \mid b_t, a_t)$$

This computation would require $O(r^4)$ computational steps, where $r=|D_b|$. The model $$p(b_{t_1}, b_{t_2}, b_{t_3}, b_{t_4} \mid b_t, a_t)$$

may be determined according to:

$$p(b_{t_1}, b_{t_2}, b_{t_3}, b_{t_4} \mid b_t, a_t) \alpha p(b_{t_1}, b_{t_2}, b_{t_3}, b_{t_4}, b_t, a_t) =$$

$$\sum_{a_{t_1}}\sum_{a_{t_2}}\sum_{a_{t_3}}\sum_{a_{t_4}} p(b_{t_1}, a_{t_1}, b_{t_2}, a_{t_2}, b_{t_3}, a_{t_3}, b_{t_4}, a_{t_4}, b_t, a_t)$$

Again, since $p(b_t, a_t)$ is a constant when taking the maximum over $b_{t_1}$, something that is proportional to the conditional probability (which is the reason for the proportional sign in the equation above) may be employed. The right-hand-side requires computation of $O(s^4)$, where $s=|D_a|$.

From the previous discussion, when $r=30$, $r^4 \approx 800{,}000$ which is something that is quite feasible for a modern computer to do in a few seconds of compute time. However, $s=500$, so $s^4 \approx 62$ billion steps. While some modern microprocessors could probably do something like this in a few minutes, this may be too computationally complex for some embodiments.

Therefore, as an approximation, a reasonable compromise may be to treat the predicted BGL for a prior time step as an actual BGL for predicting the BGL for the next time step, and then utilize the method mentioned above for all time steps. For example, one of the methods described above may be used to predict the BGL for time $t_1$. Then using the predicted BGL for time ti as an actual BGL, predict the BGL for time $t_2$. Proceeding in this way, the predicted BGL for times ti and $t_2$ may be treated as actual BGLs for predicting the value for $t_3$, and the predicted BGL for times ti, $t_2$ and $t_3$ would be treated as actual BGLs for predicting the for time $t_4$. The computation for predicting BGL using this approximation would only be 4 times the cost of predicting the next time step, significantly reducing processing requirements and facilitating rapid prediction.

An alternative strategy (that would trade off computation and approximation) would be to jointly predict BGL for $t_1$ and $t_2$, and then use the two predicted values when predicting BGL for times $t_3$ and $t_4$. Empirical testing may be employed to determine a particular strategy for use in an embodiment. Multiple strategies may be employed and may vary based on conditions and variables, such as an actual BGL. A look-up table may be employed.

The predicted BGL for times $t_1$ through $t_4$ may be designated $$\hat{b}_{t1}, \hat{b}_{t2}, \hat{b}_{t3}, \text{ and } \hat{b}_{t4}$$

or more succinctly $$\hat{b}_{t_{1:4}}.$$

The actual values of BGL for the future times may be denoted:

$$b_{t_{1:4}}.$$

Perceptron Learning Example

Figure 14:
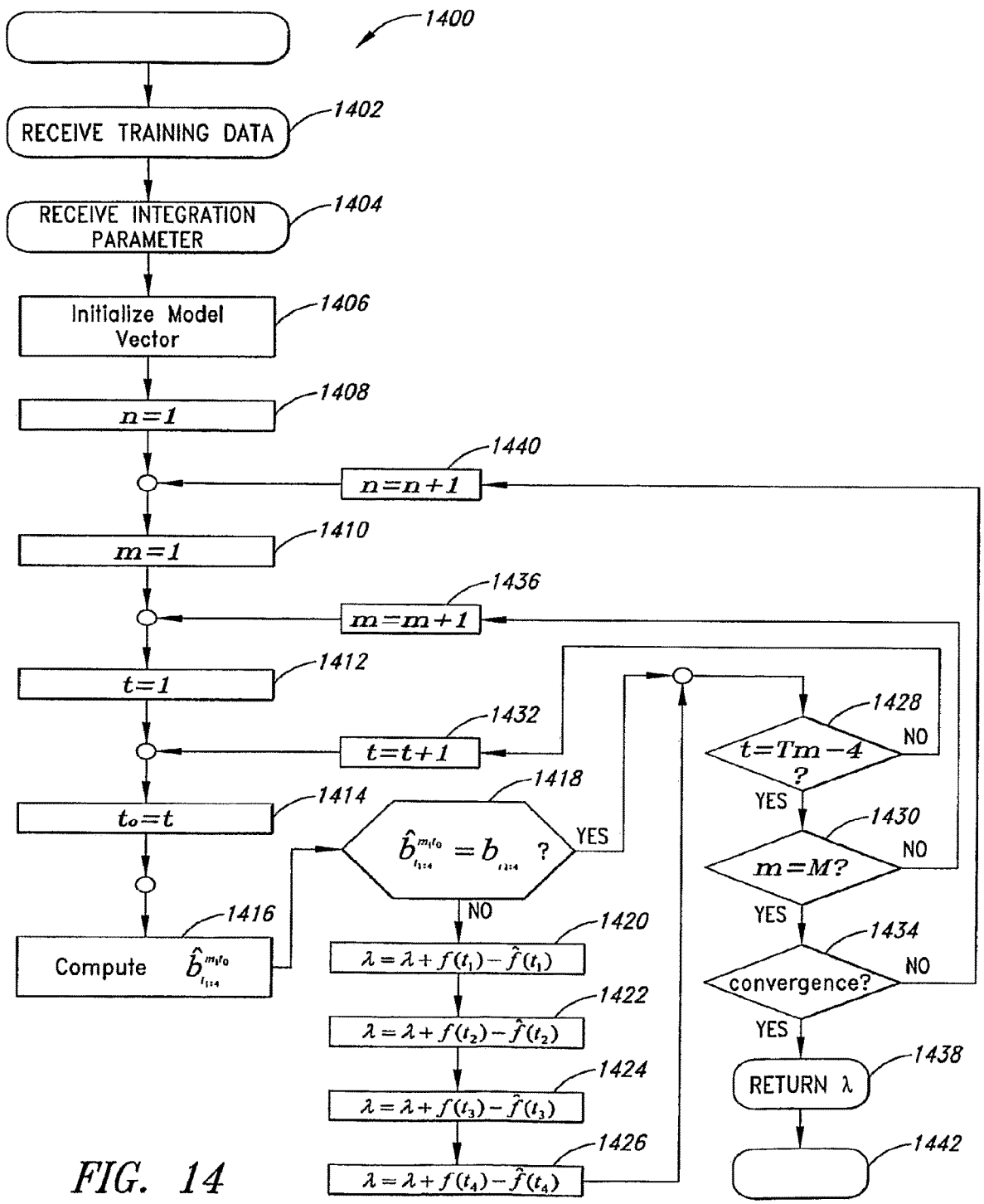
FIG. 14 illustrates an embodiment of a method of training model parameters for a blood glucose control system.

FIG. 14 illustrates a perceptron learning method 1400 that may be employed to training a model used by a system, such as the embodiments described herein. Perceptron learning is a simple method that may work very well for training a model. The value of a parameter serves as an indication of how important the corresponding feature is to the accuracy of the model's predictions. The method 1400 corrects the model when it makes mistakes in predicting $b_{t_{1:4}}$, and leaves the model alone when it does not make mistakes.

At 1402, the system receives or retrieves a set of training data. The set of training data may comprise, for example, a large set of training data. The data set may include, for example, current and historical AI data, BGL data, and dosing data. The method 1400 proceeds from 1402 to 1404.

At 1404, the system receives or retrieves an iteration parameter N. The iteration parameter N may be used to determine when the model is trained. In the illustrated example, N is used to set the number of training passes that are made through the data set. The value of N may be set empirically by observing when additional passes make little or no difference to the value of a model parameter vector. In other words, convergence has occurred. Other methods may be employed to determine when a model is sufficiently trained. For example, changes to a model parameter vector during a pass may be compared to a threshold value or percentage, and the training cycle for the model parameter vector terminated when the changes are less than the threshold. Some embodiments may terminate training of a model when a threshold value or percentage is not exceeded for a threshold number of successive passes. The method 1400 proceeds from 1404 to 1406.

At 1406, the system initializes the model parameter vector for the model to be trained. In this discussion, the model parameter vector to be trained is set to a zero vector. The method 1400 proceeds from 1406 to 1408.

At 1408, the system initializes a counter n for counting a number of passes through the data. The method 1400 proceeds from 1408 to 1410. At 1410, the system initializes a variable m for keeping track of the sample sequence in the data set. The method 1400 proceeds from 1410 to 1412. At 1412, the system initializes a variable t for tracking time periods. The method 1400 proceeds from 1412 to 1414. At 1414, the system sets $t_0$ to t. The method 1400 proceeds from 1414 to 1416.

At 1416, the system computes $\hat{b}_{t_{1:4}}$ for the current $t_0$, and sample m. The method 1400 proceeds from 1416 to 1418. At 1418, the system determines whether $\hat{b}_{t_{1:4}}$ for the current $t_0$, and sample m is equal to $\hat{b}_{t_{1:4}}$. When it is determined at 1418 that $\hat{b}_{t_{1:4}} \neq b_{t_{1:4}}$, the method 1400 proceeds from 1418 to 1420. When it is determined at 1418 that $\hat{b}_{t_{1:4}} = b_{t_{1:4}}$, the method proceeds from 1418 to 1428.

At 1420, the system sets $\lambda = \lambda + f(t_1) - \hat{f}(t_1)$. The method 1400 proceeds from 1420 to 1422. At 1422, the system sets $\lambda = \lambda + f(t_2) - \hat{f}(t_2)$. The method proceeds from 1422 to 1424. At 1424, the system sets $\lambda = \lambda + f(t_3) - \hat{f}(t_3)$. The method 1400 proceeds from 1424 to 1426. At 1426, the system sets $\lambda = \lambda + f(t_4) - \hat{f}(t_4)$. The method proceeds from 1426 to 1428. The vector-valued function $f(\tau)$ is the length J+I vector of feature values up to and including time τ that uses the actual values of BGL and AI. The vector-valued function $\hat{f}(\tau)$ is the length J+I vector of feature values up to and including time τ that uses the actual values of AI but uses the predicted values of BGL. When $\tau = t_1$, then there is only one time point at which a predicted value is needed, namely $t_1$. When $\tau = t_2$, then, like in the case of prediction itself, the predicted values of BGL at time $t_1$ are treated as actual values, and used to predict values for $t_2$. A similar case holds for $t_3$ and $t_4$. If the prediction is incorrect, the parameters are moved away from the wrongly predicted values (by subtracting $\hat{f}(\tau)$) and moved towards the correct values (by adding $f(\tau)$). In the illustrated example, this is done four times, once each for $t_1$ through $t_4$. If the prediction is correct on the current pattern, however, the model is left alone.

At 1428, the system determines whether all desired time periods for the current sample sequence have been included in the setting of the model parameter vector. When it is determined that all desired time periods for the sample sequence have been included, the method proceeds from 1428 to 1430. When it is determined that not all of the desired time periods for the sample sequence have been included, the method 1400 proceeds from 1428 to 1432. At 1432, the system increments the value of t. The method 1400 proceeds from 1432 to 1414.

At 1430, the system determines whether all samples in the data set have been factored into the setting of the parameter. When it is determined that all of the samples in the data set have been included, the method proceeds from 1430 to 1434. When it is determined that not all of the samples in the data set have been included, the method 1400 proceeds from 1430 to 1436. At 1436, the system increments the value of m. The method 1400 proceeds from 1436 to 1412.

At 1434, the system determines whether a convergence criteria has been satisfied. As illustrated, this is done by comparing a loop counter to an iteration control variable N. Other convergence criteria may be employed. For example, thresholds may be employed as discussed above. When it is determined that the convergence criteria is satisfied, the method proceeds from 1434 to 1438. When it is determined that the convergence criteria is not satisfied, the method 1400 proceeds from 1434 to 1440. At 1440, the system increments the value of n. The method 1400 proceeds from 1440 to 1410.

At 1438, the system returns the model parameter vector A, and any other desired variables. The method 1400 proceeds from 1438 to 1442, where further processing may occur.

Embodiments of the method illustrated in FIG. 14 may contain additional acts not shown in FIG. 14, may not contain all of the acts shown in FIG. 14, may perform acts shown in FIG. 14 in various orders, and may combine acts shown in FIG. 14. For example, the method 1400 may be modified to repeat the method and determine a model parameter vector corresponding to another feature or set of features.

Another example of a method of training a model parameter vector is set forth below in the form of a high-level nested loop, which may be implemented in source code and/or compiled and stored in a computer-readable memory medium and used to cause a computing device to perform the method.

INPUT: Training data D as described above.
INPUT: Iteration parameter N
INITIALIZATION: Set λ=0 (the vector of all zeros)
PROCEDURE:
For n=1 . . . N;
For m=1 . . . M; do
For t=1 . . . $T_m$−4; do
Assume $t_0$=t
Compute $\hat{b}_{t_{1:4}}$ for the current $t_0$, and sample m.
If $\hat{b}_{t_{1:4}} \neq b_{t_{1:4}}$; then $\lambda = \lambda + f(t_1) - \hat{f}(t_1)$ $\lambda = \lambda + f(t_2) - \hat{f}(t_2)$ $\lambda = \lambda + f(t_3) - \hat{f}(t_3)$ $\lambda = \lambda + f(t_4) - \hat{f}(t_4)$ Fi.
Done.
Done.
Done.
OUTPUT: The resulting trained parameters λ.

Note that $\hat{b}_{t_{1:4}}$ computed in the algorithm is based on whatever the current training sequence it is (indicated in the algorithm by the value m) even though the letter m is not indicated in the notation $\hat{b}_{t_{1:4}}$, which could have been notated as $\hat{b}_{t_{1:4}}^m$.

Secondly, the values $\hat{b}_{t_{1:4}}$ computed in the algorithm are based on the current time point to, and could have been notated as $\hat{b}_{t_{1:4}}^{m,t_o}$.

The vector-valued function $f(\tau)$ is the length J+I vector of feature values up to and including time $\tau$ that uses the true values of BGL and AI.

The vector-valued function $\hat{f}(\tau)$ is the length J+I vector of feature values up to and including time $\tau$ that uses the true values of AI but uses the predicted values of BGL. When $\tau=t_1$, then there is only one time point at which the predicted values are needed, namely $t_1$. When $\tau=t_2$, then, like in the case of prediction itself, the predicted values of BGL at time $t_1$ are assumed to be correct, and the predicted values for $t_2$ are used. A similar case holds for $t_3$ and $t_4$.

The parameter N is a repetition parameter, which determines how many times through the entire training set the algorithm should go. In general, this parameter may be determined empirically. One way to determine it is to look at the model parameter vector $\lambda$ after a given pass through the training data. If it has not moved significantly, it may be assumed that the algorithm has converged and that it is not worth computing any longer.

Figure 15:
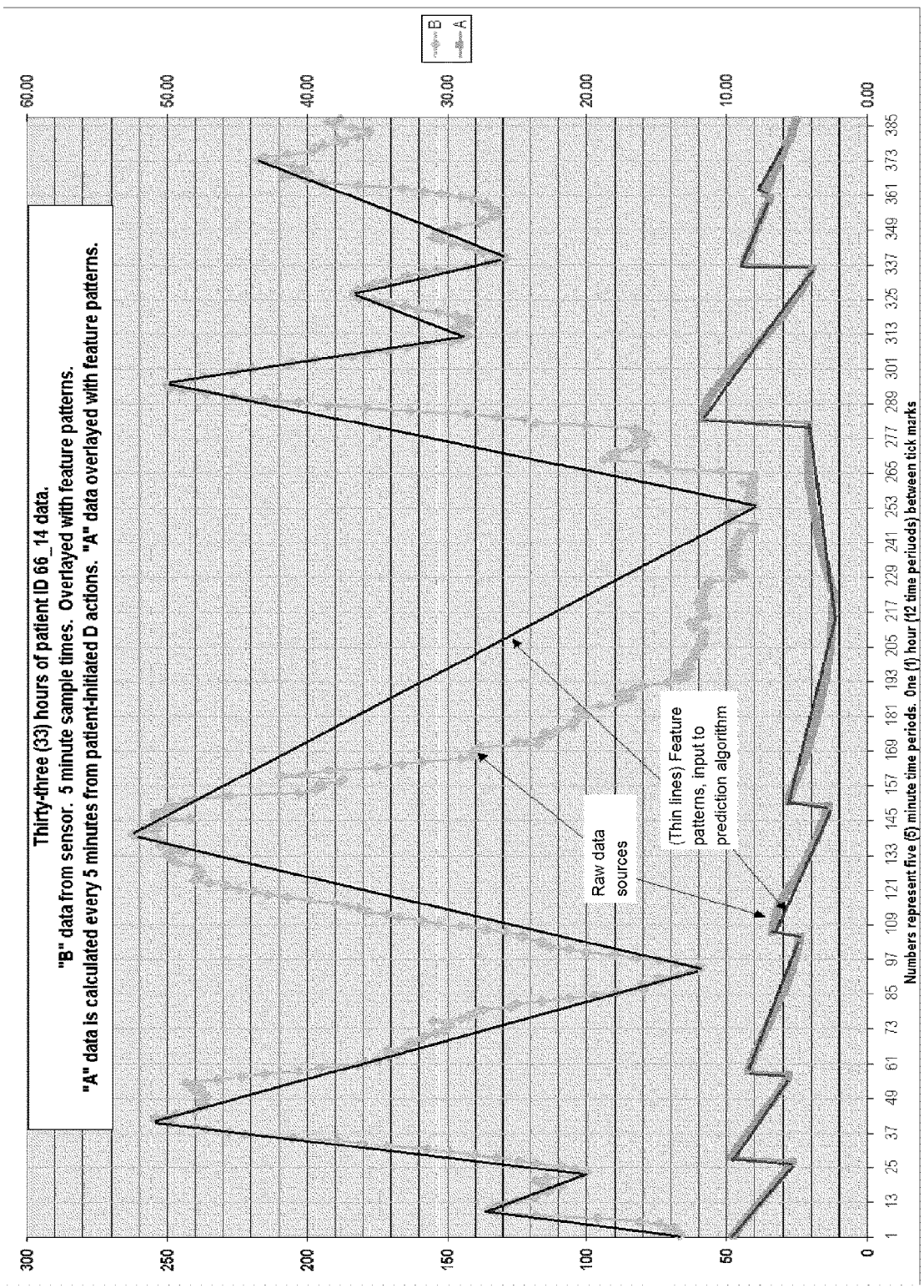
FIG. 15 illustrates an example of input data for an embodiment of a system and method for predicting blood glucose levels.

FIG. 15 illustrates an example data set in accordance with an embodiment of the invention. In the illustrated example, because of the unsynchronized nature of A (Active insulin) and B (Blood sugar) feature patterns, at any given time the A and B feature segments will seldom start and stop at the same sample time point.

Suppose at $T_{curr}$ the last completed B feature pattern ended at $T_{curr}-15$ minutes, i.e., $T_{curr}$ is not a simultaneous Peak or Valley point for both the A and B signals.

Then, the example inputs to the Blood Glucose Prediction method at $T_{curr}$ would be:

1) the actual sequence of B patterns up to $T_{curr}-10$ minutes, and 2) the actual sequence of A patterns up to $T_{curr}-15$ minutes, and 3) the probability distributions of B patterns for the period between $T_{curr}-10$ and $T_{curr}$, and 4) the probability distributions of A patterns for the period between $T_{curr}-15$ and $T_{curr}$.

Figure 16:
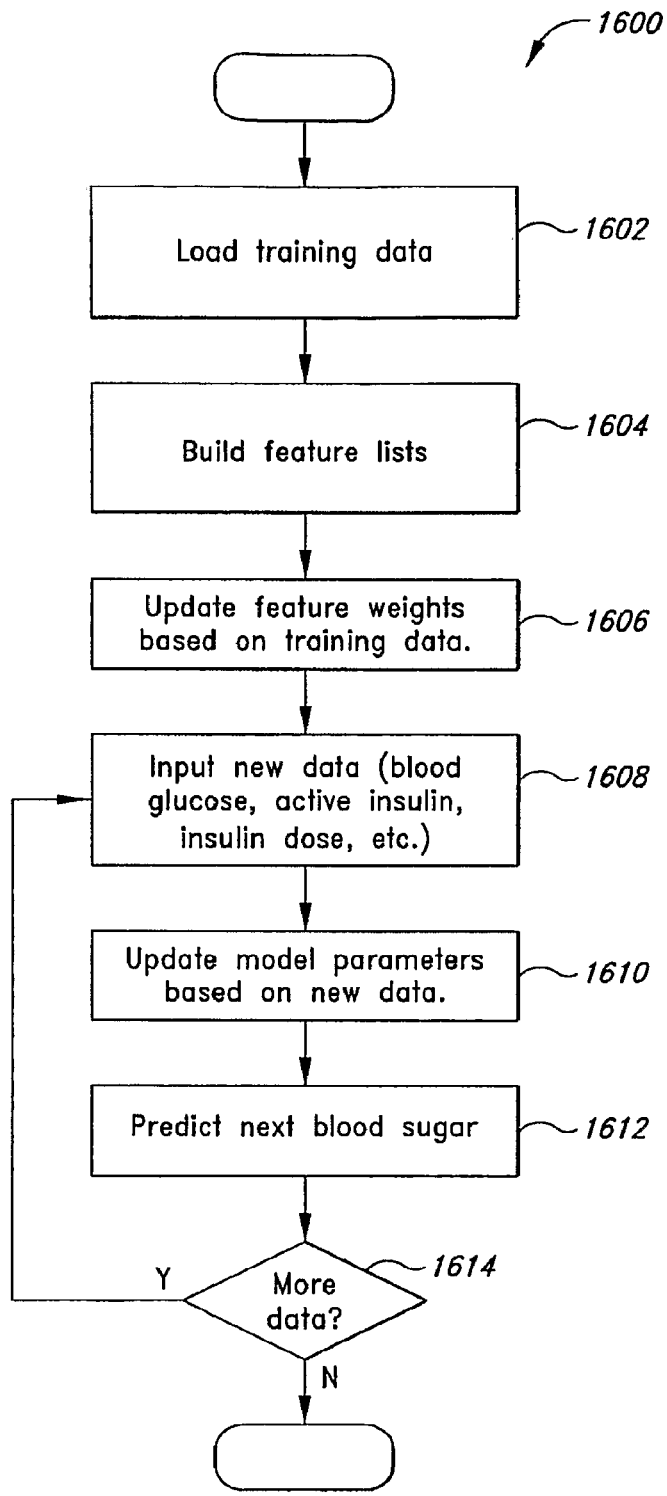
FIG. 16 illustrates an embodiment of a blood glucose prediction method.

FIG. 16 illustrates a mid-level flow diagram of an embodiment of a method 1600 of predicting blood glucose levels that may be employed by a system, such as the dispenser control systems 100, 200 and 300 illustrated in FIGS. 1 through 3. For convenience, the method will be described with respect to the embodiment of a dispenser control system 100 illustrated in FIG. 1. In this example the predicted blood glucose values are restricted to multiples of 30. At 1602 actual training data sequences are received or retrieved by the system 100. Those data may include blood glucose level, active insulin level, insulin dosing data and other data sequences. The method proceeds from 1602 to 1604.

At 1604, blood glucose and active insulin feature lists, which may be predefined, are received, retrieved or built by the system 100. Feature lists may be, for example, in xml format. The method 1600 proceeds from 1604 to 1606. At 1606, the system 100 updates feature weights based on the training data. In this example, a perceptron method is employed. At this point the model is initialized and is ready to accept new data from which blood glucose predictions may be made. The method proceeds from 1606 to 1608.

At 1608, the system 100 senses or receives new blood glucose data. The method 1600 proceeds from 1608 to 1610. At 1610, the system 100 updates the model parameters based on the new blood glucose data. For example, the blood glucose level that was predicted based on the previous blood glucose level measurement is compared with the actual measured blood glucose measurement, at the current time. If the prediction is sufficiently close to the measured value, the model parameters remain unchanged; if not, the parameters are iteratively updated until the model parameters converge. The method 1600 proceeds from 1610 to 1612. At 1612, the system 100 predicts the next blood glucose level, based on the updated model parameters, the current measured blood glucose value, a calculated active insulin value, and possibly other data. The method 1600 proceeds from 1612 to 1614. At 1614, the system 100 determines whether more predictions are desired. For example, the system may determine whether more data has been received in a timely manner. When the system determines that more predictions are desired, the method 1600 proceeds from 1614 to 1608. When the system 100 determines that more predictions are not desired, the method 1600 proceeds from 1614 to 1618, where further or other processing may be performed by the system 100.

Embodiments of the method illustrated in FIG. 16 may contain additional acts not shown in FIG. 16, may not contain all of the acts illustrated in FIG. 16, may combine or separate acts illustrated in FIG. 16, and may perform the acts illustrated in FIG. 16 in various orders. For example, the method 1600 may be modified to update the model parameters until new data is received or expected, and then proceed from 1608 to 1610. The threshold levels and ranges discussed with respect to FIG. 16 may be fixed or may be functions and may be based on statistical analysis.

Figure 17:
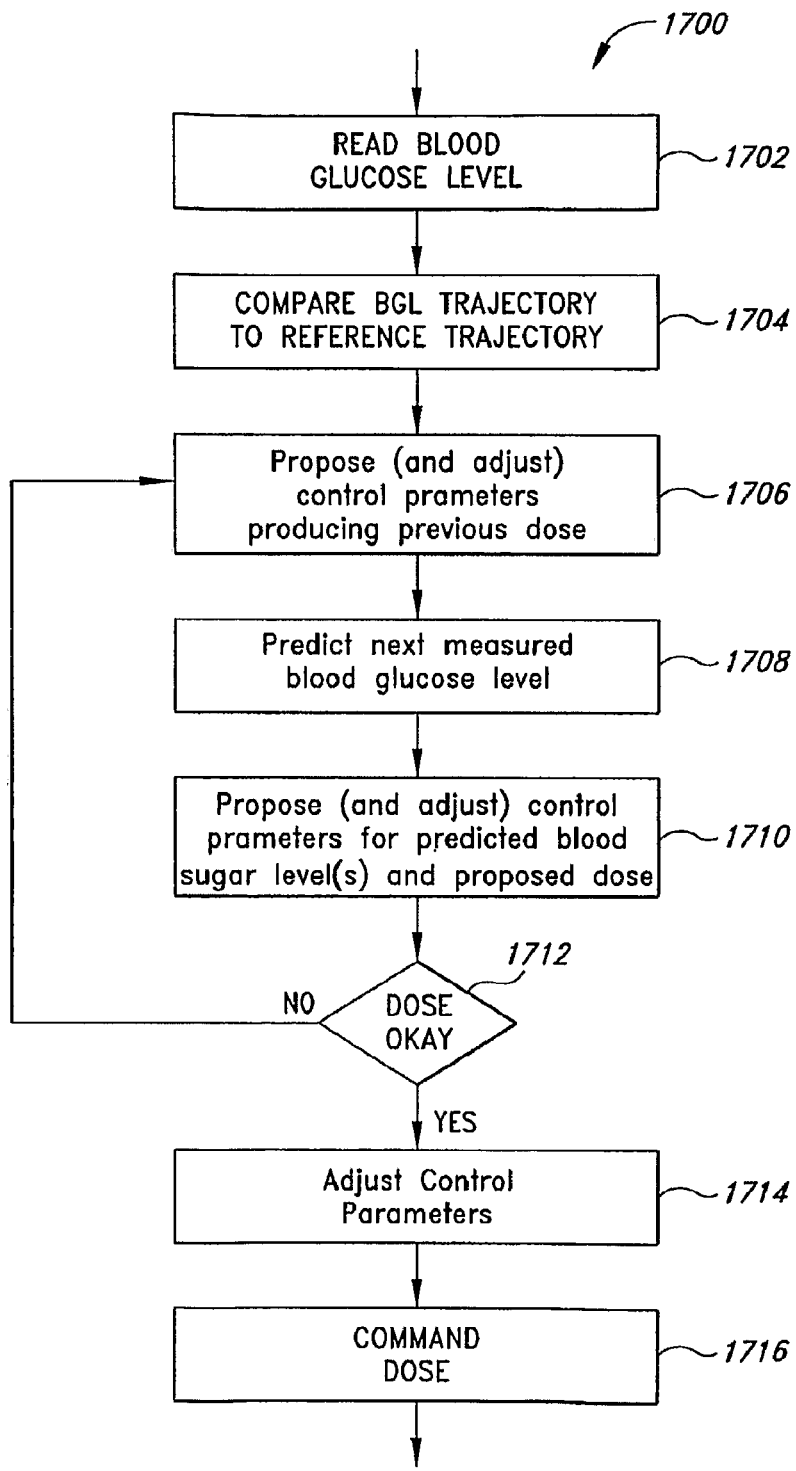
FIG. 17 illustrates an embodiment of a method of controlling an insulin pump that may be employed, for example, by the embodiments described herein.

FIG. 17 illustrates an embodiment of a method 1700 of adjusting system control parameters (for example, by adjusting a model parameter vector) based on measured blood sugar levels which may be implemented in real or near-real time by adjusting the parameters as actual data is received. The method 1700 may be employed, for example, by the systems and methods for controlling the dispensing of insulin, such as the embodiments such described herein. For example, the method 1700 may be employed as a subroutine by an insulin dispensing control system.

At 1702, the system receives, reads or retrieves a blood sugar level. This may be done, for example, at a predetermined rate, such as at 15-minute intervals. The method may employ arbitrary fixed and non-fixed blood sugar sample times and may predict arbitrarily far into the future. The sampling rate may be fixed or may not be fixed, and may vary, for example, based on user input, blood sugar levels, patient history information, the time of day or other data or variables. The blood sugar level may be sensed using a blood glucose sensor, which may sense blood glucose levels directly or indirectly. The blood sugar levels may be stored in a database as part of a history of blood sugar levels, such as a blood sugar history for a particular patient or a database used to train models, including, for example, model parameter vectors, employed by the system. The method 1700 proceeds from 1702 to 1704.

Figure 18:
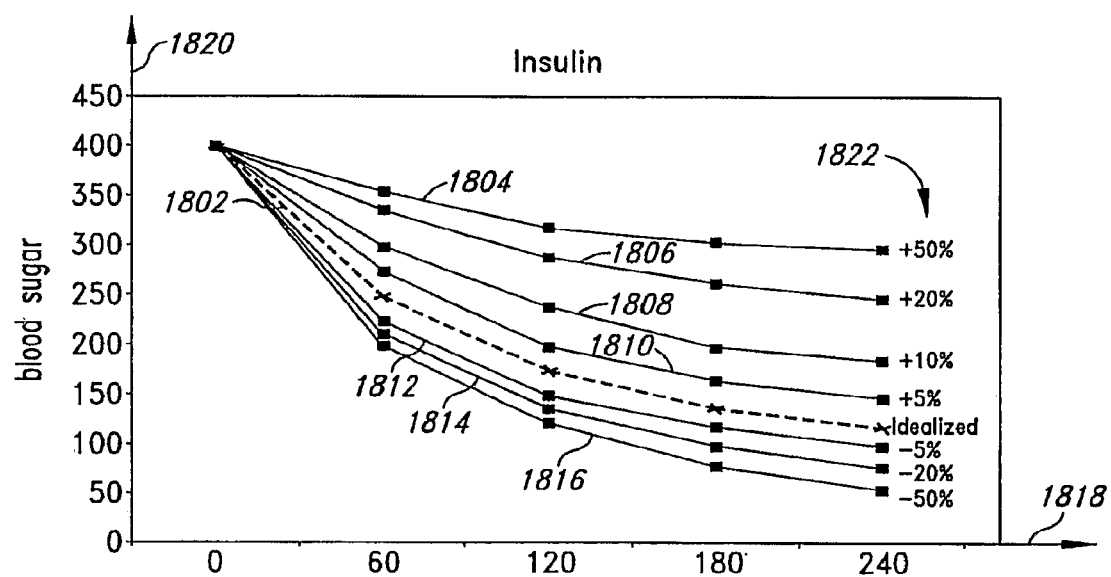
FIG. 18 illustrates blood sugar trajectories and associated correction percentages that may be employed, for example, by the embodiments described herein.

At 1704, the system compares a blood glucose trajectory to a reference blood glucose trajectory. The comparison may include, for example, comparing a blood glucose level, a rate of change of the blood glucose level, an acceleration of the blood glucose level, and/or other attributes pertinent to a patient's blood sugar and insulin states. The blood glucose trajectory may be based on a history for the patient, and may comprise measured and/or predicted blood glucose levels as described herein. The reference blood glucose trajectory may be, for example, a trajectory based on parameters set by a professional, such as a physician, a trajectory based on statistical analysis or models and/or a trajectory based on a combination of set parameters and statistical analysis. FIG. 18 illustrates an idealized trajectory that may be employed. The method 1700 proceeds from 1704 to 1706.

At 1706, the individual control parameters producing the dose for the previous blood sugar sample are adjusted based on the comparison at 1704. Table 4 shows a possible scenario in which the adjustment factor derived at 1604 has a value of 0.2. In this scenario, the ('BV', 'RZ', 'AZ') control parameter, as highlighted, has an initial value of 8.0, resulting from the insulin dose given in response to the previous blood sugar value. In this scenario, the ('BV', 'RZ', 'AZ') control parameter was subsequently adjusted to 9.5, as shown in the second matrix. Control parameter adjustment may go beyond adjusting only the individual parameters that produced the previous dose to include adjustment of the overall fuzzy logic rules matrix shown in FIG. 19. The strategy that defines the overall adjustment of the fuzzy logic rules matrix may be called the dosing matrix coherency policy. An example of that policy is shown in Table 5. The dosing matrix coherency policy may be designed to prevent the occurrences of dosing inconsistencies in the dosing rules matrix. For example, for the same blood sugar value, such as BV, and acceleration, such as AZ, the dose for a higher blood sugar rate, such as RP, should be higher than RZ. In other words, the dose for rule (BV, RP, AZ) should be no smaller than (BV, RZ, AZ), as reflected in the dosing matrix coherency policy and the fuzzy logic rules matrices. See, for example, the fuzzy logic control parameters illustrated in FIG. 19 and the embodiments described herein. See discussion of additional details below. The method 1700 proceeds from 1706 to 1708.

TABLE 4

FUZZY LOGIC DOSING RULES MATRIX ADJUSTMENTS
Before Adjustment of Rule ('BV', 'RZ', 'AZ')

| | rate = VN | | | | rate = RN | | | | rate = RZ | | | | rate = RP | | | | rate = RV | | |
|---|---|---|---|---|---|---|---|---|---|---|---|---|---|---|---|---|---|---|---|
| accl | AN | AZ | AP | accl | AN | AZ | AP | accl | AN | AZ | AP | accl | AN | AZ | AP | accl | AN | AZ | AP |
| BV | 5.0 | 6.0 | 7.0 | BV | 6.0 | 7.0 | 8.0 | BV | 7.0 | 8.0 | 9.0 | BV | 7.0 | 9.0 | 11.0 | BV | 8.0 | 10.0 | 12.0 |
| BH | 1.5 | 2.0 | 4.0 | BH | 3.0 | 4.0 | 6.0 | BH | 3.0 | 5.0 | 7.0 | BH | 5.0 | 7.0 | 9.0 | BH | 6.0 | 9.0 | 10.0 |
| BN | 0.3 | 0.5 | 0.7 | BN | 0.8 | 1.5 | 2.5 | BN | 1.5 | 2.0 | 3.0 | BN | 2.0 | 4.0 | 6.0 | BN | 3.0 | 5.0 | 7.0 |
| BM | 0.0 | 0.1 | 0.1 | BM | 0.1 | 0.3 | 0.4 | BM | 0.3 | 0.5 | 0.8 | BM | 0.5 | 0.8 | 1.0 | BM | 1.0 | 2.0 | 3.0 |
| BL | 0.0 | 0.0 | 0.0 | BL | 0.0 | 0.0 | 0.0 | BL | 0.0 | 0.0 | 0.0 | BL | 0.0 | 0.1 | 0.2 | BL | 0.1 | 0.2 | 0.3 |

After Adjustment of Rule ('BV', 'RZ', 'AZ'), and subsequent application of Dosing Matrix Coherency Policy to Rules ('BV', 'RZ', 'AP'), ('BH', 'RZ', 'AP'), ('BV', 'RP', 'AZ'), and ('BH', 'RP', 'AP')

| | rate = VN | | | | rate = RN | | | | rate = RZ | | | | rate = RP | | | | rate = RV | | |
|---|---|---|---|---|---|---|---|---|---|---|---|---|---|---|---|---|---|---|---|
| accl | AN | AZ | AP | accl | AN | AZ | AP | accl | AN | AZ | AP | accl | AN | AZ | AP | accl | AN | AZ | AP |
| BV | 5.0 | 6.0 | 7.0 | BV | 6.0 | 7.0 | 8.0 | BV | 7.0 | 9.5 | 9.5 | BV | 7.0 | 9.5 | 11.0 | BV | 8.0 | 10.0 | 12.0 |
| BH | 1.5 | 2.0 | 4.0 | BH | 3.0 | 4.0 | 6.0 | BH | 3.0 | 5.0 | 9.5 | BH | 5.0 | 7.0 | 9.5 | BH | 6.0 | 9.0 | 10.0 |
| BN | 0.3 | 0.5 | 0.7 | BN | 0.8 | 1.5 | 2.5 | BN | 1.5 | 2.0 | 3.0 | BN | 2.0 | 4.0 | 6.0 | BN | 3.0 | 5.0 | 7.0 |
| BM | 0.0 | 0.1 | 0.1 | BM | 0.1 | 0.3 | 0.4 | BM | 0.3 | 0.5 | 0.8 | BM | 0.5 | 0.8 | 1.0 | BM | 1.0 | 2.0 | 3.0 |
| BL | 0.0 | 0.0 | 0.0 | BL | 0.0 | 0.0 | 0.0 | BL | 0.0 | 0.0 | 0.0 | BL | 0.0 | 0.1 | 0.2 | BL | 0.1 | 0.2 | 0.3 |

TABLE 5

DOSING MATRIX COHERENCY POLICY

| | rate = VN | | | | rate = RN | | | | rate = RZ | | | | rate = RP | | | | rate = RV | | |
|---|---|---|---|---|---|---|---|---|---|---|---|---|---|---|---|---|---|---|---|
| accl | AN | AZ | AP | accl | AN | AZ | AP | accl | AN | AZ | AP | accl | AN | AZ | AP | accl | AN | AZ | AP |
| BV | 4 | 5 | 6 | BV | 4 | 5 | 6 | BV | 4 | 5 | 6 | BV | 4 | 5 | 6 | BV | 4 | 5 | 6 |
| BH | 3 | 4 | 5 | BH | 3 | 4 | 5 | BH | 3 | 4 | 5 | BH | 3 | 4 | 5 | BH | 3 | 4 | 5 |
| BN | 2 | 3 | 4 | BN | 2 | 3 | 4 | BN | 2 | 3 | 4 | BN | 2 | 3 | 4 | BN | 2 | 3 | 4 |
| BM | 1 | 2 | 3 | BM | 1 | 2 | 3 | BM | 1 | 2 | 3 | BM | 1 | 2 | 3 | BM | 1 | 2 | 3 |
| BL | 0 | 1 | 2 | BL | 0 | 1 | 2 | BL | 0 | 1 | 2 | BL | 0 | 1 | 2 | BL | 0 | 1 | 2 |

At 1708, the system predicts a next blood glucose level, or a set of next blood glucose levels with companion probabilities. This may be done, for example, using statistical modeling and/or trajectories. See, for example, the embodiments described and/or illustrated herein. Blood glucose levels may be predicted for more than one future time step. The method 1700 advances from 1708 to 1710. As in 1706, the individual control parameters predicted to produce the dose for the next blood sugar sample are adjusted, based on the comparison at 1704, possibly modulated by a scale factor that is a function of the probability of the predicted blood sugar, and then followed by the application of the dosing matrix coherency policy.

The dose for the current blood sugar value may then be determined using the updated fuzzy logic control parameters. The method 1700 proceeds from 1710 to 1712.

At 1712, the system determines whether the proposed dose satisfies one or more dose criteria. The dose criteria may comprise, for example, whether the proposed dose is within defined dose ranges, which may or may not vary based on patient specific information, such as current and/or historic blood glucose levels, patient weight, etc.; whether the probability that the proposed dose will result in a desired blood glucose level, such as a predicted blood glucose level, exceeds a threshold value, which may vary based on the proposed dose and/or patient specific information; whether or not the predicted next blood glucose level (or more than one predicted future blood glucose level) is within a threshold range, which may or may not vary based on patient specific information; and/or other variables, such as the time of day. Discrete circuitry, look-up tables, software subroutines, and/or combinations may be employed, for example, to determine whether the proposed dose satisfies the dose criteria. See, for example, the embodiments described or illustrated herein.

When the system determines at 1712 that the proposed dose does not satisfy the dosing criteria, the method 1700 proceeds from 1712 to 1706, where the proposed dose is adjusted and a new proposed dose is generated. The system may generate feedback that may be used to generate the new proposed dose at 1706. For example, if the proposed dose was outside a dose range, this information may be employed at 1706 when the new proposed dose is generated. In another example, if the predicted blood glucose level was outside an acceptable range, this information may be employed at 1706 when the new proposed dose is generated.

When the system determines at 1712 that the proposed dose satisfies the dosing criteria, the method proceeds from 1712 to 1714. At 1714, the system optionally adjusts control parameters to compensate for insulin sensitivity in real time. For example, the system may adjust control parameters to compensate for deviations between the reference trajectory and the patient's historical and/or projected blood glucose trajectories.

In one example embodiment, the BGL may be represented as a function y of the insulin dose: $y_t = f(\text{insulin dose})$, and descent gradient methods may be employed to adjust the control parameters (including model parameters), such as the methods discussed, described and illustrated herein and/or those described in the identified references.

Figure 19:
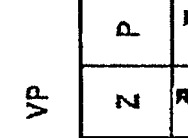
FIG. 19 illustrates an embodiment of a dosing rules matrix that may be employed, for example, by the embodiments described herein.

In another example, the doses in a matrix of fuzzy logic rules, such as the matrix illustrated in FIG. 19, may be adjusted based on a comparison of the blood glucose and active insulin levels with a reference trajectory, such as the idealized reference trajectory illustrated in FIG. 18. In some embodiments, the entire rules matrix may be adjusted to maintain integrity using linear or non-linear functions relating the doses of the rules matrix to one another. In another example, descent gradient methods may be employed in combination with adjustment of a fuzzy-logic rules matrix, to adjust control parameters, including model parameters.

The method 1700 proceeds from 1714 to 1716. At 1716, the system generates control signals to cause the commanded dose to be dispensed. The method 1700 proceeds with other processing, and may return to 1702.

Embodiments of the method 1700 illustrated in FIG. 17 may contain additional acts not shown in FIG. 17, may not contain all of the acts shown in FIG. 17, may perform acts shown in FIG. 17 in various orders, and may combine acts shown in FIG. 17.

FIG. 18 illustrates a reference trajectory 1802 and several measured and/or predicted trajectories 1804, 1806, 1808, 1810, 1812, 1814, 1816. The reference trajectory 1802 may comprise, for example, a theoretical idealized trajectory prepared by a physician. Time is represented along a horizontal axis 1818 and a blood sugar level is represented along a vertical axis 1820. Corresponding example proposed adjustments to insulin doses are indicated in a column 1822. For example, the trajectory 1810 is above the reference trajectory, indicating the blood sugar level is higher than the projected level. In this example, the proposed adjustment to the insulin dosage is an increase of 5%. In exemplary trajectories 1808, 1806, and 1804, progressively higher blood sugar levels result in progressively higher proposed adjustments to insulin dosage. On the other hand, trajectories 1812, 1814, and 1816 exemplify progressively lower blood sugar levels, resulting in progressively lower adjustments to insulin dosage. Some embodiments may impose safety and or other criteria onto the proposed adjustments. For example, a proposed adjustment may result in a dose that is between specified dosing levels in a set of dosing levels. The adjustment may be modified so that the dose is one of the specified dosing levels. In another example, a proposed increase may cause a proposed dose to exceed a maximum dose level. The proposed dose may be modified to remain below the maximum dose level. Some embodiments may adjust the reference trajectory based on differences between projected trajectories and measured trajectories.

FIG. 19 illustrates an example fuzzy logic Dosing Rules Matrix that may be applied by an insulin dispenser control system to control the dispensing of insulin. The cells represent insulin doses as a baseline dose, X, and a multiplier. The baseline dose may, for example, be a baseline dose selected by a provider, and may be patient specific. The first fuzzy input is the current blood glucose level BGL in mg/dl units, represented in the bottom four rows with fuzzy coverings VH (very high), HI (high), MD (medium), and NR (normal). The second fuzzy input is the rate of change of the blood glucose level, represented in row BGL RATE with fuzzy coverings VN (very negative), N (negative), Z (zero), P (positive) and VP (very positive). The third fuzzy variable is acceleration of the blood glucose level, represented in row BGL Acceleration with fuzzy coverings N (negative), Z (zero) and P (positive). Example trajectories corresponding to the blood glucose level rate of change and acceleration are illustrated in row BGL Trajectory for the previous two sample periods. The fuzzy coverings may be experimentally determined, and may vary based on additional factors such as the method of delivering a dose of insulin. The multipliers in the cells may be related to each other by linear or non-linear functions. In the illustrated example, the multipliers generally increase when moving from the bottom to the top, and when moving from left to right within a BGL rate group. The matrix may be adjusted by, for example, adjusting the multipliers or the base dosage, or combinations thereof. A look-up table may be employed in some embodiments.

Figure 20:
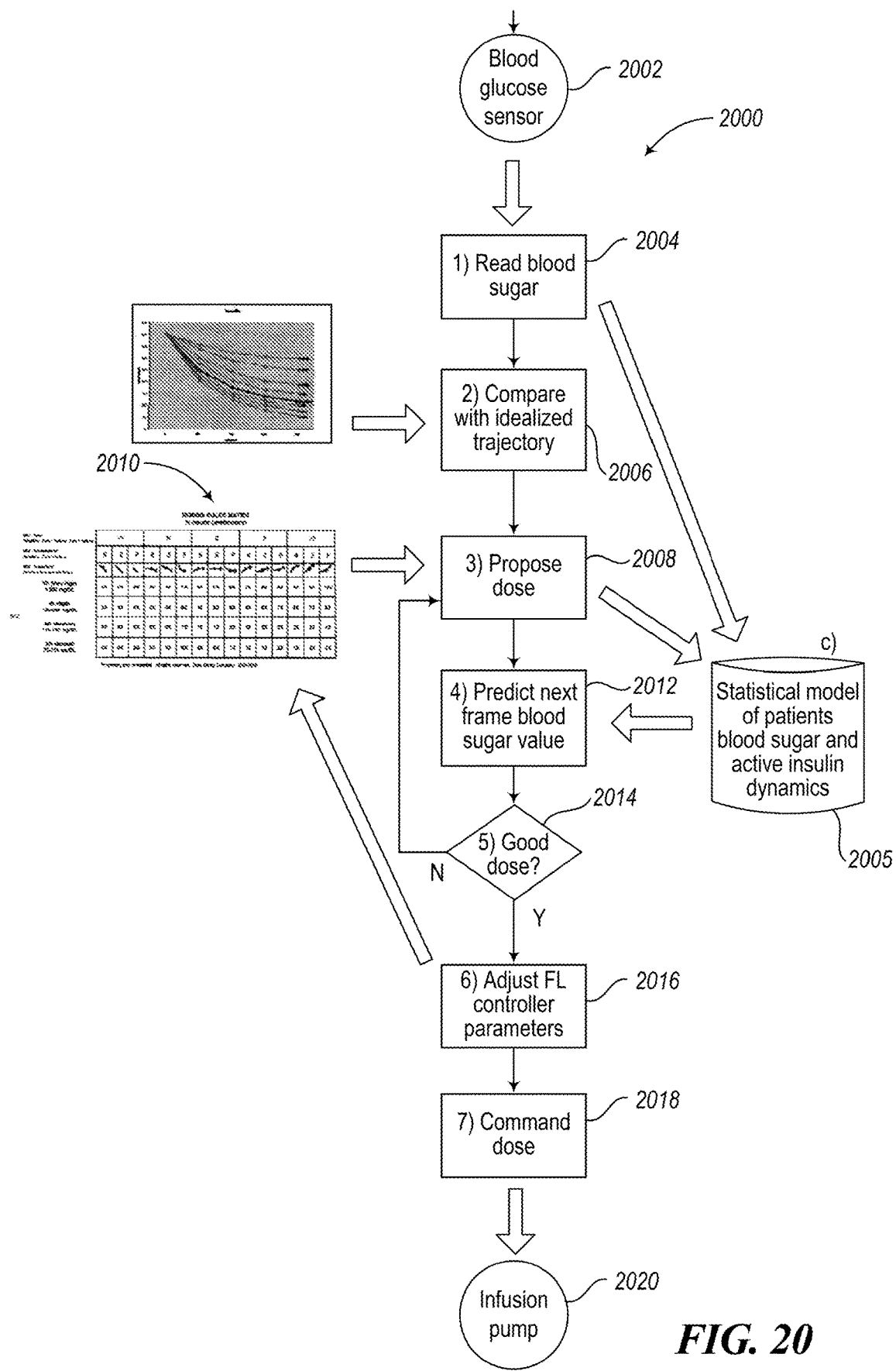
FIG. 20 illustrates an embodiment of a method of controlling an insulin pump that may be employed, for example, by the embodiments described herein.

FIG. 20 illustrates a mid-level flow diagram of an embodiment of a method 2000 of controlling dispensing of insulin that may be employed by a system, such as the dispenser control systems 100, 200 and 300 illustrated in FIGS. 1 through 3. For convenience, the method will be described with respect to the embodiment of a dispenser control system 100 illustrated in FIG. 1.

At 2002, the system 100 receives blood glucose data from a blood glucose sensor (see sensor 108 in FIG. 1). The method 2000 proceeds from 2002 to 2004. At 2004, the system 100 reads the blood glucose data, retrieves historical data and optionally updates a statistical model 2005. The method 2000 proceeds from 2004 to 2006. At 2006, the system 100 compares a trajectory for the current blood glucose reading to an idealized trajectory. The method 2000 proceeds from 2006 to 2008. At 2008, the system 100 proposes an insulin dose and optionally updates the statistical model 2005. As illustrated, the system 100 employs a fuzzy-logic rules matrix 2010 to propose the dose. The method 2000 proceeds from 2008 to 2012.

At 2012, the system 100 predicts a blood glucose value for a next sample period (for example, 15 minutes from the current sample). The method 2000 proceeds from 2012 to 2014. At 2014, the system 100 determines whether the dose satisfies a dosing criteria, this may be done, for example, as discussed with regard to other example embodiments herein. When the system 100 determines that the dosing criteria is satisfied, the method 2000 proceeds from 2014 to 2016. When the system 100 determines that the dosing criteria is not satisfied, the method 2000 proceeds from 2014 to 2008, where a new proposed dose is generated. As described above, the system 100 may factor in reasons why the dosing criteria was not satisfied when generating a new proposed dose.

At 2016, the system 100 adjusts the fuzzy logic control parameters in the fuzzy logic rules matrix 2010. This may be done, for example, as described with respect to other embodiments and examples herein. When the system 100 determines that the dosing criteria is satisfied, the method 2000 proceeds from 2016 to 2018. At 2018, the system 100 commands an insulin dose to be dispensed by an insulin pump 2020.

Embodiments of the method illustrated in FIG. 20 may contain additional acts not shown in FIG. 20, may not contain all of the acts illustrated in FIG. 20, may combine or separate acts illustrated in FIG. 20, and may perform the acts illustrated in FIG. 20 in various orders. Threshold levels and ranges employed by the method 2000 illustrated in FIG. 20 may be fixed or may be functions and may be based on statistical analysis.

The term "computer-readable medium" as used herein refers to any medium that participates in providing instructions to a system or a processor for execution. Such a medium may take many forms, including but not limited to, non-volatile media, and volatile media. Non-volatile media includes, for example, hard, optical or magnetic disks. Volatile media includes dynamic memory. Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM and an EEPROM, a FLASH-EEPROM, any other memory chip or cartridge, or any other medium from which a computer can read.

Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to computer system can receive the data on the telephone line and use an infrared transmitter to convert the data to an infrared signal. An infrared detector coupled to a system bus can receive the data carried in the infrared signal and place the data on system bus. The system bus carries the data to system memory, from which a processor retrieves and executes the instructions. The instructions received by system memory may optionally be stored on storage device either before or after execution by the processor.

Example 1

Insulin Dose Control (IDC) Method

An example of implementing an insulin dose control (IDC) method as described herein was performed as follows.

A bolus insulin dose was calculated based on measured values of blood glucose level (BGL) at the current time and at a previous time in the recent past. The BGL data were converted into three values for input to an IDC controller: B, the current BGL; R, the rate of change of the BGL with respect to time; and A, the acceleration of the BGL value with respect to time (i.e., the rate of change of R or the second derivative of BGL with respect to time). In the current example, the following specific definitions for B, R and A were used:

$B_i$ = the BGL value at the current time $T_i$
$B_{i-1}$ = the BGL value at the previous time $T_{i-1}$
$R_i = (B_i - B_{i-1})/(T_i - T_{i-1})$
$A_i = 2(R_i - R_{i-1})/(T_i - T_{i-2})$ (This can take into account variable time steps)

Use of more complex definitions is possible, for example, when there are more than two time points.

Figure 21:
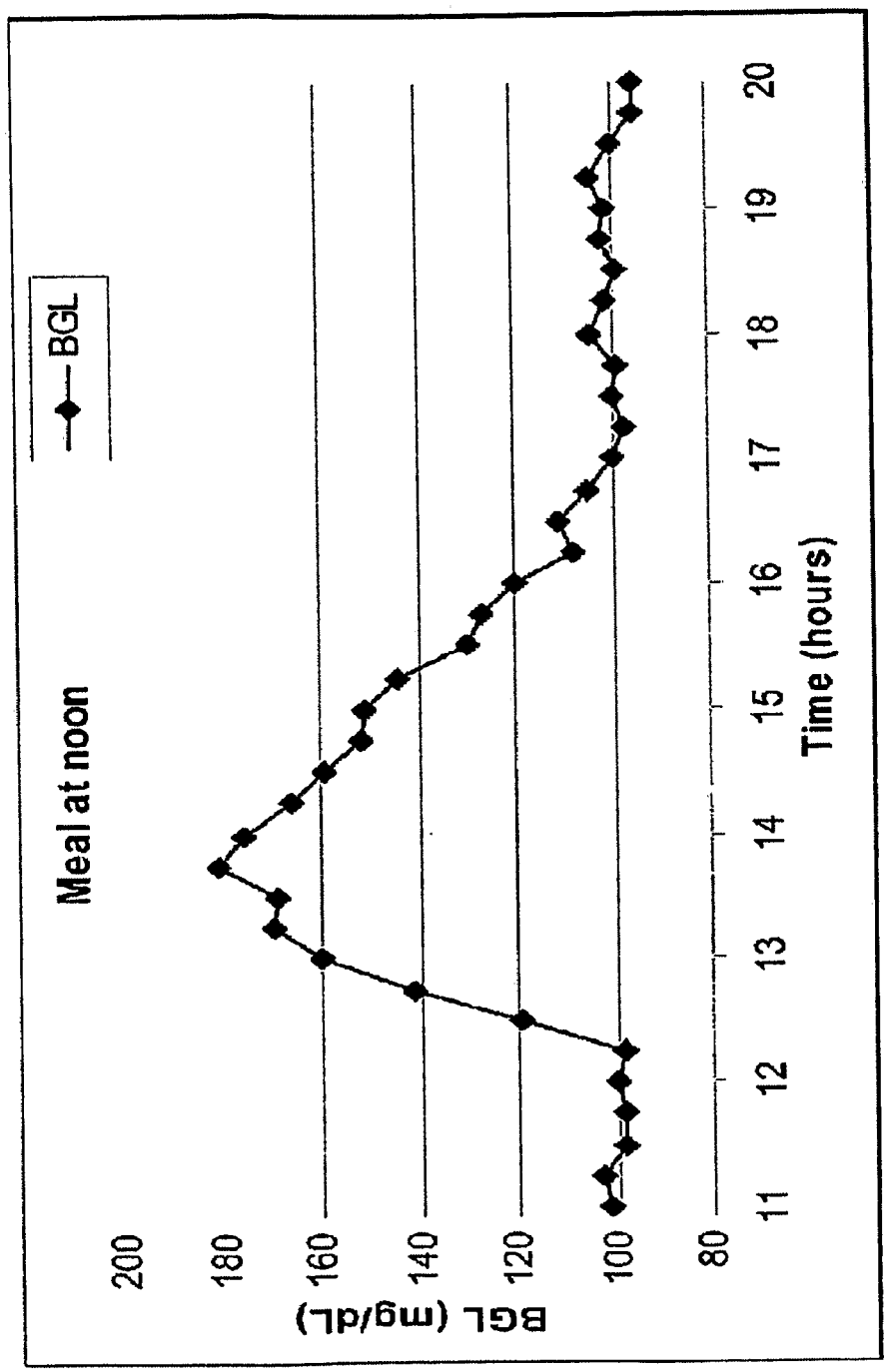
FIG. 21 shows an example of blood glucose levels measured before and after intake of a meal.

Results of measurement of BGL values beginning one hour before a meal and extending for eight hours after the meal are shown in FIG. 21. The BGL begins to increase sharply within 30 minutes of initiation of the meal, thus showing a large positive acceleration of the BGL. At about 60 minutes after initiation of the meal, the BGL level flattens, corresponding to a large negative acceleration. Moderate acceleration can be seen at other points on the curve. For a normal adult, 12-hour fasting blood values for glucose typically range between 60 and 100 mg/dL. The importance of B and R in determining insulin dose for treatment of diabetics has been discussed among those responsible for care of this population. The acceleration A may also be useful as an indicator of the eating behavior of a diabetic.

The insulin dose control method described herein and implemented in this example calculates insulin dose, D, as a function of the three variables identified above, i.e., D=ƒ(B, R, A). Further as described herein, a fuzzy control system is used to perform the dose calculation. Fuzzy logic and fuzzy control systems have been described as computing with words. Such methods have been found herein to be well suited for implementing protocols used by and incorporating dosing expertise of medical professionals involved in the treatment, for example, of type 1 diabetics. These methods have thus been used herein in developing the method for making decisions for administering insulin doses in treating diabetics.

Figure 22A:
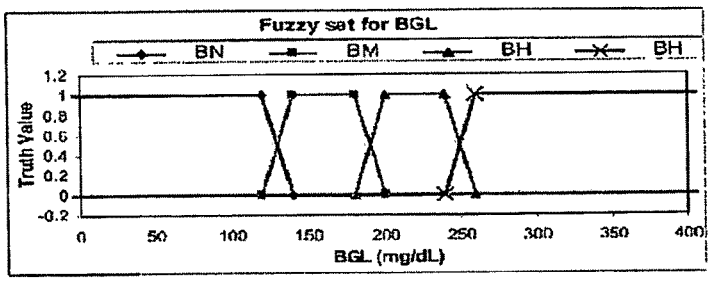
FIGS. 22A and 22B show an example of fuzzy coverings developed and used in an embodiment of an insulin dose control method.
Figure 22A:
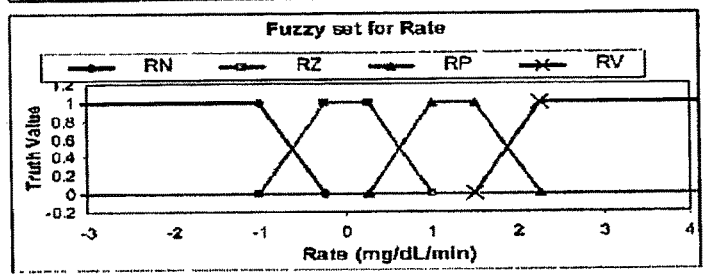
Figure 22A:
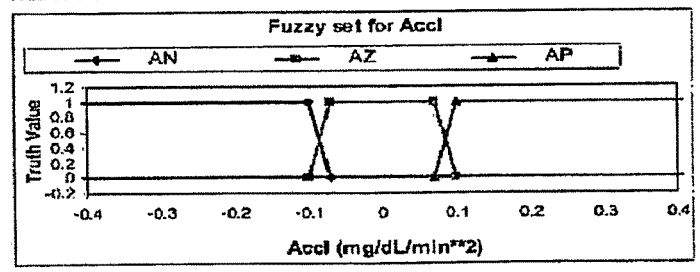
Figure 22B:
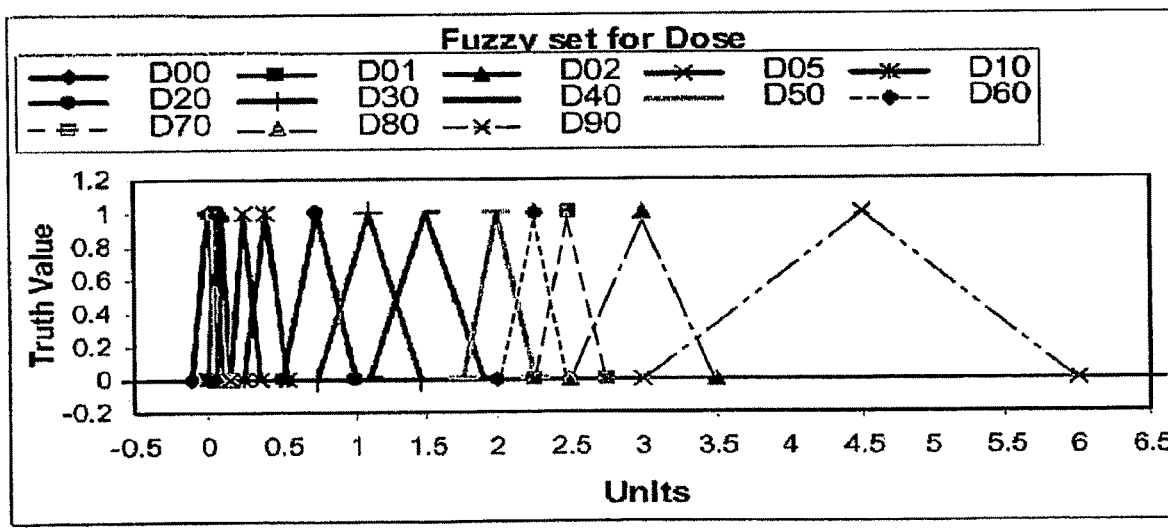

Fuzzy coverings are illustrated in FIGS. 22A and 22B. The four variable (inputs B, R, A, and output D) were fuzzified by defining a fuzzy set for each. Each member of an illustrated fuzzy set is a symmetric trapezoid with values of the members A, D, and W. A is the location of the center of the trapezoid. D is the half-width of the top. W is the half-width of the bottom. Thus, the (X,Y) coordinates of the four corners of the trapezoid are (A−W,0.0), (A−D,1.0), (A+D,1.0) and (A+W,0.0). If D is zero, the shape becomes an isosceles triangle, as in the output fuzzy set for dose shown in FIG. 22B. For the three input fuzzy sets, B, R, and A, the lowest member (BN, RN, AN) was extended to −infinity, while the highest member (BV, RV, AP) was extended to +infinity, as shown in FIG. 22A. No such extensions were done for members of the output fuzzy set.

An example is described here. The sensor sent a new BGL measurement of 193 mg/dL. The two previous BGL measurements were taken from the BGL historical data. These BGL measurements were 173 mg/dL (15 minutes earlier) and 161 mg/dL (30 minutes earlier). The rate R was calculated to be 1.333 mg/dL/min, and the acceleration A was calculated to be 0.035 mg/dL/min$^2$.

Fuzzification is the process of converting a crisp value (i.e., 193 mg/dL) into a set of truth values for the appropriated fuzzy members (i.e., 0.00, 0.35, 0.65, and 0.00 for BN, BM, BH, and BV, respectively.) Values for B, R, and A were fuzzified as follows:

B=193.0 was fuzzified to [('BM', 0.350, ('BH', 0.65)]
R=1.333 was fuzzified to [('RP', 1.00)]
A=0.035 was fuzzified to [('AZ', 1.00)]

After each of the crisp inputs was fuzzified, the rules, as shown in Table 6, were applied, using 'if-then' clauses. For example,
If B is BM and R is RP and A is AZ, then D is D40.

TABLE 6

IDC RULES

| BGL Rate: | RN | | | RZ | | | RP | | | RV | | |
|---|---|---|---|---|---|---|---|---|---|---|---|---|
| BGL Acceleration: | AN | AZ | AP | AN | AZ | AP | AN | AZ | AP | AN | AZ | AP |
| BGL Trajectory: | ↘ | ↘ | ↘ | → | → | → | ↗ | ↗ | ↗ | ↗ | ↗ | ↗ |
| BGL  BV | D01 | D10 | D70 | D01 | D20 | D80 | D01 | D80 | D80 | D01 | D90 | D90 |
| BH | D01 | D10 | D20 | D01 | D20 | D50 | D01 | D80 | D80 | D01 | D90 | D90 |
| BM | D01 | D05 | D10 | D01 | D10 | D20 | D01 | D40 | D40 | D01 | D80 | D90 |
| BN | D01 | D05 | D01 | D01 | D02 | D05 | D01 | D05 | D10 | D01 | D05 | D10 |

In this example, only two rules were fired:
If B is BM and R is RP and A is AZ, then D is D40 with firing strength 0.35; and
If B is BH and R is RP and A is AZ, then D is D80 with firing strength 0.65.
All other rules had zero firing strength.

The fuzzy output for dose was D40 with truth value 0.35 and D80 with truth value 0.65.

Figure 23:
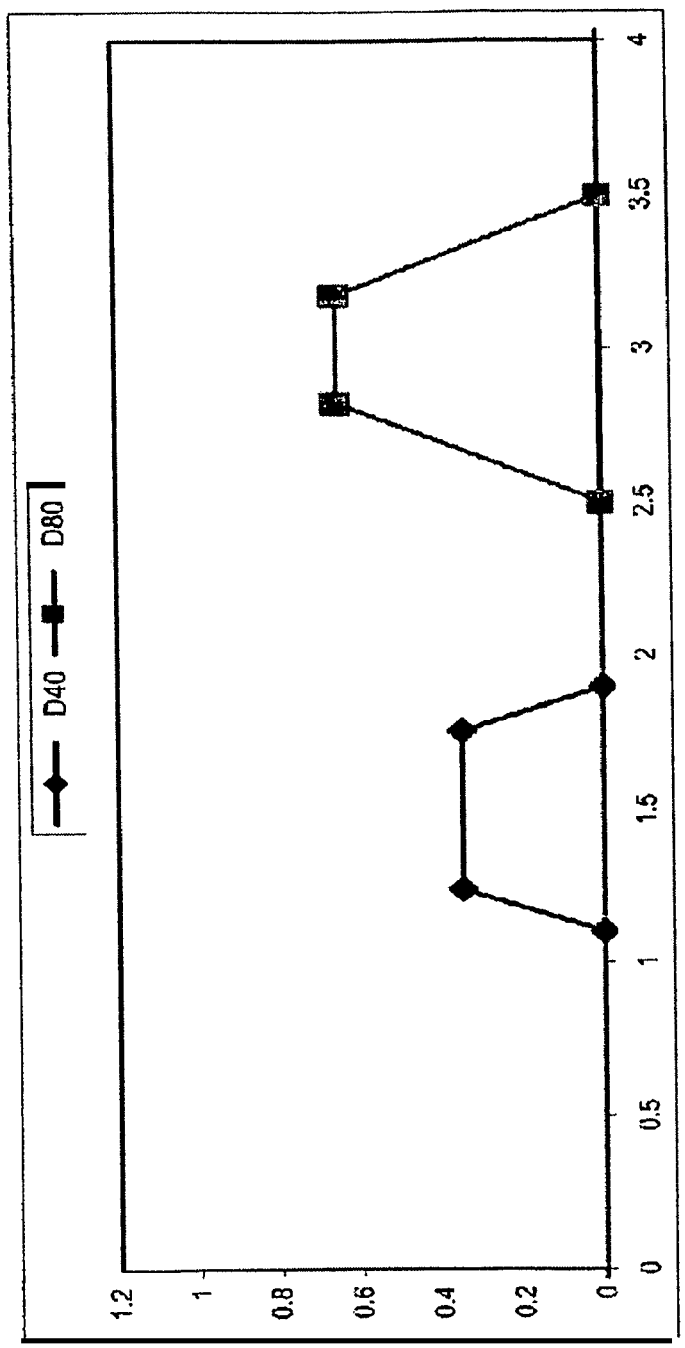
FIG. 23 illustrates an example of defuzzification of a fuzzy dose output in an embodiment of an insulin dose control method.

The fuzzy output was converted from a fuzzy result to a crisp result by the process of defuzzification. The defuzzified dose value is the centroid (sometimes called the center of mass or center of area) of the resulting fuzzy dose. In this example, D40 and D80 were clipped by their truth values, yielding the result illustrated in FIG. 23. The centroid in this case was 2.48. Thus, the crisp dose was determined to be 2.48.

Example Calculation of dose using fuzzy logic.
Min—max method for and & or operations.
Defuzification to get crisp value of dose. Calculation using centroid. Sum—product method for and & or operations.
Weighted sum calculation to get crisp value of dose.

Example 2

Determination of Viterbi Probability of a Sequence of Observed States

Below is an example of the Viterbi probability of the sequence of observed states 'NOR', 'MED', 'HIGH', 'VHIGH' given the below state transition probabilities and emission probabilities.

```
states = ('N', 'M', 'H', 'VH')
observations = ('NOR', 'MED', 'HIGH', 'VHIGH')
start_probability = {'N': 1.0, 'M': 0.0, 'H': 0.0, 'VH': 0.0}
transition_probability = {
    'N' : {'N': 0.1, 'M': 0.9, 'H': 0.0, 'VH': 0.0},
    'M' : {'N': 0.0, 'M': 0.2, 'H': 0.8, 'VH': 0.0},
    'H' : {'N': 0.0, 'M': 0.0, 'H': 0.2, 'VH': 0.8},
    'VH': {'N': 0.0, 'M': 0.0, 'H': 0.1, 'VH': 0.9},
}
emission_probability = {
    'N' : {'NOR': 1.0, 'MED': 0.0, 'HIGH': 0.0, 'VHIGH': 0.0},
    'M' : {'NOR': 0.0, 'MED': 1.0, 'HIGH': 0.0, 'VHIGH': 0.0},
    'H' : {'NOR': 0.0, 'MED': 0.0, 'HIGH': 1.0, 'VHIGH': 0.0},
    'VH': {'NOR': 0.0, 'MED': 0.0, 'HIGH': 0.0, 'VHIGH': 1.0},
}
def forward_viterbi(y, X, sp, tp, ep):
    T = { }
    for state in X:
        ##         prob.     V. path  V. prob.
        T[state] = (sp[state], [state], sp[state])
    for output in y:
        U = { }
        for next_state in X:
```

-continued

```
            total = 0
            argmax = None
            valmax = 0
            for state in X:
                (prob, v_path, v_prob) = T[state]
                p = ep[state][output] * tp[state][next_state]
                prob *= p
                v_prob *= p
                total += prob
                if v_prob > valmax:
                    argmax = v_path + [next_state]
                    valmax = v_prob
            U[next_state] = (total, argmax, valmax)
        T = U
    ## apply sum/max to the final states:
```

-continued

```
    total = 0
    argmax = None
    valmax = 0
    for state in X:
        (prob, v_path, v_prob) = T[state]
        total += prob
        if v_prob > valmax:
            argmax = v_path
            valmax = v_prob
    return (total, arg max, valmax)
def example2( ):
    return forward_viterbi(['NOR', 'MED', 'HIGH', 'VHIGH'],
            states,
            start_probability,
            transition_probability,
            emission_probability)
>>> example2( )
(0.57600000000000007, ['N', 'M', 'H', 'VH', 'VH'],
0.51840000000000008)
```

Thus, the probability of the sequence of observed states was determined to be 0.576.

Example 3

Prediction of Blood Glucose Values

A blood glucose feature list, with learned weights, in xml format was derived from the blood glucose prediction method illustrated in FIG. 16. The features were built in step 1604 and assigned default weights. The weights were updated in step 1606 using a training set of real patient blood sugar data. The training set of blood sugar values was read into the program at step 1602. The actual values and corresponding predicted next values are shown below in Table 7. This sequence of values was built iteratively by execution of steps 1608, 1610 and 1612 in succession as each new blood glucose value was entered.

TABLE 7

BLOOD GLUCOSE VALUES

| Actual Value | Predicted Next Value |
| --- | --- |
| 134.0 | 150.0 |
| 139.0 | 120.0 |
| 151.0 | 120.0 |
| 169.0 | 150.0 |
| 191.0 | 150.0 |
| 214.0 | 150.0 |
| 239.0 | 180.0 |
| 253.0 | 180.0 |
| 268.0 | 210.0 |
| 276.0 | 210.0 |
| 275.0 | 240.0 |
| 260.0 | 240.0 |
| 246.0 | 240.0 |
| 254.0 | 240.0 |
| 256.0 | 240.0 |
| 249.0 | 240.0 |
| 240.0 | 240.0 |
| 220.0 | 240.0 |
| 230.0 | 240.0 |
| 214.0 | 240.0 |
| 201.0 | 240.0 |
| 191.0 | 210.0 |
| 188.0 | 210.0 |
| 188.0 | 210.0 |

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

Although specific embodiments of and examples for the blood glucose prediction system, dispenser control systems, blood glucose sensors, and insulin dispensers, the devices, methods, and articles are described herein for illustrative purposes, various equivalent modifications can be made without departing from the spirit and scope of this disclosure, as will be recognized by those skilled in the relevant art. The various embodiments described above can be combined to provide further embodiments.

These and other changes can be made to the invention in light of the above-detailed description. In general, in the following claims, the terms used should not be construed to limit the invention to the specific embodiments disclosed in the specification and the claims. Accordingly, the invention is not limited by the disclosure, but instead its scope is to be determined entirely by the following claims.

The invention claimed is:

1. A blood glucose control system, comprising:
a data input subsystem configured to receive and store blood glucose-related data;
an output subsystem configured to generate a control signal to control dispensing of insulin based on the received blood glucose-related data and fuzzy-logic control parameters;
a parameter adjuster configured to adjust the fuzzy-logic control parameters based on the received and the stored blood-glucose related data; and
a pen-dispensing device coupled to the output subsystem.

2. The blood glucose control system of claim 1, further comprising: a blood glucose level predictor configured to predict blood glucose levels based on the received blood glucose-related data.

3. The blood glucose control system of claim 2, wherein the blood glucose level predictor is configured to predict blood glucose levels based on the stored blood glucose-related data.

4. The blood glucose control system of claim 2, wherein the blood glucose level predictor is configured to predict a subsequent blood glucose level based on a previously predicted blood glucose level.

5. The blood glucose control system of claim 2, wherein the blood glucose level predictor is configured to predict blood glucose levels based on a maintained fuzzy-logic rules matrix.

6. The blood glucose control system of claim 1, wherein the data input subsystem comprises a blood glucose sensor.

7. The blood glucose control system of claim 1 wherein the control system is configured to selectively transition between a post-meal correction mode and a fasting mode.

8. The blood glucose control system of claim 7, wherein the control system is configured to selectively transition from the post-meal correction mode to the fasting mode when a fasting criteria is satisfied.

9. The blood glucose control system of claim 7, wherein the control system is configured to selectively transition from the fasting mode to the post-meal correction mode when a prandial event is detected.

10. The blood glucose control system of claim 9, wherein the pen-dispensing device is configured to dispense a bolus insulin dose in the post-meal correction mode.

11. The blood glucose control system of claim 9, wherein the pen-dispensing device is configured to adjust a basal insulin dose in the post-meal correction mode.

12. The blood glucose control system of claim 7, wherein the control system is configured to selectively transition from the fasting mode to a user-input mode when a prandial event is detected.

13. The blood glucose control system of claim 1 wherein the fuzzy-logic control parameters comprise fuzzy-logic multipliers.

14. The blood glucose control system of claim 13, wherein the parameter adjuster is configured to selectively adjust a fuzzy logic rules matrix.

15. The blood glucose control system of claim 14, wherein the parameter adjuster is configured to selectively adjust the fuzzy logic rules matrix according to a dosing matrix coherency policy.

16. The blood glucose system of claim 1 wherein the parameter adjuster comprises at least one of a neural network and a dynamic Bayesian network.

17. The blood glucose control system of claim 1, wherein the control signal causes the pen-dispensing device to dispense or adjust a bolus and/or a basal dose.

18. A computer-implemented method, comprising:
receiving blood glucose-related data; retrieving stored blood glucose-related data; adjusting fuzzy-logic control parameters based on the received and the retrieved blood glucose-related data;
generating a control signal to control dispensing of insulin based on the received blood glucose-related data and fuzzy-logic control parameters, wherein the receiving, the retrieving, the adjusting and the generating are performed by one or more configured computing systems; and
dispensing insulin through a pen-dispensing device based on the control signal.

19. The computer-implemented method of claim 18, wherein the control signal causes the pen-dispensing device to dispense or adjust a bolus and/or a basal dose.

20. The computer-implemented method of claim 18, comprising predicting blood glucose levels based on the received blood glucose-related data.

21. The computer-implemented method of claim 20, comprising predicting blood glucose levels based on the retrieved blood glucose-related data.

22. The method of claim 20, wherein the predicting blood glucose levels comprises predicting a subsequent blood glucose level based on a previously predicted blood glucose level.

23. The method of claim 20, wherein the predicting blood glucose levels comprises maintaining a fuzzy-logic rules matrix.

24. The computer-implemented method of claim 18, comprising sensing blood glucose levels.

25. The computer-implemented method of claim 18, comprising selectively transitioning between using a post-meal correction protocol and a fasting protocol.

26. The computer-implemented method of claim 18, comprising transitioning from a post-meal correction protocol to a fasting protocol when a fasting criteria is satisfied.

27. The computer-implemented method of claim 18, comprising transitioning from a fasting protocol to a post-meal correction protocol when a prandial event is detected.

28. The computer-implemented method of claim 18, wherein the control signal causes the pen-dispensing device to dispense a bolus insulin dose in the post-meal correction mode.

29. The computer-implemented method of claim 18, wherein the control signal causes the pen-dispensing device is configured to adjust a basal insulin dose in the post-meal correction mode.

30. The computer-implemented method of claim 18, comprising transitioning from a fasting protocol to a user-input protocol when a prandial event is detected.

31. The computer-implemented method of claim 18, wherein the fuzzy-logic control parameters comprise fuzzy-logic multipliers.

32. The computer-implemented method of claim 31, wherein adjusting the fuzzy-logic control parameters comprises selectively adjusting a fuzzy logic rules matrix.

33. The method of claim 32, wherein the selectively adjusting the fuzzy logic rules matrix comprises applying a dosing matrix coherency policy.

34. The method of claim 32, wherein the adjusting fuzzy-logic control parameters comprises using at least one of a neural network and a dynamic Bayesian network.

35. The method of claim 32, wherein the adjusting fuzzy-logic control parameters occurs in real-time.

36. A device, comprising:
one or more memories;
one or more processors, which in operation:
predict blood glucose levels based on received blood glucose-related data; and
generate, using fuzzy logic, a control signal to control dispensing of insulin based on the received data and the predicted blood glucose levels, wherein the one or more processors, in operation:
predict blood glucose levels based on parameters of a statistical model;
adjust the parameters of the statistical model; and
an insulin pen dispenser, which, in operation, is controlled based on the control signal.

37. The device of claim 36, wherein the adjusting the parameters of the statistical model occurs in real-time as blood glucose-related data is received.

38. The device of claim 36, wherein the one or more processors, in operation: generate the control signal based on control parameters; and adjust the control parameters.

39. The device of claim 36, wherein, the one or more memories store historical blood glucose-related data; and the one or more processors, in operation, predict blood glucose levels based on stored historical blood glucose-related data.

40. The device of claim 36, wherein the control signal causes the pen-dispensing device to dispense or adjust a bolus and/or a basal dose.

* * * * *